US008911742B2

(12) United States Patent
Glenn et al.

(10) Patent No.: US 8,911,742 B2
(45) Date of Patent: *Dec. 16, 2014

(54) TRANSCUTANEOUS IMMUNIZATION WITHOUT HETEROLOGOUS ADJUVANT

(75) Inventors: Gregory M. Glenn, Gaithersburg, MD (US); Carl R. Alving, Bethesda, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/348,970

(22) Filed: Jan. 12, 2012

(65) Prior Publication Data
US 2012/0201845 A1    Aug. 9, 2012

Related U.S. Application Data

(63) Continuation of application No. 11/141,690, filed on Jun. 1, 2005, now abandoned, which is a continuation of application No. 09/337,746, filed on Jun. 22, 1999, now abandoned.

(60) Provisional application No. 60/090,169, filed on Jun. 22, 1998.

(51) Int. Cl.
| A61K 39/395 | (2006.01) |
| A61K 39/104 | (2006.01) |
| A61K 39/116 | (2006.01) |
| A61K 39/102 | (2006.01) |
| A61K 39/108 | (2006.01) |
| A61K 39/02  | (2006.01) |
| A61K 39/08  | (2006.01) |
| A61K 39/00  | (2006.01) |

(52) U.S. Cl.
CPC ....... *A61K 39/08* (2013.01); *A61K 2039/55555* (2013.01); *A61K 2039/54* (2013.01); *A61K 39/104* (2013.01); *A61K 39/116* (2013.01); *A61K 39/102* (2013.01); *A61K 39/0258* (2013.01); *A61K 39/099* (2013.01); *A61K 39/107* (2013.01)
USPC ..................................................... 424/184.1

(58) Field of Classification Search
None
See application file for complete search history.

(56) References Cited

U.S. PATENT DOCUMENTS

| 3,837,340 A | 9/1974 | Counter |
| 3,948,263 A | 4/1976 | Drake |
| 3,964,482 A | 6/1976 | Gerstel et al. |
| 3,982,536 A | 9/1976 | Krogseng |
| 4,196,191 A | 4/1980 | Almeida |
| 4,220,584 A | 9/1980 | Limjuco |
| 4,235,871 A | 11/1980 | Papahadjopoulos |
| 4,285,931 A | 8/1981 | Limjuco |
| 4,394,448 A | 7/1983 | Szoka |
| 4,411,888 A | 10/1983 | Klipstein |
| 4,455,142 A | 6/1984 | Martins |
| 4,484,923 A | 11/1984 | Amkraut |
| 4,497,796 A | 2/1985 | Salser |
| 4,587,044 A | 5/1986 | Miller |
| 4,692,462 A | 9/1987 | Banerjee |
| 4,725,271 A | 2/1988 | Korol |
| 4,732,892 A | 3/1988 | Sarpotdar |
| 4,743,588 A | 5/1988 | Mirejovsky |
| 4,761,372 A | 8/1988 | Maas |
| 4,764,381 A | 8/1988 | Bodor |
| 4,775,361 A | 10/1988 | Jacques |
| 4,783,450 A | 11/1988 | Fawzi |
| 4,834,985 A | 5/1989 | Eiger |
| 4,876,278 A | 10/1989 | Taylor |
| 4,877,612 A | 10/1989 | Berger |
| 4,887,611 A | 12/1989 | Rudiger |
| 4,892,737 A | 1/1990 | Bodor |
| 4,904,448 A | 2/1990 | Kawahara |
| 4,908,389 A | 3/1990 | Mahjour |
| 4,917,688 A | 4/1990 | Nelson |
| 4,917,895 A | 4/1990 | Lee |
| 4,921,757 A | 5/1990 | Wheatley |
| 4,929,442 A | 5/1990 | Powell |
| 4,946,853 A | 8/1990 | Bannon |
| 4,956,171 A | 9/1990 | Chang |

(Continued)

FOREIGN PATENT DOCUMENTS

| AU | 47099/89 | 6/1990 |
| EP | 0 891 770 | 1/1999 |

(Continued)

OTHER PUBLICATIONS

US 6,008,200, Dec. 1999, Krieg (withdrawn).

(Continued)

*Primary Examiner* — Yunsoo Kim
(74) *Attorney, Agent, or Firm* — Elizabeth Arwine

(57) ABSTRACT

Transcutaneous immunization can deliver antigen to the immune system through the stratum corneum without physical or chemical penetration to the dermis layer of the skin. This delivery system induces an antigen-specific immune response without the use of a heterologous adjuvant. This system can induce antigen-specific immune effectors after epicutaneous application of a formulation containing one or more antigensImmune responses that provide prophylactic and/or therapeutic treatments are preferred. Antigenic activities in the formulation may be found in the same molecule, two or more different molecules dissociated from each other, or multiple molecules in a complex formed by covalent or non-covalent bonds. For antigens which are proteinaceous, they may be provided in the formulation as a polynucleotide for transcutaneous genetic immunization. Besides simple application of a dry or liquid formulation to the skin, patches and other medical devices may be used to deliver antigen for immunization.

18 Claims, 4 Drawing Sheets

(56) References Cited

U.S. PATENT DOCUMENTS

| | | |
|---|---|---|
| 4,960,771 A | 10/1990 | Rajadhyaksha |
| 4,970,206 A | 11/1990 | Alexander |
| 5,003,987 A | 4/1991 | Grinwald |
| 5,008,050 A | 4/1991 | Cullis |
| 5,008,111 A | 4/1991 | Bodor |
| 5,023,252 A | 6/1991 | Hseih |
| 5,028,435 A | 7/1991 | Katz |
| 5,030,629 A | 7/1991 | Rajadhyaksha |
| 5,032,401 A | 7/1991 | Jamas |
| 5,032,402 A | 7/1991 | Digenis |
| 5,041,439 A | 8/1991 | Kasting |
| 5,045,317 A | 9/1991 | Chess |
| 5,049,386 A | 9/1991 | Eppstein |
| 5,049,387 A | 9/1991 | Amkraut |
| 5,059,189 A | 10/1991 | Cilento |
| 5,059,421 A | 10/1991 | Loughrey |
| 5,069,904 A | 12/1991 | Masterson |
| 5,082,866 A | 1/1992 | Wong |
| 5,108,921 A | 4/1992 | Low |
| 5,133,970 A | 7/1992 | Petereit et al. |
| 5,142,044 A | 8/1992 | Minaskanian |
| 5,162,315 A | 11/1992 | Rajadhyaksha |
| 5,164,406 A | 11/1992 | Helman |
| 5,166,320 A | 11/1992 | Wu |
| 5,169,637 A | 12/1992 | Lenk |
| 5,182,109 A | 1/1993 | Tamura |
| 5,196,410 A | 3/1993 | Francoeur |
| 5,200,393 A | 4/1993 | Weiner |
| 5,204,339 A | 4/1993 | Minaskanian |
| 5,215,520 A | 6/1993 | Shroot |
| 5,225,182 A | 7/1993 | Sharma |
| 5,232,935 A | 8/1993 | Colas |
| 5,234,959 A | 8/1993 | Minaskanian |
| 5,238,944 A | 8/1993 | Wick |
| 5,240,846 A | 8/1993 | Collins |
| 5,250,023 A | 10/1993 | Lee et al. |
| 5,252,334 A | 10/1993 | Chiang |
| 5,256,422 A | 10/1993 | Albert |
| 5,260,066 A | 11/1993 | Wood |
| 5,270,346 A | 12/1993 | Minaskanian |
| 5,279,544 A | 1/1994 | Gross et al. |
| 5,308,835 A | 5/1994 | Clements |
| 5,326,566 A | 7/1994 | Parab |
| 5,326,790 A | 7/1994 | Thornfeldt |
| 5,328,470 A | 7/1994 | Nabel |
| 5,332,576 A | 7/1994 | Mantelle |
| 5,332,577 A | 7/1994 | Gertner |
| 5,340,588 A | 8/1994 | Domb |
| 5,352,449 A | 10/1994 | Beltz |
| 5,399,346 A | 3/1995 | Anderson |
| 5,411,738 A | 5/1995 | Hind |
| 5,428,132 A | 6/1995 | Hirsch |
| 5,445,611 A | 8/1995 | Eppstein |
| 5,458,140 A | 10/1995 | Eppstein |
| 5,462,743 A | 10/1995 | Turner |
| 5,464,386 A | 11/1995 | Hofmann |
| 5,472,946 A | 12/1995 | Peck |
| 5,482,965 A | 1/1996 | Rajadhyaksha |
| 5,492,698 A | 2/1996 | Von Kleinsorgen |
| 5,505,956 A | 4/1996 | Kim |
| 5,505,958 A | 4/1996 | Bello |
| 5,518,725 A | 5/1996 | Daynes |
| 5,533,995 A | 7/1996 | Corish |
| 5,534,260 A | 7/1996 | Petersen |
| 5,536,263 A | 7/1996 | Rolf |
| 5,540,931 A | 7/1996 | Hewitt |
| 5,547,932 A | 8/1996 | Curiel |
| 5,573,778 A | 11/1996 | Therriault |
| 5,578,475 A | 11/1996 | Jessee |
| 5,580,859 A | 12/1996 | Felgner |
| 5,589,466 A | 12/1996 | Felgner et al. |
| 5,593,972 A | 1/1997 | Weiner |
| 5,601,827 A | 2/1997 | Collier |
| 5,607,691 A | 3/1997 | Hale |
| 5,612,382 A | 3/1997 | Fike |
| 5,614,212 A | 3/1997 | D'Angelo |
| 5,614,503 A | 3/1997 | Chaudhary |
| 5,620,896 A | 4/1997 | Hermann |
| 5,626,866 A | 5/1997 | Ebert |
| 5,643,578 A | 7/1997 | Robinson |
| 5,658,587 A | 8/1997 | Santus |
| 5,661,025 A | 8/1997 | Szoka |
| 5,661,130 A | 8/1997 | Meezan |
| 5,674,503 A | 10/1997 | Olafson |
| 5,676,954 A | 10/1997 | Brigham |
| 5,679,647 A | 10/1997 | Carson |
| 5,686,100 A | 11/1997 | Wille |
| 5,688,523 A | 11/1997 | Garbe et al. |
| 5,693,024 A | 12/1997 | Flower |
| 5,693,622 A | 12/1997 | Wolff |
| 5,695,991 A | 12/1997 | Lindholm |
| 5,697,901 A | 12/1997 | Eriksson |
| 5,698,416 A | 12/1997 | Wolf |
| 5,703,057 A | 12/1997 | Johnston |
| 5,705,151 A | 1/1998 | Dow |
| 5,718,914 A | 2/1998 | Foldvari |
| 5,720,948 A | 2/1998 | Brucks |
| 5,722,397 A | 3/1998 | Eppstein |
| 5,723,114 A | 3/1998 | Thornfeldt |
| 5,731,303 A | 3/1998 | Hsieh |
| 5,733,572 A | 3/1998 | Unger |
| 5,733,762 A | 3/1998 | Midoux |
| 5,736,154 A | 4/1998 | Fuisz |
| 5,736,392 A | 4/1998 | Hawley-Nelson |
| 5,736,524 A | 4/1998 | Content |
| 5,738,647 A | 4/1998 | Bernhard |
| 5,739,118 A | 4/1998 | Carrano |
| 5,741,510 A | 4/1998 | Rolf |
| 5,756,117 A | 5/1998 | D'Angelo |
| 5,760,096 A | 6/1998 | Thornfeldt |
| 5,766,899 A | 6/1998 | Kuo |
| 5,770,580 A | 6/1998 | Ledley |
| 5,773,022 A | 6/1998 | Nyqvist-Mayer |
| 5,780,050 A | 7/1998 | Jain |
| 5,783,567 A | 7/1998 | Hedley |
| 5,789,230 A | 8/1998 | Cotton |
| 5,804,214 A | 9/1998 | Wong |
| 5,804,566 A | 9/1998 | Carson |
| 5,811,406 A | 9/1998 | Szoka |
| 5,814,599 A | 9/1998 | Mitragotri |
| 5,814,617 A | 9/1998 | Hoffman |
| 5,824,538 A | 10/1998 | Branstrom |
| 5,827,703 A | 10/1998 | Debs |
| 5,827,705 A | 10/1998 | Dean |
| 5,830,876 A | 11/1998 | Weiner |
| 5,830,877 A | 11/1998 | Carson |
| 5,834,010 A | 11/1998 | Quan |
| 5,837,289 A | 11/1998 | Grasela |
| 5,837,533 A | 11/1998 | Boutin |
| 5,840,059 A | 11/1998 | March |
| 5,843,913 A | 12/1998 | Li |
| 5,844,107 A | 12/1998 | Hanson |
| 5,846,540 A | 12/1998 | Restifo |
| 5,846,949 A | 12/1998 | Wagner |
| 5,849,719 A | 12/1998 | Carson |
| 5,853,751 A | 12/1998 | Masiz |
| 5,856,187 A | 1/1999 | Restifo |
| 5,858,784 A | 1/1999 | Debs |
| 5,866,553 A | 2/1999 | Donnelly |
| 5,877,159 A | 3/1999 | Powell |
| 5,877,302 A | 3/1999 | Hanson |
| 5,879,326 A | 3/1999 | Godshall et al. |
| 5,885,971 A | 3/1999 | German |
| 5,910,306 A | 6/1999 | Alvin |
| 5,910,488 A | 6/1999 | Nabel |
| 5,914,114 A | 6/1999 | Cassels |
| 5,916,879 A | 6/1999 | Webster |
| 5,935,838 A | 8/1999 | Askeloef |
| 5,961,979 A | 10/1999 | Srivastava |
| 5,980,898 A | 11/1999 | Glenn |
| 5,985,847 A | 11/1999 | Carson |
| 5,993,849 A | 11/1999 | Assmus et al. |
| 5,993,852 A | 11/1999 | Foldvari et al. |
| 6,019,982 A | 2/2000 | Clements et al. |

(56) References Cited

U.S. PATENT DOCUMENTS

| | | | |
|---|---|---|---|
| 6,022,316 | A | 2/2000 | Eppstein et al. |
| 6,033,673 | A | 3/2000 | Clements |
| 6,033,684 | A | 3/2000 | Norcia |
| 6,039,969 | A | 3/2000 | Tomai' |
| 6,063,399 | A | 5/2000 | Assmus et al. |
| 6,087,341 | A | 7/2000 | Khavari |
| 6,090,790 | A | 7/2000 | Eriksson |
| 6,142,939 | A | 11/2000 | Eppstein et al. |
| 6,149,919 | A | 11/2000 | Domenighini et al. |
| 6,165,458 | A | 12/2000 | Foldvari et al. |
| 6,165,500 | A | 12/2000 | Cevc |
| 6,173,202 | B1 | 1/2001 | Epstein |
| 6,180,136 | B1 | 1/2001 | Larson |
| 6,183,434 | B1 | 2/2001 | Eppstein |
| 6,190,367 | B1 | 2/2001 | Hall |
| 6,190,689 | B1 | 2/2001 | Hoffmann et al. |
| 6,207,184 | B1 | 3/2001 | Ikeda et al. |
| 6,210,672 | B1 | 4/2001 | Cowing |
| 6,256,533 | B1 | 7/2001 | Yuzhakov et al. |
| 6,290,991 | B1 | 9/2001 | Roser et al. |
| 6,312,612 | B1 | 11/2001 | Sherman et al. |
| 6,331,266 | B1 | 12/2001 | Powell et al. |
| 6,331,310 | B1 | 12/2001 | Roser et al. |
| 6,334,856 | B1 | 1/2002 | Allen et al. |
| 6,348,212 | B2 | 2/2002 | Hymes et al. |
| 6,348,450 | B1 | 2/2002 | Tang et al. |
| 6,365,178 | B1 | 4/2002 | Venkateshwaran et al. |
| 6,379,324 | B1 | 4/2002 | Gartstein et al. |
| 6,406,705 | B1 | 6/2002 | Davis et al. |
| 6,413,523 | B1 | 7/2002 | Clements |
| 6,440,096 | B1 | 8/2002 | Lastovich et al. |
| 6,451,240 | B1 | 9/2002 | Sherman et al. |
| 6,454,755 | B1 | 9/2002 | Godshall |
| 6,471,903 | B2 | 10/2002 | Sherman et al. |
| 6,797,276 | B1 | 9/2004 | Glen et al. |

FOREIGN PATENT DOCUMENTS

| | | |
|---|---|---|
| JP | 04187640 | 10/1993 |
| WO | WO 91/05529 | 5/1991 |
| WO | WO 92/03122 | 3/1992 |
| WO | WO 94/21230 | 9/1994 |
| WO | WO 95/17211 | 6/1995 |
| WO | WO 95/18603 | 7/1995 |
| WO | WO 96/06627 | 3/1996 |
| WO | WO 96/19976 | 4/1996 |
| WO | WO 96/14704 | 5/1996 |
| WO | WO 96/14855 | 5/1996 |
| WO | WO 98/20734 | 5/1996 |
| WO | WO 96/25190 | 8/1996 |
| WO | WO 97/04832 | 2/1997 |
| WO | WO 97/07734 | 3/1997 |
| WO | WO 97/24447 | 7/1997 |
| WO | WO 97/31119 | 8/1997 |
| WO | WO 97/35957 | 10/1997 |
| WO | WO 98/00193 | 1/1998 |
| WO | WO 98/01538 | 1/1998 |
| WO | WO 98/10750 | 3/1998 |
| WO | WO 98/29134 | 7/1998 |
| WO | WO 98/42375 | 10/1998 |
| WO | WO 98/46208 | 10/1998 |
| WO | WO 99/04009 | 1/1999 |
| WO | WO 99/08689 | 2/1999 |
| WO | WO 99/08713 | 2/1999 |
| WO | WO 99/13915 | 3/1999 |
| WO | WO 99/26662 | 6/1999 |
| WO | WO 99/41366 | 8/1999 |
| WO | WO 99/43350 | 9/1999 |
| WO | WO 99/47164 | 9/1999 |
| WO | WO 99/47165 | 9/1999 |
| WO | WO 99/47167 | 9/1999 |
| WO | WO 99/53960 | 10/1999 |
| WO | WO 99/60167 | 11/1999 |
| WO | WO 99/61078 | 12/1999 |
| WO | WO 99/62537 | 12/1999 |
| WO | WO 00/33812 | 6/2000 |
| WO | WO 00/44349 | 8/2000 |
| WO | WO 00/61184 | 10/2000 |
| WO | WO 00/74714 | 12/2000 |
| WO | WO 00/74763 | 12/2000 |
| WO | WO 00/74763 A3 | 12/2000 |
| WO | WO 00/74766 | 12/2000 |
| WO | WO 01/34185 | 5/2001 |
| WO | WO 01/90758 | 11/2001 |
| WO | WO 02/02179 | 1/2002 |
| WO | WO 02/05889 | 1/2002 |
| WO | WO 02/07813 | 1/2002 |
| WO | WO 02/064162 | 8/2002 |
| WO | WO 02/064193 | 8/2002 |
| WO | WO 02/74244 | 9/2002 |

OTHER PUBLICATIONS

Alving "Effectiveness of liposomes as potential carriers of vaccines: Applications to cholera toxin and human malaria sporozoite antigent" Vaccine 4:166-172 (1986).

Alving "Liposomes as carriers of antigens and adjuvants" J. Immunol. Methods 140:1-13 (1991).

Alving "Lipopolysaccharide, lipid A, and liposomes containing lipid A as immunologic adjuvants" Immunobioly 187: 430-446 (1993).

Alving "Novel adjuvant strategies for experimental malaria and AIDS vaccines" Ann. NY Acad. Sci. 690:265-275 (1993).

Alving "The preparation and use of liposomes in immunological studies" in: *Liposome Technology*, CRC Press 3:317-343 (1993).

Alving "Cytotoxic T lymphocytes induced by liposomal antigens: Mechanisms of immunological presentation" AIDS Res Hum Retroviruses 10 suppl 2 S91-S94 (1994).

Alving "Liposomes as carriers of peptide antigens: induction of antibodies and cytotoxic T lymphocytes to conjugated and unconjugated peptides" Immunol Rev 145:5-31 (1995).

Allison "Hydrogen bonding between sugar and protein is responsible for inhibition of dehydration-induced protein unfolding" Arch. Biochem, Biophys. 365:289-298 (1999).

Allison "Optimization of storage stability of lyophilized actin using combinations of disaccharides and dextran" J. Pharm. Sci. 89:199-214 (2000).

Anderson "Guinea Pig Maximization Test: Effect TRype of Freund's Complete AdjuvantEmulsion and of Challenge Site Location" Dermatosen 33: 132-136 (1985).

Andya "The effect of formulation excipients on protein stability and aerosol performance of spray-dried powders of a recombinant humanized anti-lgE monocional antibody" Pharm. Res. 16:350-358 (1999).

Arakawa "Protein-solvent interactions in pharmaceutical formulations" Pharm. Res. 8:285-291 (1999).

Arany "Correlation between pretreatment levels of interferon response genes and clinical responses to an immune response modifier (imiquimod) in genital warts" Antimicrob Agents Chemother 44:1869-1873 (2000).

Artmann "Liposomes from soya phospholipids as percutaneous drug carriers. 1st communication: qualitative in vivo investigations with antibody-loaded liposomes" Arzneimittelforschung 40: 1363-1365 (1990).

Becker "Dengue fever virus and Japanese encephalitis virus synthetic peptides, with motifs to fit HLA class 1 haplotypes prevalent in human populations in endemic regions, can be used for application to skin Langerhans cells to prime antiviral CD8 cytotoxic T cells (CTLs)—A novel approach to the protection of humans" Virus Genes 9:33-45 (1994).

Becker "An analysis of the role of skin Langerhans cells (LC) in the cytoplasmic processing of HIV-1 peptides after "Peplotion" transepidermal transfer and HLA class I presentation to CD8 CTLs—An approach to immunization of humans" Virus Genes 9:133-147 (1994).

Becker "HIV-Peplotion Vaccine" in Novel Strategies and Design and Production of Vaccines, ed. S. Cohen and A. Shafferman, Plenum Press NY 97-104 (1996).

(56) References Cited

OTHER PUBLICATIONS

Becker "Mechanism in allergic contact dermatitis" Exp. Dermatol. 2:63-69 (1993.
Birch "Trehaloses" Adv. Carb. Chem. Biochem. 18:201-225 (1993).
Blauvelt "Human Langerhans cells express E-cadherin" J. Invest. Dermatol. 104:293-296 (1995).
Bos "The 500 dalton rule for the skin penetration of chemical compounds and drugs" Exp. Dermatol. 9:165-169 (2000).
Bovsun "DNA vaccine rubbed on skin provokes immune response" Biotechnol Newswatch pp. 4 (Sep. 20, 1999).
Bowen "Cholera toxin acts as a potent adjuvant for the induction of cytotoxic T-lymphocyte responses with non-replicating antigens" Immunol. 81:338-342 (1994).
Buates "Treatment of experimental Leishmaniasis with the immunomodulators imiquimod and S-28463: Efficacy and mode of action" J Infect Dis 179:1485-1494 (1999).
Castle "Clinical relevance of age-related immune dysfunction" Clin. Infect. Dis. 31:578-585 (2000).
Cevc "Transfersomes, liposomes and other lipid suspensions on the skin: permeation enhancement, vesicle penetration, and transdermal drug delivery" Crit. Rev. in Ther. Drug Carrier Sys. 13: 257-388 (1996).
Chen "Adjuvation of epidermal powder immunization" Vaccine 19:2908-2917 (2001).
Chen "Serum and mucosal immune responses to an inactivated influenza virus vaccine induced by epidermal powder immunization" J Virol 75:7956-7965 (2001).
Chen "Induction of systemic immune responses in sheep by topical application of cholera toxin to skin" Vet Immunol Immunopathol 77:191-199 (2000).
Chin "Antibody response against *Pseudomonas aeruginosa* membrane proteins in experimentally infected sheep" Vet. Microbiol. 43:21-32 (1995).
Chin "Manipulating systemic and mucosal immune responses with skin-deliverable adjuvans" J. Biotechnol. 44:13-19 (1996).
Condon "DNA-based immunization by in vivo transfection of dendritic cells" Nature Med. 2:1122-1128 (1996).
Costantino "Effect of excipients on the stability and structure of lyophilized recombinant human growth hormone" J. Pharm. Sci. 87:1412-1420 (1998).
Craig "Cutaneous responses to cholera skin toxin in man, I. Responses in unimmunized American males" J. Infect. Dis. 125:203-215 (1972).
De Haan "Liposomes as an immunoadjuvant system for stimulation of mucosal and systemic antibody responses against inactivated measles virus administered intranasally to mice" Vaccine 13:1320-1324 (1995).
Egbaria "Liposomes as topical drug delivery system" Adv Drug Delivery Rev 5:287-300 (1990).
El-Ghorr "Transcutaenous immunisation with herpes simplex virus stimulates immunity in mice" FEMS Immunol Med Micro 29:255-261 (2000).
Enk "An essential role for Langerhans cell-derived IL-1 beta in the initiation of primary immune responses in skin" J Immunol 151:2390-2398 (1993).
Fan "Immunization via hair follicles by topical application of naked DNA to normal skin" Nature Biotechnol 17:870-872 (1999).
Fleisher "Topical delivery of growth hormone releasing peptide using liposomal systems: An in vitro study using hairless mouse skin" Life Sci 57:1293-1297 (1995).
Frank "Long-Term stabilization of biologicals" Bio/Technology 12:253-256 (1994).
Gekko "Mechanism of protein stabilization by glycerol: Preferential hydration in glycerol-water mixtures" Biochemistry 20:4667-4676 (1981).
Glenn "Murine IgG subclass antibodies to antigens incorporated in liposomes containing lipid A" Immunol Lett 47:73-78 (1995).
Glenn "Skin immunization made possible by cholera toxin" Nature 391:851 (1998).
Glenn "Transcutaneous immunization with cholera toxin protects mice against lethal mucosal toxin challenge" J Immunol 161:3211-3214 (1998).
Glenn "Transcutaneous immunization with bacterial ADP-ribosylating exotoxins as antigens and adjuvants" Infect Immun 67:1100-1106 (1999).
Glenn et al. "Advances in vaccine delivery: transcutaneous immunisation" Ashley Publications Ltd. ISSN, 1999, pp. 797-805.
Glenn "Transcutaneous immunisation" Exp Opin Invest Drugs 8:797-805 (1999).
Glenn "Transcutaneous immunization" In: *The Journal Report*, NIAID, pp. 91-93 (2000).
Glenn "Transcutaneous immunization: A human vaccine delivery strategy using a patch" Nature Med 6:1403-1406 (2000).
Glenn "Transcutaneous immunization" In: *Vaccine Adjuvants*, Human Press pp. 315-326 (2000).
Glenn "Transcutaneous immunization" In: *New Vaccine Technologies*, Landes Biosciences pp. 292-304 (2001).
Glueck "Safety and Immunogenicity of intranasally administered inactivated trivalent virosome-formulated influenza vaccine *Escherichia coli* heat-labile toxin as a mucosal adjuvant" J Infect Dis 181:1129-1132 (2000).
Gockel "Transcutaneous immunization induces mucosal and systemic immunity: A potent method for targeting immunity to the female reproductive tract" Mol Immunol 37:537-544 (2000).
Goodnow "Chance encounters and organized rendezvous" Immunol Rev 156:5-10 (1997).
Grubauer "Lipid Content and Lipid Type as Determinants of the Epidermal Permeability Barrier" J. Lipid Res. 30: 89-96 (1989).
Gupta "Adjuvants for human vaccines—current status, problems and future prospects" Vaccine 13:1263-1276 (1995).
Hagiwar "Effectiveness and safety of mutant *Escherichia coli* heat-labile enterotoxin as an adjuvant for nasal influenza vaccine" Vaccine 19:2071-2079 (2001).
Hagiwara "Effects of intranasal administration of cholera toxin (or *Escherichia coli* heat-labile enterotoxin) B subunits supplemented with a trace amount of the holotoxin on the brain" Vaccine 19:1652-1660 (2001).
Hammond "Transcutaneous immunization of domestic animals: Opportunities and challenges" Adv Drug Delivery Rev 43:45-55 (2000).
Hammond "Transcutaneous immunization: T cell responses and boosting of existing immunity" Vaccine 19:2701-2707 (2001).
Hanson "Introduction to formulation of protein pharmaceuticals" In: *Stability in Protein Pharmaceuticals*, Plenum pp. 209-233 (1992).
Hioe "Comparison of adjuvant formulations of cytotoxic T cell induction using synthetic peptides" Vaccine 14:412-418, (1996).
Hoelzle "Increased accumulation of trehalose in rhizobia cultured under 1% oxygen" Appl Environ Microbiol 56:3213-3215 (1990).
Hsiung *Diagnostic Virology 3rd Ed.*, Yale Univ. Press pp. 29-34 (1982).
Iizuka "Two simple methods for the evaluation of topically active anti-inflammatory steroidal ointments" Agents Actions 11:254-259 (1981).
Izutsu "Increased stabilizing effects of amphiphilic excipients on freeze-drying of lactate dehydrogenase (LDH) by dispersion into sugar matrices" Pharm Res 12:838-843 (1995).
Johnson et al. "Vaccination onto bare skin", Scientific Correspondence, Nature 388: 729-730 (1997).
Kahan "Immunosuppressive therapy" Current Opin Immunobiology 4:553-560 (1992).
Katoh "Acute cutaneous barrier perturbation induces maturation of Langerhans' cells in hairless mice" Acta Derm Venereol (Stockh) 77:365-369 (1997).
Knop "Cellular and molecular mechanisms in the induction phase of contact sensitivity" Intl Arch Allergy Immunol 107:231-232 (1995).
Korting "Topical liposome drugs to come: what the patent literature tells us" J Am Acad Dermatol 25:1068-1071 (1991).
Korting "Interaction of liposomes with human epidermis reconstructed in vitro" Br J Dermatol 132:571-579 (1995).
Kosecka "Pertussis toxin stimulates hypersensitivity and enhances nerve-mediated antigen uptake in rat intestines" Am J Physiol 267:G745-G752 (1994).

(56) References Cited

OTHER PUBLICATIONS

Kumamoto "Induction of tumor-specific protective immunity by in situ Langerhans cell vaccine" Nature Biotech 20:64-69 (2002).
Lacroix "Presentation de Malades: Percuti B.C.G. Diagnostic (B.C. G. Patch)" Alger Medicale 56: 473-477 (1952) with English Translation.
Lane "In vitro-evaluation of human lymphocyte function" In: *Handbook of Experimental Immunology 4th Ed.*, vol. 2, Blackwell pp. 66.5-66.7 (1986).
Letvin, Journal of Clinical Invest. 2002, vol. 109, p. 15-20.
Liu "Topical application of HIV DNA vaccine with cytokine-expression plasmids induces strong antigen-specific immune responses" Vaccine 20:42-48 (2002).
Lu "Mutant *Escherichia coli* heat-labile enterotoxin [LT (R192G)] enhances protective humoral and cellular immune responses to orally administered inactivated influenza vaccine" Vaccine 20:1019-1029 (2002).
Lüders "Untersuchungen zu einer Verbesserung der Tuberkulinprobe" Beitr. Klin. Tuberk. 134: 130-142 (1966) with English Translation.
Luo "Synthetic DNA delivery systems" Nature Biotechnol 18:33-37 (2000).
Mahmoud "Parasitic protozoa and helminths: Biological and immunological challenges" Science 246:1015-1022 (1989).
Marinaro "Mucosal effect of cholera toxin in mice results from induction of T helper 2 (Th2) cells and IL-4" J Immunol 155:4621-4629 (1995).
McCluskie "Route and method of delivery of DNA vaccine influence immune responses in mice and non-human primates" Mol Med 5:287-300 (1999).
Mengiardi "Virosomes as carriers for combined vaccines" Vaccine 13:1306-1315 (1995).
Menon "De Novo Sterologenesis in the Skin. II. Regulation by Cutaneous Barrier Requirements" J. Lipid Res. 26: 418-427 (1985).
Mitragotri "Ultra-Sound Mediated Transdermal Delivery" Science 269: 850-853 (1995).
Norimatsu "Effects of aluminum adjuvant on systemic reactions of lipopolysaccharides in swine" Vaccine 13:1325-1329 (1995).
Mezei "Liposomes—a selective drug delivery system for the topical route of administration, Lotion dosage form" Life Sci 26:1473-1477 (1980).
Moghimi "Current progress and future prospects of liposomes in dermal drug delivery" J Microencapsul 10:155-162 (1993).
Ockenhouse "Sequestrin, a CD36 recognition protein on *Plasmodium falciparum* malaria-infected erythrocytes identified by anti-idiotype antibodies" Proc Natl Acad Sci USA 88:3175-3179 (1991).
Paul "Transdermal immunization with large proteins by means of ultradeformable drug carriers" Eur J Immunol 5:3521-3524 (1995).
Paul "Noninvasive administration of protein antigens: Transdermal immunization with bovine serum albumum in transferosomes" Vaccine Res 4:145-164 (1995).
Peters "Dendritic cells: From ontogenetic orphans to myelomonocytic descendants" Immunol Today 17:273-278 (1996).
Podda "The adjuvanted influenza vaccines with novel adjuvants: Experience with the MF59-adjuvated vaccine" Vaccine 19:2673-2680 (2001).
Powers "In previously immunized elderly adults inactivated influenza A (H1N1) virus vaccines induce poor antibody responses that are not enhanced by liposome adjuvant" Vaccine 13:1330-1335 (1995).
Ranade "Drug delivery systems, 6. Transdermal drug delivery" J Clin Pharmacol 31:401-418 (1991).
Rao "Intracellular processing of liposome-encapsulated antigens by macrophages depends upon the antigen" Infect Immun 63:2396-2402 (1995).
Remington: The Science and Practice of Pharmacy, ed. Hoover, 2000, 20th ed., p. 843-844.
Sanchez "Formulation strategies for the stabilization of tetanus toxoid in poly(lactide-co-glycolide) microspheres" Intl J Pharm 185:255-266 (1999).
Sauzet "Long-lasting anti-viral cytotoxic T lympocytes induced in vivo with chimeric-multirestricted lipopeptides" Vaccine 13:1339-1345 (1995).
Schaefer-Korting "Liposome preparations: A step forward in topical drug therapy for skin disease?" J Am Acad Dermatol 21:1271-1275 (1989).
Scharton-Kersten "Principles of transcutaneous immunization using cholera toxin as an adjuvant" Vaccine 17 suppl 2:S237-S43 (1999).
Scharton-Kersten "Transcutaneous immunization with bacterial ADP-ribosylating exotoxins, subunits, and unrelated adjuvants" Infect Immun 68:5306-5313 (2000).
Scheuplein "Percutaneous Absorption After Twenty-five Years or 'Old Wine in New Wineskins'" J. Investig. Dermatol. 67: 31-38 (1976).
Schmit "Bacterial toxins: Friends or foes" Emerging Infect Dis 5:224-234 (1999).
Schwarzenberger "Contact allergens and epidermal proinflammatory cytokines modulate Langerhans cell E-cadherin expression in situ" J Invest Dermatol 106:553-558 (1996).
Seo "Percutaenous peptide immunization via corneum barrier-disrupted murine skin for experimental tumor immunopropylaxis" Proc Natl Acad Sci USA 97:371-376 (2000).
Small, In: *Handbook of Lipid Research*, Plenum, 4:43-87 and 89-96.
Stacey "Macrophages ingest and are activated by bacterial DNA" J Immunol 157:2116-2122 (1996).
Steinman "Dendritic cells in the T-cell areas of lymphoid organs" Immunol Rev 156:25-37 (1997).
Stingl "The immune functions of epidermal cells" Immunol Ser 46:3-72 (1989).
Strange et al. "Staphylococcal Enterotoxin B Applied on Intact Normal and Intact Atopic Skin Induces Dermatitis" Arch. Dermatol. 132: 27-33 (1996).
Suzuki "Imiquimod, a topical immune response modifier, induces migration of Langerhans cells" J Invest Dermatol 114:135-141 (2000).
Takigawa "Percutaneous peptide immunization via corneum barrier-disrupted murine skin for experimental tumor immunoprophylaxis" Ann NY Acad Sci 941:139-146 (2001).
"Tuberculin, Purified Protein Derivative, Tine Test" Physician's Desk Reference, 3 pages (2002).
Udey "Cadherins and Langerhans cell immunobiology" Clin Exp Immunol 107 suppl 1:6-8 (1997).
Vassell "Activation of Langerhans cells following transcutaenous immunization" 13 FASEB J A633 482.8 (1999).
Verma "Phagocytosis of liposomes by macrophages: intracellular fate of liposomal malaria antigen" Biochim Biophys Acta 1066:229-238 (1991).
Verma "Adjuvant effects of liposomes containing lipid A: enhancement of liposomal antigen presentation and recruitment of macrophages" Infect Immun 60:2438-2444 (1992).
Vutla "Transdermal iontophoretic delivery of enkephalin formulated in liposomes" J Pharm Sci 85:5-8 (1996).
Walker "The role of percutaneous penetration enhancers" Adv Drug Delivery Rev 18:295-301 (1996).
Wang "Induction of protective polyclonal antibodies by immunization with a *Plasmodium yoelii* circumsporozite protein multiple antigen peptide vaccine" J Immunol 154:2784-2793 (1995).
Wang "Epicutaneous exposure of protein antigen induces a predominant Th2-like response with high IgE production in mice" J Immunol 156:4077-4082 (1996).
Wassef "Liposomes as carriers for vaccines" Immunomethods 4:217-222 (1994).
Watabe "Protection against influenza virus challenge by topical application of influenza DNA vaccine" Vaccine 19:4434-4444 (2001).
Weiner "Topical delivery of liposomally encapsulated interferon evaluated in a cutaneous herpes guinea pig model" Antimicrob Agents Chemotherap 33:1217-1221 (1989).

(56) References Cited

OTHER PUBLICATIONS

White "Induction of cytolytic and antibody responses using *Plasmodium falciparum* repeatless circumsporozoite protein encapsulated in liposomes" Vaccine 11:1341-1346 (1993).

White "Antibody and cytotoxic T-lympocyte responses to a single liposome associated peptide antigen" Vaccine 13:1111-1122 (1995).

Yasutomi "A vaccine-elicited, single viral epitope-specific cytotoxic T lymphocyte response does not protect against intravenous, cell-free simian immunodeficiency virus challenge" J Virol 69:2279-2284 (1995).

Zellmer "Interaction of phosphatidylcholine liposomes with the human stratum corneum" Biochim Biophys Acta 1237:176-182 (1995).

Kenney et al. "Induction of Protective Immunity against Lethal Anthrax Challenge with a Patch"; JID 2004, v. 190, p. 774-782.

Strid et al. "Disruption of the stratum corneum allows potent epicutaneous immunization with protein antigens resulting in a dominant system Th2 response" Eur. J. Immunol 2004; 34: 2100-2109.
Zhu et al. "Protection against Shig Toxin-Producing *Escherichia coli* Infection by Transcutaneous Immuniation with Shiga Toxin Subunit B"; Clinical and Vaccine Immunology 2008; v. 15(2): 359-366.
Frerichs et al., Controlled, single-step, stratum corneum disruption as a pretreatment for immunization via a patch. Vaccine. May 23, 2008;26(22):2782-7. Epub Mar. 28, 2008.
Frolov et al. (2008) Transcutaneous delivery and thermostability of a dry trivalent inactivated influenza vaccine patch. Influenza and Other Respiratory Viruses Doi: 10.1111/j.1750-2659.2008.00040.x. pp. 1-8.
Look et al., The Adjuvant Patch: A universal dose sparing approach for pandemic and conventional vaccine. BioPharm International. Aug. 2, 2007; 8 pages. http://www.biopharminternational.com/biopharm/article/articleDetail.jsp?id=444989 [last accessed Jan. 1, 2013].
Declaration of Robert Seid, signed May 2, 2007 and filed on May 3, 2007 in U.S. Appl. No. 10/633,626.

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: CTL Peptide

<400> SEQUENCE: 1

Ser Ile Asn Phe Glu Lys Lys Leu
1               5

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2
tccaatgagc ttcctgagtc t                                                    21

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
tccatgacgt tcctgacgtt                                                      20
```

TRANSCUTANEOUS IMMUNIZATION WITHOUT HETEROLOGOUS ADJUVANT

DESCRIPTION OF RELATED APPLICATIONS

This application is a continuation of U.S. application Ser. No. 11/141,690, filed on Jun. 1, 2005, which is a continuation of U.S. application Ser. No. 09/337,746 filed on Jun. 22, 1999, which claims the benefit under 35 U.S.C. §119(e) of U.S. Application No. 60/090,169, filed on Jun. 22, 1998, each of which is incorporated herein by reference in their entirety.

BACKGROUND OF THE INVENTION

1. Field of the Invention

The invention relates to human and animal health and, in particular, vaccines and their use to immunize humans and animals through an epicutaneous route of administration. Monovalent and multivalent vaccines with one or more immunogenic epitopes are provided which are capable of inducing an immune response when administered epicutaneously without addition of a separate adjuvant (i.e., a heterologous adjuvant).

2. Description of the Related Art

Skin, the largest human organ, is an important part of the body's defense against invasion by infectious agents and contact with noxious substances (see Bos, 1997a). The skin, however, may also be a target of chronic infections where organisms establish their presence through avoidance of the immune system.

The skin is composed of three layers: the epidermis, the dermis, and subcutaneous fat. The epidermis is composed of the basal, the spinous, the granular, and the cornified layers; the stratum corneum comprises the cornified layer and lipid (Moschella and Hurley, 1992). The principal antigen presenting cells of the skin, Langerhans cells, are reported to be in the mid to upper spinous layers of the epidermis in humans. The dermis contains primarily connective tissue. Blood vessels and lymphatics are believed to be confined to the dermis and subcutaneous fat.

The stratum corneum, a layer of dead skin cells and lipids, has traditionally been viewed as a barrier to the hostile world, excluding organisms and noxious substances from the viable cells below the stratum corneum (Bos, 1997a). The secondary protection provided by skin antigen presenting cells such as Langerhans cells has only recently been recognized (Celluzzi and Falo, 1997). Moreover, the ability to immunize through the skin using the crucial concept of a skin-active adjuvant has only been recently described (Glenn et al., 1998a). Scientific recognition of this important advance in vaccination was prompt. "It's a very surprising result, and it's lovely," said vaccine expert Barry Bloom of the Howard Hughes Medical Institute and the Albert Einstein College of Medicine in New York, the strategy sounds "very easy, very safe, and certainly inexpensive" (CNN News, Feb. 26, 1998).

*Vibrio cholera* secretes cholera toxin (CT) and enterotoxogenic *E. coli* (ETEC) secretes heat-labile enterotoxin (LT). These homologous proteins cause intestinal fluid secretion and massive diarrhea (Spangler, 1992), and are viewed as dangerous toxins.

*Vibrio cholera* and cholera toxin (CT) derived therefrom are examples of infectious agents and noxious bacterial products, respectively, which one would have expected the skin to protect against. Craig (1965) reported that stool filtrates of cholera patients injected intracutaneously into rabbits or guinea pigs produced a characteristic delayed onset, sustained edematous induration (i.e., swelling) which was induced by the presence of toxin in the skin. The swelling and vascular leakage was so dramatic that it was ascribed to an unknown permeability factor which was later shown to be CT itself. The Craig test became a standard assay for the presence and amount of CT in stool filtrates and culture media. Datta confirmed that this skin reactivity was due to cholera toxin (see Finkelstein and LoSpallutto, 1969). Thus, one could have reasonably expected that CT would be extremely reactogenic when placed on the skin or inserted through the stratum corneum, and would cause similar redness and swelling.

Craig (1965) cautioned, "The absence of skin lesions in clinical cholera certainly does not preclude the possibility that the noxa responsible for gut damage could also have a deleterious effect upon the skin provided it is applied to skin in sufficient concentration." The extreme reactogenicity of cholera toxin in the skin was used as a test for its toxicity and such prior art evidenced an expectation that cholera toxin would be reactogenic if applied to the skin, producing an undesirable reaction.

In contrast, we have shown cholera toxin to be immunogenic, acting as both antigen and adjuvant, when placed on the skin but without any resulting local or systemic side effects. This lack of reactogenicity when cholera toxin was placed on the skin for transcutaneous immunization was surprising and contradicted conclusions one would have drawn from the prior art. A liquid formulation of CT placed on the skin acted as a non-toxic, non-reactogenic adjuvant, in contrast to the expectations of Craig, while injection of CT into the skin results in swelling and redness. Thus, it was not obvious prior to our invention that cholera toxin or other ADP-ribosylating exotoxins would be useful for transcutaneous immunization. See our U.S. application Ser. Nos. 08/896,085 and 09/311,720; U.S. Pat. No. 5,910,306.

This expection that cholera toxin or other adjuvants would be highly reactogenic when placed on the skin was further supported by findings using the prototypical adjuvant, Freund's adjuvant. Kleinau et al. (1994) found that topical administration of incomplete Freund's adjuvant on the skin of rats induced arthritis as evidenced clinically and by proliferation of the joint lining, inflammatory infiltrates, and bone and cartilage destruction. They further stated, "This investigation has focused on the arthritogenic role of mineral oil, a prototype for an immunological adjuvant. It is plausible, however, that a number of other compounds with adjuvant properties may also have the same effect when applied percutaneously (sic)." In contrast to this suggestion, we have used a water-in-oil emulsion of a skin-active adjuvant (LT) and found that it safely induced an immune response without any systemic effects. See our U.S. application Ser. Nos. 08/896,085 and 09/311,720. Thus, it would have been expected that transcutaneous application of adjuvant, and especially an adjuvant in an emulsion, would have produced arthritis from this animal model. Our findings, however, unexpectedly showed that such formulations are devoid of reactogenicity.

Transcutaneous immunization requires both passage of an antigen through the outer barriers of the skin, which was thought to be impervious to such passage, and an immune response to the antigen. Fisher's *Contact Dermatitis* states that molecules of greater than 500 daltons cannot normally pass through the skin. Moreover, according to Hurley, "Skin owes its durability to the dermis, but its chemical impermeability resides in the epidermis and almost exclusively in its dead outer layer, the stratum corneum."

Skin reactions such as allergic or atopic dermatitis are known, but induction of a systemic immune response which elicits antigen-specific immune effectors and provides a therapeutic advantage by simple application of immunogen to skin does not appear to have been taught or suggested prior to our invention.

Generally skin antigen presenting cells (APCs), and particularly Langerhans cells, are targets of sensitization agents which result in pathologies that include contact dermatitis, atopic dermatitis, eczema, and psoriasis. Contact dermatitis may be directed by Langerhans cells which phagocytize antigen, migrate to the lymph nodes, present antigen, and sensitize T cells for the intense destructive cellular response that occurs at the affected skin site (Kripke et al., 1990). An example of atopic dermatitis is a chronic relapsing inflammatory skin disease associated with colonization of the skin with *S. aureus* and thought to be caused by *S. aureus*-derived superantigens that trigger chronic T-cell mediated skin inflammation through Langerhans cells (Herz et al., 1998; Leung, 1995; Saloga et al., 1996a). Atopic dermatitis may utilize the Langerhans cells in a similar fashion to contact dermatitis, but is identified by its inflammatory skin manifestations and the presence of Th2 cells as well as being generally associated with high levels of IgE antibody (Wang et al., 1996a).

In contrast, transcutaneous immunization with cholera toxin or related ADP-ribosylating exotoxins resulted in a novel immune response with an absence of post-immunization skin findings, high levels of antigen-specific IgG antibody, the presence of all IgG subclass antibodies, and the absence of antigen-specific IgE antibody. See our U.S. application Ser. Nos. 08/896,085 and 09/311,720; U.S. Pat. No. 5,910,306.

There is a report by Paul et al. (1995) of induction of complement-mediated lysis of antigen-sensitized liposomes using transfemsomes. The transferosomes were used as a vehicle for antigen, and complement-mediated lysis of antigen-sensitized liposomes was assayed. The limit to passage through the skin by antigen was stated to be 750 daltons. Furthermore, Paul and Cevc (1995) stated that it is "impossible to immunize epicutaneously with simple peptide or protein solutions." Thus, transcutaneous immunization as described herein would not be expected to occur according to this group.

Besides the physical restriction of limiting passage through the skin of low molecular weight, passage of polypeptides was believed to be limited by chemical restrictions. Carson et al. (U.S. Pat. No. 5,679,647) stated that "it is believed that the bioavailability of peptides following transdermal or mucosal transmission is limited by the relatively high concentration of proteases in these tissues. Yet unfortunately, reliable means of delivering peptides . . . by transdermal or mucosal transmission of genes encoding for them has been unavailable."

In contrast to transcutaneous immunization, transdermal drug therapy has been understood to target the vasculature found in the dermis. For example, Moschella (1996) states, "The advantages of transdermal therapy over conventional oral administration include: 1. Avoidance of 'peak and trough' plasma concentration profiles. 2. Avoidance of first-pass metabolism in the gastrointestinal tract and liver" (emphasis added). Thus, in the realm of drug delivery, the meaning of transdermal is to pass through the epidermis and into the dermis or lower layers to achieve adsorbtion into the vasculature.

In many cases, effective immunization that leads to protection requires help in the form of adjuvants for the co-administered antigen or plasmid and, therefore, protective immune responses might require the use of an adjuvant to enhance the immune response (Stoute et al., 1997; Sasaki et al., 1998). In our U.S. application Ser. No. 09/311,720, a skin-active adjuvant was required to induce high levels of systemic and mucosal antibodies to co-administered antigens. For example, mice immunized with CT+DT induced high levels of systemic and mucosal anti-DT antibodies. Antibodies are known to correlate with protection against diphtheria. Thus, the skin-active adjuvant for transcutaneous immunization can be expected to provide 'help' in the immune response to co-administered antigen and to play a critical role in inducing a useful immune response.

Such references explain why our successful use of a molecule like cholera toxin (which is 85,000 daltons) as an antigen-adjuvant in immunization was greeted with enthusiasm and surprise by the art because such large molecules were not expected to pass through the skin and, therefore, would not have been expected to induce a strong, specific immune response.

Our U.S. application Ser. Nos. 08/749,164 (now U.S. Pat. No. 5,910,164), 08/896,085, and 09/311,720 show that using a wide variety of ADP-ribosylating exotoxins such as, for example, cholera toxin (CT), heat-labile enterotoxin from *E. coli* (LT), *Pseudomonas* exotoxin A (ETA), and pertussis toxin (PT), can elicit a vigorous immune response to epicutaneous application which is highly reproducible. Moreover, when such skin-active adjuvants were applied along with a separate antigen (e.g., bovine serum albumin or diphtheria toxoid), systemic and mucosal antigen-specific immune responses could be elicited.

Thus bovine serum albumin (BSA), not highly immunogenic by itself when epicutaneously applied to the skin, can induce a strong immune response when placed on the skin with CT. The Langerhans cell population underlying the site of application are a preferred antigen presenting cell (APC) for activation, differentiation, and delivering antigen to the immune system. Adjuvant may act on the APC directly, or through cognate lymphocytes specifically recognizing antigen. The induction of mucosal immunity and immunoprotection with the present invention would not have been expected by the art prior to the cited disclosures.

Furthermore, our U.S. application Ser. Nos. 09/257,188, 60/128,370, and 09/309,881 disclose penetration enhancers (e.g., removal of superficial layers above the dermis, micropenetration to above the dermis), dry formulations, and targeting of complexed antigen in the context of transcutaneous immunization, respectively.

SUMMARY OF THE INVENTION

An object of the invention is to provide an improved system for immunization of an organism in need of such treatment. Transcutaneous immunization can involve simple epicutaneous application of a formulation comprised of at least one antigen, polynucleotide encoding antigen, both antigen and polynucleotide, or combinations of more than one different antigens and/or polynucleotides to induce an immune response specific for that antigen. The antigen may have at least one epitope which is immunogenic enough to induce an immune response without the need for an adjuvant, or the antigen or polynucleotide encoding antigen may include a non-heterologous portion with adjuvant activity.

The immune response can be enhanced by hydration of the site where the formulation is applied, superficial penetration or micropenetration at that site, use of liquid or dry formulations, formation of complexes between or among components of the formulation to target at least one active component of the formulation to an antigen presenting cell, or the addition of other physical manipulations during immunization or chemical additives to the formulation. But such enhancement is not necessarily required to evoke a useful antigen-specific immune response, just as use of heterologous adjuvant is not necessarily required.

This delivery system provides simple application of a formulation comprised of at least one antigen, or of at least one polynucleotide encoding antigen, to intact skin of an organism which induces at least a specific response against the antigen by the organism's immune system. The only required active ingredient in such a formulation is the antigen or the polynucleotide encoding antigen. Thus, an antigen-only formulation may be used for transcutaneous immunization (e.g., influenza hemagglutinin or nucleoprotein, bacterial ADP-ribosylating exotoxins or toxoid, and lipopolysaccharides).

Addition of an endosomolytic agent (e.g., hemagglutinin or a fusogenic fragment thereof) to disrupt the endosome-lysosome pathway of cellular transport, a virus (e.g., an adenovirus or components thereof) which uses that pathway for infection, or a chemical transfection agent (e.g., polyethyleneimine) is preferred. Without being committed to any particular mechanism of action, this may affect the transport pathway of an antigen presenting cell (APC) to achieve an increase in activation of the APC and/or antigen presentation by the APC. Such an improvement may provide an immunologic benefit to the organism in need of treatment as compared to transcutaneous immunization without lysis of at least some endosomes or lysosomes. The endosomolytic agent may be added in a complex with antigen and/or polynucleotide in the formulation.

It is a particular object of the invention for transcutaneous immunization to provide a protective immune response for prophylactic or therapeutic treatment. Such responses include vaccination that protects against subsequent antigenic challenge or pathogenic infection, or a reduction in the number and/or severity of symptoms that are associated with a disease or other pathologic disorder.

In particular, the invention may promote contact between antigen and immune cells. For example, contacting antigen presenting cells (e.g., Langerhans cells, dermal dendritic cells, dendritic cells, follicular dendritic cells, B cells, macrophages) with antigen and/or polynucleotide may enhance activation of the antigen presenting cell and/or presentation of antigen. The antigen presenting cell could then present the antigen to a lymphocyte. In particular, the antigen presenting cell may migrate from the skin to the lymph nodes, and then present antigen to a lymphocyte, thereby inducing an antigen-specific immune response. Moreover, the formulation may directly contact a lymphocyte which recognizes antigen, thereby inducing an antigen-specific immune response.

In addition to eliciting immune reactions leading to activation and/or expansion of an antigen-specific B and/or T cell population, including a cytotoxic T lymphocyte (CTL), another object of the invention is to positively and/or negatively regulate components of the immune system by using the transcutaneous immunization system to affect antigen-specific helper (Th1 and/or Th2) or delayed-type hypersensitivity (DTH) T-cell subsets. The desired immune response is preferably systemic or regional (e.g., mucosal), but it is preferably not an allergic reaction, dermatitis, eczema, psoriasis, or other atopic skin reaction.

The invention may be practiced without perforation of the intact skin. But the invention may also include applying the formulation to skin with physical energy, electrical energy, sonic energy, or combinations thereof used to perforate the stratum corneum to reach the outer layer of the epidermis. Optionally, the formulation may include chemical penetration enhancers, viral particles, whole or intact cells, liposomes, proteosomes, chemical transfectants, materials to promote skin hydration, or combinations thereof. Hydrating the skin at the application site, increasing the local concentration, or recruiting antigen presenting cells to the application site may enhance the immune response.

A preferred embodiment of the formulation is to provide a single or unit dose for administration. This may simplify administration of the formulation to the subject, each unit dose containing active ingredients in pre-determined amounts for a single round of immunization. The amount of antigen or polynucleotide encoding antigen in the unit dose may be anywhere in a broad range from about 0.1 µg to about 10 mg. The range from about 1 µg to about 1 mg is preferred, the range from about 10 µg to about 500 µg is more preferred. Other suitable ranges are between about 1 µg and about 10 µg, between about 10 µg and about 50 µg, between about 50 µg and about 200 µg, and between about 1 mg and about 5 mg.

In contrast to the expectations of the art, our delivery system provided by transcutaneous immunization is capable of achieving efficient delivery of at least antigen and/or polynucleotide encoding antigen through the skin to the immune system.

DESCRIPTION OF PREFERRED EMBODIMENTS

Figure 1:
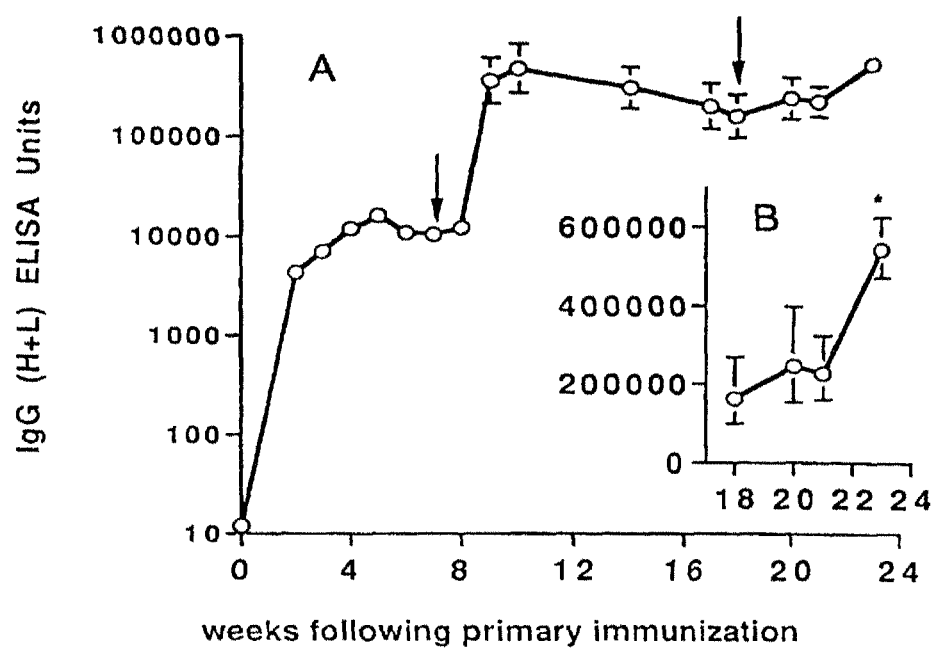
FIG. 1, panels A-B, shows the CT-specific antibody responses in BALB/c mice immunized transcutaneously with cholera toxin (CT). The ordinate of panel A is exponentially scaled and arrows indicate the 8 and 18 week time points. Panel B displays the antibody titers induced after the 18 week boost on a linear scale. An asterisk (*) denotes a statistically significant increase ($p<0.05$) in anti-CT antibody titer between 18 and 23 weeks.

The transcutaneous immunization system of the present invention can deliver antigen to the immune system through the stratum corneum without physical or chemical penetration to the dermis layer of the skin. This delivery system induces an antigen-specific immune response. Although perforation of intact skin is not required, superficial penetration or micropenetration of the skin can act as an enhancer. Similarly, hydration may enhance the immune response. This system can induce antigen-specific immune effectors after epicutaneous application of a formulation containing one or more active ingredients (e.g., antigen, polynucleotide encoding antigen).

The formulation may initiate and/or enhance processes such as antigen uptake, processing, and presentation; Langerhans cell activation, migration from the skin to other immune organs, and differentiation to mature dendritic cells; contacting antigen with lymphocytes bearing cognate antigen receptors on the cell surface and their stimulation; and combinations thereof.

Systemic and/or regional immunity may be induced. Immune responses that result in prophylactic and/or therapeutic treatments are preferred. Antigen activities in the formulation may be found in the same molecule, two or more different molecules dissociated from each other, or multiple molecules in a complex formed by covalent or non-covalent bonds. For antigens which are proteinaceous, they may be provided in the formulation as a polynucleotide for transcutaneous genetic immunization. Besides simple application of a dry or liquid formulation, patches or other medical devices may be used to deliver antigen for immunization.

In a first embodiment of the present invention, a formulation containing only one or more antigens or polynucleotides encoding antigen as active ingredients is applied to intact skin of an organism, antigen is presented to immune cells, and an antigen-specific immune response is induced without perforating the skin. As noted above, transcutaneous immunization may also be practiced with physical and/or chemical penetration enhancers.

The formulation may include an additional active ingredient (e.g., antigen, polynucleotide encoding antigen) such that application of the formulation induces an immune response to both the organism and the applied antigen or multiple antigens. In such a case, the antigens may or may not be derived from the same source, but the antigens will have different chemical structures so as to induce immune responses specific for the different antigens. Antigen-specific lymphocytes may participate in the immune response and, in the case of participation by B lymphocytes, antigen-specific antibodies may be part of the immune response. A patch containing antigen and/or polynucleotide encoding antigen may contain a single reservoir or multiple reservoirs with individual antigens and/or polynucleotides encoding antigen.

The application site may be further manipulated with anti-inflammatory corticosteroids (e.g., hydrocortisone, triamcinolone, mometazone) or non-steroidal anti-inflammatory drugs (NSAIDs) to reduce possible local skin reaction or modulate the type of immune response. Similarly, anti-inflammatory steroids, NSAIDs, chemokines, cytokines, or other inflammatory agents or immunomodulators may be included in the patch material or formulations, or may be applied after immunization to alleviate any potential symptoms cause by the transcutaneous immunization.

Another object of the invention is to provide formulations useful for human or animal immunization, as well as processes for their manufacture. Although liquid formulations are conveniently used under controlled conditions, a dry formulation is more easily stored and transported than conventional vaccines, it breaks the cold chain required from the vaccine's place of manufacture to the locale where vaccination occurs. Without being limited to any particular mode of action, another way in which a dry formulation may be an improvement over liquid formulations is that high concentrations of an active component of the formulation may be achieved by solubilization directly at the site of immunization over a short time span. Moisture from the skin and an occlusive dressing may hasten this process. In this way, it is possible that a concentration approaching the solubility limit of the active component may be achieved in situ. Alternatively, the dry active component of the formulation per se may be the improvement by providing a solid particulate form that is taken up and processed by antigen presenting cells. These possible mechanisms are discussed not to limit the scope of the invention or its equivalents, but to provide insight into the present invention's possible modes of operation and to guide the use of this formulation in immunization.

The dry formulation of the invention is provided in various forms. A "patch" refers to a preferred embodiment which includes a solid substrate (e.g., medical dressing) as well as at least one active component. Other embodiments are fine or granulated powders, dry films, pellets, and tablets. The formulation may be dissolved, and then dried in an ampoule or on a flat surface (e.g., skin), or simply dusted on the flat surface. It may be air dried, dried with elevated temperature, dried as a mist or spray, freeze dried as a mist or spray, coated or sprayed on a solid substrate and then dried, dusted on a solid substrate, quick frozen and then slowly dried under vacuum, or combinations thereof. If different molecules are active components of the formulation, they may be mixed in solution and then dried, or mixed in dry form only. Compartments or chambers of the patch may be used to separate active components so that only one of the antigens or polynucleotides is kept in dry form prior to administration. Separating liquid and solid ingredients in this manner allows control over the time and rate of the dissolving of at least one dry active component. Optionally the formulation may include at least one excipient or stabilizer. The formulation may be manufactured under aseptic conditions with practices acceptable to the appropriate regulatory agencies (e.g., the Food and Drug Administration) for biologicals and vaccines.

In another embodiment, the present invention is used to treat an organism in need of such treatment. If the antigen is derived from a pathogen, the treatment may vaccinate the organism against infection by the pathogen or against its pathogenic effects such as those caused by toxin secretion. The specific ligand-receptor interactions that pathogens use to infect a cell are a preferred source of antigen (e.g., surface antigens, virulence or colonization factors, other components of the pathogen's coat or cell surface). A formulation that includes a tumor antigen may provide a cancer treatment; a formulation that includes an autoantigen may provide a treatment for a disease caused by the organism's own immune system (i.e., autoimmune disease); a formulation that includes an allergen may provide a treatment for allergy or other hypersensitivity reactions. The present invention may be used therapeutically to treat existing disease, prophylactically to prevent disease, or to reduce the severity and/or duration of disease.

Ligand-receptor interactions that are specific for antigen presenting cells (APCs), especially Langerhans cells and other dendritic APCs, are preferred because this would target the antigen presenting cells of interest by conjugation of the antigen and/or polynucleotide encoding the antigen to a member of the specific binding complex (i.e., any component of the binding complex on the cell surface of the antigen presenting cell), or a derivative thereof that retains this specific binding function (e.g., a soluble version of a membrane-bound receptor on the surface of a cell binding to the APC which is considered to be the "ligand" binding to the antigen presenting cell). Preferred are two component binding to the cell surface of the APC (i.e., a specific binding pair) or situations where a simple polypeptide, lipid, or carbohydrate moiety is involved in specific binding to a receptor complex on the cell surface of the APC because this can simplify the conjugate component of the formulation to a single molecule. The non-APC member of the specific binding pair or the ligand moiety may be included as a component of the conjugate, covalently or non-covalently, and specific binding of the complex to the antigen presenting cell would be likely.

Langerhans cells have on their surface immunoglobulin receptors (Fc receptors) (Stingl et al., 1977) and complement receptors such as those for C3b (Karp et al., 1996; Hammerberg et al., 1998) which function to enhance the targeting of antigens to the APC (e.g., Langerhans cells in the epidermis, dermal dendritic cells, dendritic cells, follicular dendritic cells, macrophages) and/or induce the antigen presenting cell to then present the antigen to a lymphocyte. In particular, once the APC is targeted with antigen complexed with immunoglobulin or complement, the antigen presenting cell may migrate from the skin to the lymph nodes, and then present antigen to a lymphocyte, thereby inducing an antigen-specific immune response.

Other ligand-receptor interactions may be targeted as well. Presentation of antigen in the context of CD1 involves uptake of glycolipids by APC mannose receptors and the delivery to endosomal compartments where loading of lipid antigen is thought to take place (Castano et al., 1995; Prigozy et al., 1997; Zeng et al., 1997; Sieling et al., 1999). Mannose receptors may allow targeting of antigen and/or polynucleotide, thereby confer the advantages of presentation in the context of CD1, especially because this molecule in a non-polymorphic antigen presenting molecule. Heterologous molecules that bind carbohydrates (e.g., lectins) could target complex sugars on the surface of APCs; glycosylated heterologous molecules can target carbohydrate-binding receptors on the surface of APCs.

If both peptide and non-peptide antigens could target CD1 molecules, then genetic major histocompatibility complex (MHC) restrictions of the immune response to antigens may be overcome. This is in addition to the aforementioned advantages of specific targeting of antigen presenting cells. Mannose receptors may be used other antigens such as whole viruses or proteins (Grosjean et al., 1997; Castano et al., 1995).

Receptors such as the flt3 receptor may also be used to target Langehans cells or increase their numbers (Strobl et al., 1997). Other ligand-receptor interactions that may be targeted include CD101 (Bagot et al., 1997), CD40 (Hammerberg et al., 1998), DEC 205 (Inaba et al., 1995), high affinity IgE Fc receptors (Jurgens et al., 1995), GM-CSF receptors (Emile et al., 1995), TNFα receptors (Wang et al., 1996b), CD68 (Furue et al., 1995), CD48 (Ozaea et al., 1995), C5a (CD88) (Morrelli et al., 1996, 1997), glucocorticoid receptor (Serres et al., 1996), and gastrin-releasing peptide (Staniek et al., 1996). Other cell surface markers for Langerhans cells are described in "Langerhans Cells and Related Skin Dendritic Cells" (Bos, 1997b).

In yet another embodiment of the present invention, ligand-receptor interactions could be used in combination to enhance the immune response of antigen presenting cells (APCs) in the skin. For example, pretreatment of the skin with GM-CSF or a subunit thereof or recombinant which binds to APCs in the skin can upregulate C5a receptors (Morrelli et al., 1996). Antigen and/or polynucleotide complexed to C5a could then be added to augment their targeting to APCs.

Antigen and/or polynucleotide encoding antigen may be complexed with alpha-2 macroglobulin to form a complex which is thought to enhance receptor-mediated endocytosis (Mitsuda et al., 1995). CD91 is a receptor for alpha-2 macroglobulin on antigen presenting cells. Thus, alpha-2 macroglobulin targets an antigen presenting cell and may even be used to load peptide in the major histocompatibility complex (MHC) class II molecule without further antigen processing.

Complexes may also include an agent that lyses endosomes and/or lysosomes, especially of antigen presenting cells. For example, antigen and/or polynucleotide encoding antigen may be simply admixed with split virus from influenza which contains factors such as hemagglutinin (HA) or other agents which have endosomolytic activity. This may affect protein transport (retrograde and/or anterograde) through the endosome-lysosome pathway and thus change degradative processes involved in antigen presentation or transfection of polynucleotides. Additionally, HA may act as an adjuvant to enhance the immune response and may activate antigen presenting cells (e.g., Langerhans cells) to migrate out of the skin and present antigen in lymph nodes. Such a formulation could include coat protein, other viral components, or whole virus to enhance the CTL response which is thought to require cytoplasmic antigen for efficient production of CTLs.

A formulation containing antigen and/or polynucleotide encoding antigen and targeting agent is complexed (e.g., mixed, covalently or non-covalently bound) with or without an endosomolytic agent and applied to the skin of an organism. Induction of an antigen-specific immune response may be improved thereby with greater immunologic benefit as compared to a formulation without the complex and/or endosomolytic agent.

In a second embodiment of the present invention, a patch for use in the above methods is provided. The patch may comprise a dressing, and an effective amount of antigen and/or polynucleotide. Active components may be provided in liquid and/or dry forms. They may be present in a complex that targets Langerhans cells or other antigen presenting cells. The patch may contain a physical or chemical component that enhances the immune response through penetration enhancement. See U.S. Pat. Nos. 3,734,097, 4,915,950, and 5,049,387 for detailed descriptions of patches.

Suitable patch materials include cellulose (e.g., rayon); cotton; metals; acrylics, alkyds, epoxys, polyamides, polycarbonates, polyesters, polyethylenes, polypropylenes, polystyrenes, urethanes, vinyl polymers, other plastics; resins; rubber and elastomers; silicones, and combinations thereof. The patch material may be occlusive or non-occlusive, woven or non-woven. Such patches can be provided with an adhesive or non-adhesive backing which is biocompatible, and preferably moisture resistant and/or easily removable. Suitable backing materials include acrylates, cellulose acetate, epoxy resins, gums, rubber latex, silicone, sodium silicates, and combinations thereof. Patches with a non-adhesive backing can be secured to the organism by non-adhesive means such as, for example, wrapping. Durable parts of the patch may be metallic or plastic to maintain fluid impermeability and to keep separate liquids in different compartments.

The patch may include additional antigens such that application of the patch induces an immune response to multiple antigens. In such a case, the antigens may or may not be derived from the same source, but the antigens will have different chemical structures so as to induce an immune response specific for the different antigens. Multiple patches may be applied simultaneously; a single patch may contain multiple reservoirs. For effective treatment, multiple patches may be applied at frequent intervals or constantly over a period of time, or may be applied simultaneously. The patch may include a controlled released reservoir or matrix or rate controlling membrane may be used which allows time release of antigen and/or polynucleotide. The patch may contain a single reservoir or multiple reservoirs with individual antigens and/or polynucleotides. Complex formation may be regulated by mixing of these reagents according to the accessibility of the reservoir, matrix, or membrane such that the complex is formed just prior to and/or during application of the patch to the skin of the organism.

Creams, emulsions, gels, lotions, ointments, pastes, solutions, suspensions, and other vehicles may be applied in a similar fashion using multiple antigens, polynucleotides both at the same and separate sites or simultaneously or in frequent repeated applications. Solutions may also be applied by bathing or immersing, rubbing or massaging, painting, spraying, and wetting or wiping.

In another embodiment of the present invention, the formulation may be applied to the skin overlying more than one draining lymph node field using either single or multiple applications. The formulation may include additional antigens such that application to the skin induces an immune response to multiple antigens. In such cases, the antigens may or may not be derived from the same source, but the antigens will have different chemical structures and induce an immune response specific for the different antigens.

The formulation may be applied to intact skin to boost or prime the immune response in conjunction with other routes of immunization. Thus, priming with transcutaneous immunization with either single or multiple applications may be followed with oral, nasal, or parenteral techniques for boosting immunization with the same or altered antigens. The formulation may include additional antigens such that application to intact skin induces an immune response to multiple antigens.

In addition to antigen and/or polynucleotide encoding antigen, the formulation may comprise a liquid vehicle or particulate carrier. For example, the formulation may comprise emulsions like aqueous creams, microemulsions, oil-in-water (O/W) emulsions like oily creams, anhydrous lipids, fats, waxes, oils, silicones, polymers, copolymers, humectants like glycerol, moisturizers, and other chemicals that promote hydration. A solid microparticle (e.g., tungsten, gold, colloidal metals) may carry antigen and/or polynucleotide on its surface while a biodegradable particle (e.g., polylactides, polyglycolides, copolymers thereof, polycaprolactones) may release its contents at a particular time and place.

The antigen may be derived from a pathogen that can infect the organism (e.g., bacterium, virus, fungus, or parasite), or a cell (e.g., tumor cell or normal cell). The antigen may be a tumor antigen or an autoantigen (insulin A chain, insulin B chain, p9-23, panreatic islet antigens, glutamate dehydrogenase, GAD 65; Ramiya et al., 1997). The antigen may be an allergen such as pollen, animal dander, mold, dust mite, flea allergen, salivary allergen, grass, food (e.g., peanuts and other nuts), Bet v 1 (Wiedermann et al., 1998), or even a contact sensitizer like nickel or DNCB. Chemically, the antigen may be a carbohydrate, glycolipid, glycoprotein, lipid, lipoprotein, phospholipid, polypeptide, or chemical or recombinant conjugate of the above. The molecular weight of the antigen may be greater than 500 daltons, preferably greater than 800 or 1000 daltons, more preferably greater than 2500 or 5000 daltons, and even more preferably greater than 10,000 daltons.

Antigen may be obtained by recombinant means, chemical synthesis, or purification from a natural source. Preferred are proteinaceous antigen or conjugates with polysaccharide. Antigen may be at least partially purified in cell-free form (e.g., soluble or membrane fraction, whole cell lysate). Alternatively, antigen may be provided in the form of live, attenuated, inactivated, recombinant, and pathogenic forms of pathogens like bacteria, fungi, parasites, and viruses. Useful vaccine vectors are viruses (e.g., adenovirus, polio virus, poxviruses, vaccinia viruses) and bacteria, especially those that are harmless when colonizing humans.

Selection of suitable components of the formulation may allow preferential induction of a humoral and/or cellular immune response, specific antibody isotypes (e.g., IgM, IgD, IgA 1, IgA2, IgE, IgG1, IgG2, IgG3, and/or IgG4), and/or specific T-cell subsets (e.g., CTL, Th1, Th2 and/or $T_{DTH}$).

Optionally, antigen, heterologous polypeptide, polynucleotides encoding same, or combinations thereof may be provided in the formulation by means of a nucleic acid (e.g., DNA, RNA, cDNA, cRNA) encoding the polypeptide as appropriate. Subunits of the polynucleotide may be deoxyribonucleosides, ribonucleosides, non-natural analogs, or modified derivatives thereof (e.g., substitutions of the deoxyribose or ribose sugar). Linkages are conventionally phosphodiester bonds, but may involve some combination of nitrogen, oxygen, phosphorus, silicon, and sulfur heteroatoms (e.g., amide and phosphorothioate bonds). Polynucleotide may be chemically synthesized or purified from a host (e.g., bacterium, fungus, yeast, mammalian or insect cell). The polynucleotide may be single stranded or double stranded; preferably, it is in a covalently closed, circular form (e.g., plasmid). Replicating the polynucleotide in a bacterial host will remove the specific methylation pattern of CpG dinucleotides which is typical of higher eukaryotes like mammals. This technique is called "genetic immunization" in the art.

The term "antigen" as used in the invention, is meant to describe a substance that induces a specific immune response when presented to immune cells of an organism. An antigen may comprise a single immunogenic epitope, or a multiplicity of immunogenic epitopes recognized by a B-cell receptor (i.e., antibody on the membrane of the B cell) or a T-cell receptor. To be effective, the immune response induced by the antigen may only recognize a single epitope. As previously discussed, a molecule may be both an antigen and an adjuvant (e.g., cholera toxin). Thus, an antigen-only formulation according to the present invention may contain adjuvant activity (separable or non-separable) but it does not contain heterologous adjuvant that is not intended to be used as an antigen.

Bovine serum albumin (BSA) and the A subunit of cholera toxin (CTA) are examples of antigens that did not induce a detectable immune response. Soluble *leishmania* antigen (SLA) extract did not induce detectable antigen-specific antibodies (i.e., humoral immunity) but did induce antigen-specific lymphocytes (i.e., cellular immunity) without requiring heterologous adjuvant. Cholera toxin (CT), pertussis toxin (PT), *Pseudomonas* exotoxin A (ETA), *E. coli* heat-labile enterotoxin (LT), diphtheria toxin (DT), sequestrin, influenza hemagglutinin (HA) and nucleoprotein (NP), *Hemophilus influenza* B polysaccharide conjugate (Bib-PS), *E. coli* colonization factor CS6, tetanus fragment C (TetC), and ovalbumin (OVA) are other examples of antigens that induce a detectable immune response without a need to include heterologous adjuvant in the formulation.

The term "adjuvant" as used in the invention, is meant to describe a substance added to the formulation to assist in inducing an immune response to the antigen. Thus, an adjuvant may consist of an activator and/or growth-differentiation factor of antigen presenting cells, an inducer of antigen presentation, or combinations thereof. Adjuvants which are themselves antigenic would also be useful as antigen in the present invention.

The term "complex" as used in the invention, is meant to describe the conjugation of components of the formulation by covalent or non-covalent bonds, or some combination thereof. A covalent bond can be made by chemical cross-linkers or production of a fusion protein. Covalent conjugates may also be provides by a polynucleotide encoding a fusion protein. A non-covalent bond can be made by a specific interaction such as that involved in binding of, for example, antibody-Fc receptor, biotin-avidin (e.g., native avidin, streptavidin, NEUTRAVIDIN from Pierce, Rockford, Ill.), chelated $Ni^{++}$-polyhistidine, complement fragment-complement receptor, epitope-antibody, glutathione-glutathione S-transferase (GST), hapten-antibody (e.g., DNP, digoxygenin), lectin-carbohydrate, maltose binding protein (MBP)-simple or complex sugars (e.g., dextrin or other polysaccharides), protein A or G-antibody constant region, and other ligand-receptor interactions. Two-component interactions are preferred because either member of the specific binding pair may be incorporated into the complex. A heterologous molecule may be included in the complex as a component in a specific binding interaction to be involved in holding the complex together, to target the complex to an antigen presenting cell, or both.

Molecules may be biochemically modified by conjugation to a heterologous molecule (see aforementioned components of specific binding interactions), creation of reactive amine or thiol groups with a chemical cross-linker, removing or adding sugar residues, or cleavage with a protease under complete or limited digestion conditions. Stability of the complex during transcutaneous immunization, from application through delivery to an antigen presenting cell, during transit through the stratum corneum to the epidermis, and combinations thereof are preferred. Reducing the size of components, especially the heterologous molecule, is also preferred and is likely to be successful in many cases because fragments are known that retain their ability to specifically bind their cognate ligand: avidin, GST, MBP, complement, immunoglobulin, protein A, and soluble versions of membrane-bound proteins produced by deletion of a transmembrane domain.

Preferably, the heterologous molecule is involved in specific binding to the surface of an antigen presenting cell. Cell surface molecules found on Langerhans cells, and not other epidermal cells, are more preferred (see Bos, 1997b). Polypeptide fragments such as those from complement that bind to at least one of the antigen presenting cell's complement receptors or those from antibody that bind to at least one of the antigen presenting cell's Fc receptors may act to target the complex.

As used in the claims, "complex" may refer to all of its components or a portion thereof. Thus, the complex may be formed by a mixture of covalent and non-covalent bonds. It may contain conjugates that are covalently or non-covalently linked. Insoluble complexes or very large complexes may require physical or chemical penetration to induce an antigen-specific immune response. Preferably, the average molecular weight of the entire complex is greater than about 50,000 daltons; about 100,000 daltons; about 250,000 daltons; about 500,000 daltons; or about 1,000,000 daltons for a soluble complex. For example, IgG is about 154,000 daltons and pentameric IgM is about 900,000 daltons. Sizing may be performed by gel filtration or velocity sedimentation.

A "heterologous" molecule, polynucleotide, or polypeptide is not found naturally linked to the other component(s) of the complex. For example, a fusion protein may be provided by recombinant technology using a polynucleotide expressing antigen and heterologous polypeptide. The fusion protein may be produced by recombinant expression in a microbial host or by genetic immunization with the polynucleotide in the organism. A polynucleotide produced by recombinant technology (i.e., as opposed to natural recombination occurring during cell division and sexual reproduction) is also typically heterologous because the genes being recombined are obtained from different host sources or positions in the genome.

The term "effective amount" as used in the invention, is meant to describe that amount of antigen which induces an antigen-specific immune response. Such induction of an immune response may provide a treatment such as, for example, immunoprotection, desensitization, immunosuppression, modulation of autoimmune disease, potentiation of cancer immunosurveillance, or therapeutic vaccination against an established infectious disease. The amount used will ultimately be determined at the discretion of a physician or veterinarian to achieve a beneficial effect in the treated organism. For example, diseases or other pathologic conditions may be prevented or cured. It is sufficient, however, for the beneficial effect to be a reduction in the number or severity of symptoms associated with the disease or other pathologic condition. Such effects may be measured through objective criteria by the physician or veterinarian, or subjective self-reporting by the organism or observers familiar with the organism.

The precise measurements and criteria used may vary depending on factors such as the natural history of the disease or pathogenesis of the condition, clinical characteristics of the disease or pathologic condition, mechanism of disease or pathogenesis, standard medical or veterinary practice to treat the disease or pathologic condition, effectiveness of pre-existing immunization protocols, and availability of alternative treatments.

The clinical discretion of the physician or veterinarian may be influenced by the organism's sex, age, size, weight, medical history, diet, general health and immunologic status, sensitivity to allergens, susceptibility to pharmacologic interactions, and number and severity of symptoms. Taking all such factors into account, selection of organisms that will benefit from treatment, precise dosage amounts, timely dosing schedules, and the exact site of administration is a medical or veterinary judgment to be made in the best interests of the organism. For example, depending on the severity of the disease or condition and the availability of alternative treatments, it may be prudent to treat an organism according to the present invention even if the immune response is low and/or there are minor side effects.

The term "draining lymph node field" as used in the invention means an anatomic area over which the lymph collected is filtered through a set of defined set of lymph nodes (e.g., cervical, axillary, inguinal, epitrochelear, popliteal, those of the abdomen and thorax). The organism in need of treatment may be any organism with an immune system capable of inducing an antigen-specific immune response, humoral and/or cellular, such as mammals, birds, and fishes.

Of primary concern is the immunization of humans and animal models of human diseases and pathologic conditions (e.g., primates such as chimpanzee or rhesus monkey). Other laboratory animals such as lagomorphs and rodents (e.g., guinea pig, hamster, mouse, rabbit, rat) are standard models for the mammalian immune system. Companion animals such as dogs, cats, and other pets may also be treated. Domesticated animals important for agriculture include cattle, donkeys, goats, horses, mules, pigs, and sheep. Also of agricultural importance are domesticated birds raised on farms (e.g., chicken, duck, emu, ostrich, quail, and turkey) and fishes cultured in ponds (e.g., carp, catfish, salmon, tilapia). Wild or feral versions of the aforementioned may also be treated for conservation purposes or because they represent reservoirs for epidemics (e.g., influenza, Lyme disease, malaria, rabies).

Other such animals are bears, bison, buffalo, chipmunks, cougars, coyotes, deer, elks, foxes, jaguars, moose, racoons, squirrels, and wolves.

Without being bound to any particular theory but only to provide an explanation for our observations, it is presumed that the transcutaneous immunization delivery system carries antigen to cells of the immune system where an immune response is induced. The antigen may pass through the normal protective outer layers of the skin (i.e., stratum corneum) and induce the immune response directly, or through an antigen presenting cell (APC) population in the epidermis (e.g., macrophage, tissue macrophage, Langerhans cell, dendritic cell, dermal dendritic cell, B lymphocyte, or Kupffer cell) that presents processed antigen to a lymphocyte. Of course, this proposed mechanism is not intended to limit the claimed invention unless the specific limitation for an event that results in induction of the immune response are explicitly recited in the claim.

Optionally, the antigen may pass through the stratum corneum via a hair follicle or a skin organelle (e.g., sweat gland, oil gland). Thus, there may be an advantage to micropenetration of the skin (e.g., physical or chemical penetration through the stratum corneum) prior to and/or during immunization. Some advantages of targeting the APC in may be that the rate of assembling together antigen/polynucleotide and APC at a single site is accelerated, and/or the probability of soluble antigen/polynucleotide contacting the same APC is increased.

Transcutaneous immunization with bacterial ADP-ribosylating exotoxins (bAREs) as an example, may target the epidermal Langerhans cell, known to be among the most efficient of the antigen presenting cells (APCs). We have found that bAREs activate Langerhans cells when applied epicutaneously to the skin in solution. The Langerhans cells direct specific immune responses through phagocytosis of the antigens, and migration to the lymph nodes where they act as APCs to present the antigen to lymphocytes, and thereby induce a potent antibody response. Although the skin is generally considered a barrier to invading organisms, the imperfection of this barrier is attested to by the numerous Langerhans cells distributed throughout the epidermis that are designed to orchestrate the immune response against organisms invading via the skin. According to Udey (1997):

"Langerhans cells are bone-marrow derived cells that are present in all mammalian stratified squamous epithelia. They comprise all of the accessory cell activity that is present in uninflammed epidermis, an in the current paradigm are essential for the initiation and propagation of immune responses directed against epicutaneously applied antigens. Langerhans cells are members of a family of potent accessory cells ('dendritic cells') that are widely distributed, but infrequently represented, in epithelia and solid organs as well as in lymphoid tissue.

"It is now recognized that Langerhans cells (and presumably other dendritic cells) have a life cycle with at least two distinct stages. Langerhans cells that are located in epidermis constitute a regular network of antigen-trapping 'sentinel' cells. Epidermal Langerhans cells can ingest particulates, including microorganisms, and are efficient processors of complex antigens. However, they express only low levels of MHC class I and II antigens and costimulatory molecules (ICAM-1, B7-1 and B7-2) and are poor stimulators of unprimed T cells. After contact with antigen, some Langerhans cells become activated, exit the epidermis and migrate to T-cell-dependent regions of regional lymph nodes where they localize as mature dendritic cells. In the course of exiting the epidermis and migrating to lymph nodes, antigen-bearing epidermal Langerhans cells (now the 'messengers') exhibit dramatic changes in morphology, surface phenotype and function. In contrast to epidermal Langerhans cells, lymphoid dendritic cells are essentially non-phagocytic and process protein antigens inefficiently, but express high levels of MHC class I and class II antigens and various costimulatory molecules and are the most potent stimulators of naive T cells that have been identified."

We envision that the potent antigen presenting capability of the epidermal Langerhans cells can be exploited for skin delivered vaccines. A transcutaneous immune response using the skin immune system may only require delivery of vaccine antigen to Langerhans cells in the stratum corneum (the outermost layer of the skin consisting of cornified cells and lipids) via passive diffusion or micropenetration. Subsequently, Langerhans cell are activated, take up the antigen, process the antigen, migrate to B-cell follicles and/or T-cell dependent regions, present the antigen to B and/or T cells, and combinations thereof. If antigens other than bAREs (e.g., BSA) are to be phagocytosed by the Langerhans cells, then these antigens could also be taken to the lymph node for presentation to T cells and subsequently induce an immune response specific for that antigen. Thus, a feature of transcutaneous immunization may be activation of the Langerhans cell, presumably by bacterial ADP-ribosylating exotoxins, activated ADP-ribosylating exotoxin binding subunits (e.g., cholera toxin B subunit), other antigens, or other Langerhans cell activating substances. Increasing the size of the skin population of Langerhans cells by the use of alcohol swabbing or acetone treatment would also be expected to enhance the transcutaneous immune response. In aged or Langerhans cell-depleted skin (e.g., from UV damage), it may be possible to treat with tretinoin to replenish the Langerhans cells (Murphy et al., 1998).

It should be noted that antigens such as LPS are known to be highly toxic when injected or given systemically (Rietschel et al., 1994; Vosika et al., 1984) but if placed on the surface of intact skin are unlikely to induce systemic toxicity, similar to our findings with CT. A similar absence of toxicity could be expected if the skin were penetrated only below the stratum corneum and into the epidermis, but not below the deeper layers of the skin. Thus, the ability to induce activation of the immune system through the skin confers the unexpected advantage of potent immune responses without systemic toxicity.

The mechanism of transcutaneous immunization via Langerhans cells activation, migration and antigen presentation could be shown by a change in morphology and/or number of epidermal Langerhans cells from epidermal sheets transcutaneously immunized with CT or CTB, or by upregulation of major histocompatibility complex (MHC) class II antigens, B7-1, or B7-2. This could also be shown by fluorescent activated cell scanning (FACS) analysis of digested epidermal sheets. Cells could be analyzed by staining (e.g., fluorescence, histochemical) for increased expression of major histocompatibility complex antigens and/or costimulatory molecules (e.g., MHC class II, B7-1, B7-2). In addition, the magnitude of the antibody response induced by transcutaneous immunization and isotype switching to predominantly IgG is generally achieved with T-cell help (Janeway and Travers, 1996), and activation of both Th1 and Th2 pathways is suggested by the production of IgG1 and IgG2a (Paul and Seder, 1994; Seder and Paul, 1994). Alternatively, a large antibody response may be induced by a thymus-independent antigen type 1 (TI-1) which directly activates the B cell (Janeway and Travers, 1996) or could have similar activating effects on B-cells such as up-regulation of MHC Class II, B7, CD40, CD25, and ICAM-1 (Nashar et al., 1997).

Transcutaneous immunization may be induced via the ganglioside GM1 binding activity of CT, LT, or subunits such as CTB. Ganglioside GM1 is a ubiquitous cell membrane glycolipid found on all mammalian cells. When the pentameric CT B subunit binds to the cell surface, a hydrophilic pore is formed which allows the A subunit to insert across the lipid bilayer (Ribi et al., 1988). Other binding targets on the antigen presenting cell may be utilized. The B-subunit of LT binds to ganglioside GM1, in addition to other gangliosides, and its binding activities may account for the fact that LT is highly immunogenic on the skin.

We have shown that transcutaneous immunization by CT or CTB may require ganglioside GM1 binding activity. When mice are transcutaneously immunized with CT, CTA and CTB, only CT and CTB resulted in an immune response. CTA contains the ADP-ribosylating exotoxin activity but only CT and CTB containing the binding activity are able to induce an immune response indicating that the B subunit was necessary and sufficient to immunize through the skin. We conclude that the Langerhans cell may be activated by CTB binding to its cell surface.

Antigens

A transcutaneous immunization system delivers agents to specialized cells (e.g., antigen presentation cell, lymphocyte) that produce an immune response. These agents as a class are called antigens. Antigen may be composed of chemicals such as, for example, carbohydrate, glycolipid, glycoprotein, lipid, lipoprotein, phospholipid, polypeptide, conjugates thereof, or any other material known to induce an immune response. Antigen may be provided as a whole organism such as, for example, a microbe (e.g., bacterium, fungus, parasite, virus), mammalian cells, or virion particle; antigen may be obtained from an extract or lysate, either from whole cells or membrane alone; or antigen may be chemically synthesized or produced by recombinant means.

Antigen of the present invention may be expressed by recombinant means, preferably as a fusion with an affinity or epitope tag (Summers and Smith, 1987; Goeddel, 1990; Ausubel et al., 1996); chemical synthesis of an oligopeptide, either free or conjugated to carrier proteins, may be used to obtain antigen of the present invention (Bodanszky, 1993; Wisdom, 1994). Oligopeptides are considered a type of polypeptide. Oligopeptide lengths of 6 residues to 20 residues are preferred. Polypeptides may also by synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another. Antigen obtained through recombinant means or peptide synthesis, as well as antigen obtained from natural sources or extracts, may be purified by means of the antigen's physical and chemical characteristics, preferably by fractionation or chromatography (Janson and Ryden, 1989; Deutscher, 1990; Scopes, 1993). Recombinants may combine B subunits or chimeras of bAREs (Lu et al., 1997). A multivalent antigen formulation may be used to induce an immune response to more than one antigen at the same time. Conjugates may be used to induce an immune response to multiple antigens, to boost the immune response, or both. Additionally, toxins may be boosted by the use of toxoids, or toxoids boosted by the use of toxins. Transcutaneous immunization may be used to boost responses induced initially by other routes of immunization such as by oral, nasal or parenteral routes. Antigen includes, for example, toxins, toxoids, subunits thereof, or combinations thereof (e.g., cholera toxin, tetanus toxoid); additionally, toxins, toxoids, subunits thereof, or combinations thereof may act as antigen. Such oral/transcutaneous or transcutaneous/oral immunization may be especially important to enhance mucosal immunity in diseases where mucosal immunity correlates with protection.

Antigen may be solubilized in an aqueous solution (with or without buffer) or organic solvents (e.g., alcohols, ketones, DMSO), or incorporated in creams, emulsions, gels, lotions, ointments, pastes, and suspensions. Suitable buffers include, but are not limited to, phosphate buffered saline (PBS) $Ca^{++}$/$Mg^{++}$ free, normal saline (150 mM NaCl in water), and Good buffers (e.g., TRIS tricine). Antigen not soluble in neutral buffer can be solubilized in mild base or acid (e.g., 10 mM acetic acid) and then diluted with a neutral buffer such as PBS. In the case of antigen soluble only at acid pH, acetate-PBS at acid pH may be used as a diluent after solubilization in dilute acetic acid. Glycerol may be a suitable non-aqueous buffer for use in the present invention.

Hydrophobic antigen can be solubilized in a detergent, for example a polypeptide containing a membrane-spanning domain. Furthermore, for formulations containing liposomes, an antigen in a detergent solution (e.g., a cell membrane extract) may be mixed with lipids, and liposomes then may be formed by removal of the detergent by dilution, dialysis, or column chromatography. See Gregoriadis (1992, 1993). Certain antigens such as, for example, those from a virus (e.g., hepatitis A) need not be soluble per se, but can be incorporated directly into a lipid membrane (e.g., a virosome as described by Morein and Simons, 1985), in a suspension of virion alone, or suspensions of micro-spheres or heat-inactivated bacteria which may be taken up by and activate antigen presenting cells (e.g., opsonization). Antigens may also be mixed with preservatives or stabilizers.

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, fungus, parasite, or virus).

Bacteria include, for example: *Bacillis anthracis* (responsible for causing anthrax), *campylobacter*, cholera, clostridia, diphtheria, enterohemorrhagic *E. coli*, enterotoxigenic *E. coli*, giardia, gonococcus, *Helicobacter pylori* or urease produced by *H. pylori* (Lee and Chen, 1994), *Hemophilus influenza* B, *Hemophilus influenza* non-typable, meningococcus, mycobacterium, pertussis, pneumococcus, salmonella, shigella, staphylococcus, *Streptococcus* B, Group A beta hemolytic *streptococcus, Streptococcus mutans*, tetanus, *Vibrio cholera, Borrelia burgdorfi* and *Yersinia*; and products thereof.

Fungi including entities responsible for tinea corporis, tinea unguis, sporotrichosis, aspergillosis, candida, other pathogenic fungi, and products thereof.

Parasites include, for example: *Entamoeba histolytica* (Zhang et al., 1995); *Plasmodium* (Bathurst et al., 1993; Chang et al., 1989, 1992, 1994; Fries et al., 1992a, 1992b; Herrington et al., 1991; Khusmith et al, 1991; Malik et al., 1991; Migliorini et al., 1993; Pessi et al., 1991; Tam, 1988; Vreden et al., 1991; White et al., 1993; Wiesmueller et al., 1991), *Leishmania* (Frankenburg et al., 1996), and the Helminthes; and products thereof.

Viruses include, for example: adenovirus, dengue serotypes 1 to 4 (Delenda et al., 1994; Fonseca et al., 1994; Smucny et al., 1995), ebola (Jahrling et al., 1996), enterovi rus, hanta virus, hepatitis serotypes A to E (Blum, 1995; Katkov, 1996; Lieberman and Greenberg, 1996; Mast and Krawczynski, 1996; Shafara et al., 1995; Smedile et al., 1994; U.S. Pat. Nos. 5,314,808 and 5,436,126), herpes simplex virus 1 or 2, human immunodeficiency virus (Deprez et al., 1996), human papilloma virus, influenza, measles, Norwalk, Japanese equine encephalitis, papilloma virus, parvovirus B19, polio, rabies, respiratory syncytial virus, rotavirus, rubella, rubeola, St. Louis encephalitis, vaccinia, viral expression vectors containing genes coding for other antigens such as malaria antigens, varicella, and yellow fever; and products thereof.

Of particular interest are pathogens that enter on or through a mucosal surface such as, for example, pathogenic species in the bacterial genera *Actinomyces, Aeromonas, Bacillus, Bacteroides, Bordetella, Brucella, Campylobacter, Capnocytophaga, Clamydia, Clostridium, Corynebacterium, Eikenella, Erysipelothrix, Escherichia, Fusobacterium, Hemophilus, Klebsiella, Legionella, Leptospira, Listeria, Mycobacterium, Mycoplasma, Neisseria, Nocardia, Pasteurella, Proteus, Pseudomonas, Rickettsia, Salmonella, Selenomonas, Shigella, Staphylococcus, Streptococcus, Treponema, Vibrio,* and *Versinia*; pathogenic viral strains from the groups Adenovirus, Coronavirus, Herpesvirus, Orthomyxovirus, Picornovirus, Poxvirus, Reovirus, Retrovirus, Rotavirus; pathogenic fungi from the genera *Aspergillus, Blastomyces, Candida, Coccidiodes, Cryptococcus, Histoplasma* and *Phycomyces*; and pathogenic parasites in the genera *Eimeria, Entamoeba, Giardia,* and *Trichomonas.*

Other viruses which can be used in the present invention (and diseases associated with viral infection) are disclosed in Gordon (1997) and include, for example, Adenovirus (respiratory disease), Coronavirus (respiratory and enteric disease), Cytomegalovirus (mononucleosis), Dengue virus (dengue fever, shock syndrome), Epstein-Barr virus (mononucleosis, Burkitt's lymphoma), Hepatitis A, B and C virus (liver disease), Herpes simplex virus type 1 (encephalitis, stomatitis), Herpes simplex virus type 2 (genital lesions), Human herpesvirus-6 (unknown, possibly Kaposi's sarcoma), Human immunodeficiency virus types 1 and 2 (acquired immunodeficiency syndrome-AIDS), Human T-cell lymphotropic virus type 1 (T-cell leukemia), Influenza A, B, and C (respiratory disease), Japanese encephalitis virus (pneumonia, encephalopathy), Measles virus (subacute sclerosing panencephalitis), Mumps virus (meningitis, encephalitis), Papillomavirus (warts, cervical carcinoma), Parvovirus (respiratory disease, anemia), Poliovirus (paralysis), Polyomavirus JC (multifocal leukoencephalopathy), Polyomavirus BK (hemorrhagic cystitis), Rabies virus (nerve dysfunction), Respiratory syncytial virus (respiratory disease), Rhinovirus (common cold), Rotavirus (diarrhea), Rubella virus (fetal malformations), Vaccinia virus (generalized infection), Yellow fever virus (jaundice, renal and hepatic failure), Varicella zoster virus (chickenpox).

Other bacteria which can be used in the present invention (and diseases associated with bacterial infection) are disclosed in Gordon (1997) and include, for example, *Bacillus anthracis* (anthrax), *Bordetella pertussis* (whooping cough), *Borrelia burgdorferi* (lyme disease), *Campylobacter jejuni* (gastroenteritis), *Chlamydia trachomatis* (pelvic inflammatory disease, blindness), *Clostridium botulinum* (botulism), *Corynebacterium dipththeriae* (diphtheria), *Escherichia coli* (diarrhea, urinary tract infections), *Haemophilus influenzae* (pneumonia), *Helicobacter pylori* (gastritis, duodenal ulcer), *Legionella pneumophila* (Legionnaires' disease), *Listeria monocytogenes* (meningitis, sepsis), *Mycobacterium leprae* (leprosy), *Mycobacterium tuberculosis* (tuberculosis), *Neisseria gonorrhoeae* (gonorrhea), *Neisseria meningitidis* (sepsis, meningitis), *Pseudomonas aeruginosa* (nosocomial infections), *Pseudomonas aeruginosa* (nosocomial infections), *Rickettsia* (Rocky Mountain spotted fever), *Salmonella* (typhoid fever, gastroenteritis), *Shigella* (dysentery), *Staphylococcus aureus* (impetigo, toxic shock syndrome), *Streptococcus pneumoniae* (pneumonia, otitis media), *Streptococcus pyogenes* (Rheumatic fever, pharyngitis), *Treponema pallidum* (syphilis), *Vibrio cholerae* (cholera), *Yersinia pestis* (bubonic plague).

Other parasites which can be used in the present invention (and diseases associated with parasitic infection) are disclosed in Gordon (1997) and include, for example, *African trypanosomes* (trypanosomiasis), *Entamoeba histolytica* (amebic dysentery), *Giardia lamblia* (diarrheal disease), *Leishmania* (lesions of the spleen, tropical sores), *Plasmodium* (malaria), *Microfilariae* (filariasis), *Schistosomes* (schistosomiasis), *Toxoplasma gondii* (toxoplasmosis), *Trichomonas vaginalis* (vaginitis), *Trypanosoma cruzi* (Chagas disease).

Other fungi which can be used in the present invention (and diseases associated with fungal infection) are disclosed in Gordon (1997) and include, for example, *Candida albicans* (mucosal infections), *Histoplasma* (lung, lymph node infections), *Pneumocystis carinii* (pneumonia in AIDS), *Aspergillus fumigatis* (aspergillosis).

Adjuvants

The formulation does not contain a heterologous adjuvant, although a single molecule of the formulation may contain both adjuvant and antigen activities (e.g., cholera toxin) (Elson and Dertzbaugh, 1994). Adjuvants are substances that are used to specifically or non-specifically potentiate an antigen-specific immune response. Usually, components of the formulation are mixed prior to presentation of the antigen but, alternatively, they may be separately administered within a short interval of time or at different sites.

Adjuvants include, for example, an oil-in-water (O/W) or water-in-oil (W/O) emulsion; chemokines (e.g., defensins 1 and 2, RANTES, MIP1-α, interleukin-8); cytokines (e.g., interleukin-1β, -2, -6, -10 or -12; interferon alpha, interferon gamma, tumor necrosis factor-α; granulocyte-monocyte colony stimulating factor (GM-CSF); reviewed in Nohria and Rubin, 1994); growth/differentiation factors; muramyl dipeptide (MDP), muramyl tripeptide (MTP), or derivatives thereof (e.g., murabutide, threonyl MDP (SAF-1), butyl-ester MDP, dipalmitoyl phosphatidylethanoamine MTP); a heat shock protein or derivative thereof; a derivative of *Leishmania major* LeIF (Skeiky et al., 1995); cholera toxin or cholera toxin B; recombinants containing the B subunit of CT, LT or other bAREs; lipopolysaccharides (LPS) or derivatives thereof (e.g., lipid A or monophosphoryl lipid A), superantigens (Saloga et al., 1996b); and saponins or derivatives thereof (Newman et al., 1997). Other adjuvants include nonionic block copolymers; virosomes; ISCOMS; dimethyl diotadecyl ammonium bromide (DDA); trehelose dimycolate; pyridine; vitamins A and/or E; bacterial products such as cell wall skeletal products of mycobacterium; *Klebsiella pneumonia* glycoprotein; *Bordetella pertussis, Bacillus* Calmette-Guerin (BCG), *Corynebacterium parvum,* or purified components thereof (e.g., lipopolysaccharide); 1,25 dihydroxy vitamin D3; human growth hormone, polyanions (e.g., dextran); double-stranded polynucleotide (e.g., poly dI-dC); polymethylmethacrylate, acryllic acid cross linked with allyl sucrose, CGP-11637; gamma inulin plus aluminum; lysophosphatidyl glycerol; stearyl tyrosine; and tripalmitoyl pentapeptide. Also, see Richards et al. (1995) for other adjuvants useful in immunization.

Carriers such as hepatitis core, fatty acids, bentonite, keyhole limpet hemocyanin; living vectors such as vaccinia, canarypox, adenovirus, attenuated *salmonella*, BCG, fowlpox virus, herpes simplex virus, polio vaccine virus, rhinovirus, Venezualan equinine encephalitis, *Yersinia enterocolitica, Listeria monocytogenes, Shigella, Streptococcus gordonni, Saccharomyces cerevisiae*; biodegradable microspheres including lactide and glycolide, polyphazenes, beta-glucan, and proteinoids may be used.

An adjuvant may preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$) (see, for example, Munoz et al., 1990; Glenn et al., 1995).

CpGs are among a class of structures which have patterns allowing the immune system to recognize their pathogenic origins to stimulate the innate immune response leading to adaptive immune responses (Medzhitov and Janeway, 1997). These structures have been called pathogen-associated molecular patterns (PAMPs): lipopolysaccharides, teichoic acids, unmethylated CpG motifs, double-stranded RNA, and mannins.

PAMPs induce endogenous signals that can mediate the inflammatory response, act as costimulators of T-cell function and control the effector function. The ability of PAMPs to induce these responses play a role in their potential as adjuvants. Their targets are antigen presenting cells (APCs) such as macrophages and dendritic cells. APCs of the skin could likewise be stimulated by PAMPs transmitted through the skin. For example, Langerhans cells, a type of dendritic cell, could be activated by a PAMP in solution on the skin with a transcutaneously poorly immunogenic molecule and be induced to migrate and present this poorly immunogenic molecule to T-cells in the lymph node, inducing an antibody response to the poorly immunogenic molecule. PAMPs could also be used in conjunction with other skin adjuvants such as cholera toxin to induce different co-stimulatory molecules and control different effector functions to guide the immune response, for example from a Th2 to a Th1 response.

Cholera toxin is a bacterial exotoxin from the family of ADP-ribsoylating exotoxins (referred to as bAREs). Most bAREs are organized as A:B dimer with a binding B subunit and an A subunit containing the ADP-ribosyltransferase. Such toxins include diphtheria, *Pseudomonas* exotoxin A, cholera toxin (CT), *E. coli* heat-labile enterotoxin (LT), pertussis toxin, *C. botulinum* toxin C2, *C. botulinum* toxin C3, *C. limosum* exoenzyme, *B. cereus* exoenzyme, *Pseudomonas* exotoxin S, *Staphylococcus aureus* EDIN, and *B. sphaericus* toxins.

Cholera toxin is an example of a bARE that is organized with A and B subunits. The B subunit is the binding subunit and consists of a B-subunit pentamer which is non-covalently bound to the A subunit. The B-subunit pentamer is arranged in a symmetrical doughnut-shaped structure that binds to GM1-ganglioside on the target cell. The A subunit serves to ADP ribosylate the alpha subunit of a subset of the hetero trimeric GTP proteins (G proteins) including the Gs protein which results in the elevated intracellular levels of cyclic AMP. This stimulates release of ions and fluid from intestinal cells in the case of cholera.

Cholera toxin (CT) and its B subunit (CTB) have adjuvant properties when used as either an intramuscular or oral immunogen (Elson and Dertzbaugh, 1994; Trach et al., 1997). Another antigen, heat-labile enterotoxin from *E. coli* (LT) is 75-77% homologous at the amino acid level with CT and possesses similar binding properties; it also appears to bind the GM1-ganglioside receptor in the gut and has similar ADP-ribosylating exotoxin activities. Another bARE, *Pseudomonas* exotoxin A (ETA), binds to the a2-macroglobulin receptor-low density lipoprotein receptor-related protein (Kounnas et al., 1992). bAREs are reviewed by Krueger and Barbieri (1995). CT, CTB, LT, ETA and PT, despite having different cellular binding sites, are potent adjuvants for transcutaneous immunization, inducing high levels of IgG antibodies but not IgE antibodies. CTB without CT can also induce high levels of IgG antibodies. Thus, both bAREs and a derivative thereof can effectively immunize when epicutaneously applied to the skin in a simple solution.

When an adjuvant such as CT is mixed with BSA, a protein not usually immunogenic when applied to the skin, anti-BSA antibodies are induced. An immune response to diphtheria toxoid was induced using pertussis toxin as adjuvant, but not with diphtheria toxoid alone. Native LT as an adjuvant and antigen, however, is clearly not as potent as native CT. But activated bAREs can act as adjuvants for non-immunogenic proteins in an transcutaneous immunization system. Thus, therapeutic immunization with an antigen for the organism such as HIV, HPV, or *leishmania* could be used separately or in conjunction with immunostimulation of the infected antigen presenting cell to induce a therapeutic immunization.

CT can also act as an adjuvant to induce antigen-specific CTLs through transcutaneous immunization. The bARE adjuvant may be chemically conjugated to other antigens including, for example, carbohydrates, polypeptides, glycolipids, and glycoprotein antigens. Chemical conjugation with toxins, their subunits, or toxoids with these antigens would be expected to enhance the immune response to these antigens when applied epicutaneously. To overcome the problem of the toxicity of the toxins, (e.g., diphtheria toxin is known to be so toxic that one molecule can kill a cell) and to overcome the difficulty of working with such potent toxins as tetanus, several workers have taken a recombinant approach to producing genetically altered toxoids. This is based on inactivating the catalytic activity of the ADP-ribosyl transferase by genetic deletion. These toxins retain the binding capabilities, but lack the toxicity, of the natural toxins. This approach is described by Burnette et al. (1994), Rappuoli et al. (1995), Dickinson and Clements (1995), and Rappuoli et al. (1996). Such genetically toxoided exotoxins could be useful for transcutaneous immunization system in that they would not create a safety concern as the toxoids would not be considered toxic. Additionally, several techniques exist to chemically toxoid toxins which can address the same problem (Schneerson et al., 1996). These techniques could be important for certain applications, especially pediatric applications, in which ingested toxin (e.g., diphtheria toxin) might possibly create adverse reactions.

Optionally, an activator of the Langerhans cell may be used as an adjuvant. Examples of such activators include: an inducer of heat shock protein; contact sensitizer (e.g., trinitrochlorobenzene, dinitrofluorobenzene, nitrogen mustard, pentadecylcatechol); toxin (e.g., Shiga toxin, Staph enterotoxin B); lipopolysaccharides, lipid A, or derivatives and analogs thereof; bacterial DNA (Stacey et al., 1996); cytokine (e.g., tumor necrosis factor-$\alpha$, interleukin-1$\beta$, -10, -12); members of the TGF$\beta$ family; calcium ions in solution; calcium ionophores, and chemokine (e.g., defensins 1 and 2, RANTES, MIP-1$\alpha$, MIP-2, interleukin-8).

If an immunizing antigen has sufficient Langerhans cell activating capabilities then a separate adjuvant may not be required, as in the case of CT which is both antigen and adjuvant. Whole cell preparations, live pathogens, attenuated pathogens, inactivated pathogens, recombinant pathogens, DNA plasmids, and bacterial DNA may also be used to immunize transcutaneously. It may be possible to use low concentrations of contact sensitizers or other activators of Langerhans cells to induce an immune response without inducing skin lesions.

For example, components of the formulation such as LT may be activated using proteolytic (e.g., trypsin) or similar modifications prior to application the skin to enhance the adjuvant activity and immunogenicity of LT. Activation of LT could also be expected to enhance the immune response to LT as an antigen. The activated adjuvant for transcutaneous immunization is preferably an ADP-ribosylating exotoxin. Optionally, hydration or occlusive dressings may be used in the transcutaneous delivery system in addition to the activation of the adjuvant.

In addition, LT has an unusual affinity for carbohydrate-containing matrices. Specifically, LT binds to an array of biological molecules containing galactose, including glycoproteins and lipopolysaccharides. This lectin-like binding property of LT results in a broader receptor distribution on mammalian cells for LT than for CT, which binds only to GM1. The two molecules also have many immunologic differences, as demonstrated by immunodiffusion studies, against LT-associated *E. coli* diarrhea in volunteers receiving B-subunit whole whole-cell cholera vaccine. LT and CT induce different helper T-cell responses. When used as a mucosal adjuvant, CT selectively induces in some cases Th2-type cells in Peyers patches and spleens as manifested by production of interleukins 4 and 5, but not interleukin 2 or gamma interferon; while LT induces both Th1 and Th2 cells and predominantly antigen-specific IgA responses. Taken together, these findings demonstrate that LT and CT are unique molecules, despite their apparent structural similarities. Such differential behavior makes the ability to activate LT so that it has potency similar to CT useful in manipulating the type of immune response produced to both the toxin itself and to antigens for which LT can be used as an adjuvant. It may also be possible that genetically altered toxoids such as mutants of the trypsin cleavage site may be active by transcutaneous immunization. Such a mutant toxin may be useful as it avoids the risks associated with ingestion or inhalation of native toxins.

In a similar manner, PT may be activated to enhance its adjuvant and antigen activities. The S1 subunit of the hexameric PT protein contains the ADP-ribosyltransferase activity while the remaining subunits constitute the B domain. Similar to LT, PT has both trypsin cleavage sites and disulphide bonding sites that play a role in association of the S1 subunit with the B oligomer. It is conceivable that activation by trypsin cleavage, disruption of a disulphide bond, or both may enhance the adjuvant and antigen activities of PT in the context of transcutaneous immunization. Activation may also take the form of targeting, achieved by disruption of the hexamer into subunits. For example, the PT subunit S3 appears to bind exclusively to the glycolipids of monocytes and could be used to target Langerhans cells in the skin.

Activation of the antigen or adjuvant could be extended to the concept of transcutaneous immunization using DNA by production of a fusion protein comprised of antigen and adjuvant domains. By this method a plasmid encoding an ADP-ribosylating exotoxin such as CT or LT and constructed to express a separate antigen such as a malaria or HIV antigen simultaneously could be placed on the skin in a hydrating solution or occlusive patch, and then taken up by Langerhans cells. Expression of the an ADP-ribosylating exotoxin component of the fusions protein such as CT or LT could activate the Langerhans cell, causing it to migrate and present antigen in the lymph node and thereby induce an immune response to the encoded antigen. Another embodiment could include the conjugation of an adjuvant with a plasmid; an Fc portion of IgG to a plasmid to target APCs. A similar immunization could be achieved using separate plasmids for expressing an ADP-ribosylating exotoxin such as CT or LT and another for expressing the antigen such as a malaria or HIV antigen. It is conceivable that multiple genes on a single construct for multiple antigens could be used or multiple plasmids could be used to simultaneously deliver antigens for multivalent immunization. Plasmids encoding other molecules or compounds such as chemokines (e.g., defensins 1 or 2, RANTES, MIP1-α, MIP-2, interleukin-8) or cytokines (e.g., interleukin-1β, -2, -6, -10, -12; γ-interferon; tumor necrosis factor-α; or granulocyte-monocyte colony stimulating factor), heat shock proteins or derivatives, derivatives of *Leishmania major* LeIF, cholera toxin B, lipopolysaccharide (LPS) derivatives (e.g., lipid A, monophosphoryl lipid A), superantigens, or other ADP-ribosylating exotoxins might be delivered with the antigen.

Other means of activating the transcutaneous adjuvants may be effective, such as adding surfactants and/or phospholipids to the formulation to enhance adjuvant activity of ADP-ribosylating exotoxin by ADP-ribosylation factor (see Spangler, 1992). Optionally, one or more ADP-ribosylation factors (ARFs) may be used to enhance the adjuvanticity of CT (e.g., ARF1, ARF2, ARF3, ARF4, ARF5, ARF6, ARD1; see Moss and Vaughan, 1995). Similarly, one or more ARFs could be used with an ADP-ribosylating exotoxin to enhance its adjuvant activity.

For immunization using adjuvant or antigen activation, modification of the adjuvant or antigen component of the formulation may reduce its effectiveness in oral, parenteral, or enteral immunization without destroying the utility of the formulation in transcutaneous immunization when the adjuvant and/or antigen is activated. Undesirable properties (e.g., toxicity, allergic reactivity, other harmful side effects) of the adjuvant or antigen in the formulation may be reduced by modification without destroying its effectiveness in transcutaneous immunization. Activation of such modified adjuvant or antigen may involve, for example, removal of a reversible chemical modification (e.g., proteolysis) or a coating which reversibly isolates a component of the formulation from the immune system (i.e., an encapsulated formulation). Alternatively, the adjuvant and/or antigen comprising the formulation may be encapsulated in a particle (e.g., microspheres, nanoparticles). Phagocytosis of a particle may, by itself, enhance activation of an antigen presenting cell by upregulating expression of major histocompatibility antigens and/or co-stimulatory molecules (e.g., MHC class II, B7-2).

Formulations

Processes for manufacturing a pharmaceutical formulation are well known. See generally, *Ullmann's Encyclopedia of Industrial Chemistry,* $6^{th}$ Ed. (electronic edition, 1998); *Remington's Pharmaceutical Sciences,* $22^{nd}$ (Gennaro, 1990, Mack Publishing); *Pharmaceutical Dosage Forms,* $2^{nd}$ Ed. (various editors, 1989-1998, Marcel Dekker); and *Pharmaceutical Dosage Forms and Drug Delivery Systems* (Ansel et al., 1994, Williams & Wilkins). Such formulations will contain an effective amount of the antigen and/or polynucleotide encoding antigen—some of which may be in a complex or together with a penetration enhancer, targeting molecule for antigen presenting cells, and/or endosomolytic agent—in a suitable amount of vehicle to prepare pharmaceutically acceptable compositions suitable for administration to a human or animal. The formulation may be applied in the form of an cream, emulsion, gel, lotion, ointment, paste, solution, suspension, or other liquid forms known in the art. In particular, formulations that enhance skin hydration are preferred. Solid dosage form (e.g., powders, granules, pellets, tablets) may also be used.

The components of the formulation (i.e., antigen, polynucleotide encoding antigen, agents that form a complex of at least antigen, agents that stabilize the formed complex, penetration enhancers, targeting molecules, endosomolytic agents) may be combined with a pharmaceutically-acceptable carrier or vehicle, as well as any combination of optional additives (e.g., binders, colorings, diluents, excipients, stabilizers, preservatives). The terms "consisting essentially" or "consists essentially" as used in the claimed invention refers to active ingredients that contribute to inducing or enhancing the immune response, in contrast to the aforementioned optional additives. Use of stabilizers of antigen activity, adjuvant activity in the antigen molecule, the complex that is formed, and combinations thereof are preferred embodiments.

Good manufacturing practices are known in the pharmaceutical industry and regulated by government agencies (e.g., Food and Drug Administration) for vaccines and related biologicals. Sterile liquid formulations may be prepared by dissolving an intended component of the formulation in a sufficient amount of an appropriate solvent, followed by sterilization by filtration to remove contaminating microbes. Suspensions are prepared by incorporating the sterilized components of the formulation, at least some of which is insoluble, into a sterile vehicle or carrier. For production of solid forms that are required to be sterile, preferred preparation methods are vacuum drying and freeze drying.

The production of patches and other medical devices to deliver pharmaceuticals are also known. In general, single dose packaging (i.e., a unit dose) in a container for aseptic storage and safe transportation is preferred. The size of each dose and the interval of dosing to the subject may be used to determine a suitable size and shape of a container, chamber of the patch, or compartment of the medical device.

Formulations will contain an effective amount of the active ingredients together with a suitable amount of carrier or vehicle in order to provide pharmaceutically-acceptable compositions suitable for administration to a human or animal. The relative amounts of active ingredients within a dose and the dosing schedule may be adjusted appropriately for efficacious administration to a subject (e.g., animal or human). This adjustment may also depend on the subject's particular disease or condition, and whether treatment or prophylaxis is intended. Side effects (e.g., reactogenicity) may be reduced by using a lower, but still effective, amount of the component of the formulation. Alternatively, some side effects might be tolerated because of the overall benefit to health.

There are numerous causes of polypeptide instability or degradation, including hydrolysis and denaturation. In the case of denaturation, the conformation or three-dimensional structure of the protein is disturbed and the protein unfolds from its usual globular structure. Rather than refolding to its natural conformation, hydrophobic interaction may cause clumping of molecules together (i.e., aggregation) or refolding to an unnatural conformation. Either of these results may entail diminution or loss of antigen activity. Stabilizers may be added to the formulation to lessen or prevent such problems during reconstitution prior to or solubilization after application to the skin.

The formulation, or any intermediate in its production, may be pretreated with protective agents (e.g., cryoprotectants) and then subjected to cooling rates and final temperatures that minimize ice crystal formation. By proper selection of cryoprotective agents and use of pre-selected freezing parameters, almost any formulation might be frozen and stored for a desired end use.

The transcutaneous immunization system may be applied directly on the skin and allowed to air dry; rubbed into the skin or scalp (i.e., massaging); placed on the ear, inguinal, or intertriginous regions, especially for animals with skin that is not readily accessible or to limit self-grooming; held in place with a dressing, patch, or absorbent material; applied by bathing an exposed skin surface or immersing a body part; otherwise held in place by a device such as a stocking, slipper, glove, or shirt; or sprayed onto the skin to maximize contact with the skin. The formulation may be applied in an absorbent dressing or gauze. The formulation may be covered with an occlusive dressing such as, for example, AQUAPHOR (an emulsion of petrolatum, mineral oil, mineral wax, wool wax, panthenol, bisabol, and glycerin from Beiersdorf), COMFEEL (Coloplast), plastic film, or vaseline; or a non-occlusive dressing such as, for example, DUODERM (3M), OPSITE (Smith & Napheu), or TEGADERM (3M). An occlusive dressing excludes the passage of water. The formulation may be applied to single or multiple sites, single or multiple limbs, or large surface areas of the skin by bathing or immersion in a container. The formulation may be applied directly to the skin. One or more components of the formulation may be provided in dry form.

Transcutaneous Delivery of Antigen

Efficient immunization can be achieved with the present invention because transcutaneous delivery of antigen may target the Langerhans cell. These cells are found in abundance in the skin and are efficient antigen presenting cells leading to T-cell memory and potent immune responses. Because of the presence of large numbers of Langerhans cells in the skin, the efficiency of transcutaneous delivery may be related to the surface area exposed to antigen. In fact, the reason that transcutaneous immunization is so efficient may be that it targets a larger number of these efficient antigen presenting cells than intramuscular immunization.

We envision the present invention will enhance access to immunization, while inducing a potent immune response. Because transcutaneous immunization does not require injection with a hypodermic needle (i.e., penetration to or through the dermis) and the complications and difficulties thereof, the usual requirements of trained personnel, sterile technique, and sterile equipment are reduced. Furthermore, the bathers to immunization at multiple sites or to multiple immunizations are diminished. Immunization by a single application of the formulation is also envisioned, especially to achieve some degree of immunoprotection.

Immunization may be achieved using epicutaneous application of a simple solution of antigen and/or polynucleotide encoding antigen impregnated in gauze under an occlusive patch, or by using other patch technologies; a medical device that delivers pharmaceuticals to a limited depth below the stratum corneum (i.e., above the dermis, in the epidermis, or above the epidermis); bathing or immersion, rubbing or massaging, painting, spraying, and wetting or wiping are other possible methods of application. Immunization could be performed by untrained personnel, and is even amenable to self-application. Large-scale field immunization could occur given the easy accessibility to immunization. Additionally, a simple immunization procedure would improve access to immunization by pediatric patients and the elderly, and populations in Third World countries.

Superficial penetration of the stratum corneum may involve physical or chemical penetration. Physical methods include removing an adhesive strip from the skin (i.e., tape stripping); inserting a microneedle above or in the epidermis, but not past into the dermis; rubbing the skin with abrasive material; or shooting a projectile with a pneumatic gun above or in the epidermis, but not past the dermis. Chemicals that may be used are mild acid or alkaline compounds, detergents, keratinolytic agents, and surfactants.

Increasing hydration of the stratum corneum will increase the rate of percutaneous absorption of a given solute (Roberts and Walker, 1993). As used in the present invention, penetration enhancer does not include substances such as, for example: water, physiological buffers, and saline solutions which would not perforate the skin. An object of the present invention is to both utilize the novel means for immunization through intact skin without the need for perforating the skin, or to use chemical/physical permeation enhancers or micropenetration through the stratum corneum, to bring antigen in contact with antigen presenting cells (APCs). The transcutaneous immunization system provides a method whereby antigen and/or polynucleotide encoding antigen can be delivered to the immune system, especially specialized APCs underlying the skin (e.g., Langerhans cells).

Moreover, transcutaneous immunization may be superior to immunization using needles as more immune cells would be targeted by the use of several locations targeting large surface areas of skin. A therapeutically effective amount of antigen sufficient to induce an immune response may be delivered transcutaneously either at a single cutaneous location, or over an area of intact skin covering multiple draining lymph node fields (e.g., cervical, axillary, inguinal, epitrochelear, popliteal, those of the abdomen and thorax). Such such locations close to numerous different lymphatic nodes at locations all over the body will provide a more widespread stimulus to the immune system than when a small amount of antigen is injected at a single location by intradermal subcutaneous or intramuscular injection.

Antigen passing through or into the skin may encounter antigen presenting cells which process the antigen in a way that induces an immune response. Multiple immunization sites may recruit a greater number of antigen presenting cells and the larger population of antigen presenting cells that were recruited would result in greater induction of the immune response. It is conceivable that absorption through the skin may deliver antigen to phagocytic cells of the skin such as, for example, dermal dendritic cells, macrophages, and other skin antigen presenting cells; antigen may also be delivered to phagocytic cells of the liver, spleen, and bone marrow and cells of the reticuloendothelial system that are known to serve as the antigen presenting cells through the blood stream or lymphatic system.

Antigen present cells may be specifically targeted using receptors and other cell-surface molecules expressed thereon by forming complexes of at least one component of the formulation with a ligand and/or other specific binder of the cell-surface molecule, respectively. Such a component would target the complex to an antigen presenting cell and be considered a heterologous molecule of the complex.

Genetic immunization has been described in U.S. Pat. Nos. 5,589,466, 5,593,972, 5,679,647, 5,697,901, 5,804,566, 5,830,877, and 5,849,719. The polynucleotide(s) contained in the formulation may encode the antigen, penetration enhancer, targeting molecule, endosomo-lytic agent, or combinations thereof. Coding sequences may be operably linked to another coding sequence to form a fusion protein. Thus, if antigen and another non-heterologous adjuvant sequences are provided on a single polynucleotide, they may be encoded by two separate sequences, a fused sequence(s), or even a single sequence encoding a single polypeptide (e.g., cholera toxin). The polynucleotide may or may not be capable of replication; it may be non-integrating and non-infectious. The polynucleotide may further comprise a regulatory region (e.g., promoter, enhancer, silencer, transcription initiation and termination signals, RNA splice acceptor and donor sites, polyadenylation signal, internal ribosome binding site, translation initiation and termination sites) operably linked to the sequence encoding antigen or other components of the formulation. Optionally, the polynucleotide may include a region such as an origin of replication, centromere, telomere; polylinker; selectable marker, histochemical indicator, sequence encoding same; cellular localization signal, protease cleavage site, epitope tag, sequence encoding same; or combinations thereof.

The polynucleotide may be complexed with an agent that promotes transfection: for example, cationic lipids (e.g., cationic phospholipids, quaternary ammonium lipids), cationic polymers (e.g., polyethyleneimines, cationic dendrimers, polyamides, polyamidoamines), calcium phosphate, DEAE-dextran, hexadimethrine bromide-DMSO, polyethylene and polypropylene glycols, polylysines, or combinations thereof. A heterologous molecule may be included in the complex, bonded either covently or non-covalently to the polynucleotide(s), to target the complex to the immune system. The polynucleotide may be comprised of regulatory regions or genes for surface molecules (e.g., glycoprotein, protein, glycolipid, and carbohydrate antigens) from microbial genomes. See Kriegler (1990) and Murray (1991).

An immune response may comprise humoral (i.e., antigen-specific antibody) or cellular (i.e., antigen-specific lymphocytes such as B cells, $CD4^+$ T cells, $CD8^+$ T cells, CTL, Th1 cells, Th2 cells, and/or $T_{DTH}$ cells) effector arms, or both. Moreover, the immune response may comprise NK cells that mediate antibody-dependent cell-mediated cytotoxicity (ADCC).

The immune response induced by the formulation of the present invention may include the elicitation of antigen-specific antibodies and/or cytotoxic lymphocytes (reviewed in Alving and Wassef, 1994). Antibody can be detected by immunoassay techniques, and the detection of various isotypes (e.g., IgM, IgD, IgA1, IgA2, secretory IgA, IgE, IgG1, IgG2, IgG3, or IgG4) may be expected. An immune response can also be detected by a neutralizing assay. Antibodies are protective proteins produced by B lymphocytes. They are highly specific, generally targeting one epitope of an antigen. Often, antibodies play a role in protection against disease by specifically reacting with antigens derived from the pathogens causing the disease. Immunization may induce antibodies specific for the immunizing antigen, such as cholera toxin.

CTLs are particular protective immune cells produced to protect against infection by a pathogen. They are also highly specific. Immunization may induce CTLs specific for the antigen, such as a synthetic oligopeptide based on a malaria protein, in association with self-major histocompatibility antigen. CTLs induced by immunization with the transcutaneous delivery system may kill pathogen infected cells. Immunization may also produce a memory response as indicated by boosting responses in antibodies and CTLs, lymphocyte proliferation by culture of lymphocytes stimulated with the antigen, and delayed type hypersensitivity responses to intradermal skin challenge of the antigen alone.

In a viral neutralization assay, serial dilutions of sera are added to host cells which are then observed for infection after challenge with infectious virus. Alternatively, serial dilutions of sera may be incubated with infectious titers of virus prior to inoculation of an animal, and the innoculated animals are then observed for signs of infection.

The transcutaneous immunization system of the present invention may be evaluated using challenge models in either animals or humans, which evaluate the ability of immunization with the antigen to cure or ameliorate the disease. Such immunotherapy would demonstrate an antigen-specific immune response. In lieu of challenge, achieving certain levels of neutralizing antibodies (e.g., anti-diphtheria antibody titers greater than about 5 IU/ml) is recognized in the art to serve as a surrogate marker for immunoprotection (Plotkin and Mortimer, 1994).

Furthermore, the *Plasmodium falciparum* challenge model may be used as to induce an antigen-specific immune response in humans. Human volunteers may be immunized using the transcutaneous immunization system containing oligopeptides or native proteins (i.e., polypeptides) derived from the malaria parasite, and then exposed to malaria experimentally or in the natural setting. The *Plasmodium yoelii* mouse malaria challenge model may be used to evaluate protection in the mouse against malaria (Wang et al., 1995).

Mice may be transcutaneously immunized with cholera toxin, or LT and then challenged intranasally with an LD70 dose (about 20 µg of cholera toxin) and observed for protection. Mallet et al. (personal communication) have found that C57BL/6 mice develop a fatal hemorrhagic pneumonia in response to intranasal challenge with CT. Alternatively, the mice may be challenged with an intraperitoneal dose of CT (Dragunsky et al., 1992). Cholera toxin-specific or LT specific IgG or IgA antibody may provide protection against cholera toxin challenge (Pierce, 1978; Pierce and Reynolds, 1974) and LT specific IgG or IgA is known to protect against ETEC related diarrheal disease.

Vaccination has also been used as a treatment for cancer, autoimmune disease, and allergies. For example, vaccination with a tumor antigen (e.g., prostate specific antigen) may induce an immune response in the form of antibodies, CTLs and lymphocyte proliferation which allows the body's immune system to recognize and kill tumor cells. Tumor antigens useful for vaccination have been described for melanoma (U.S. Pat. Nos. 5,102,663, 5,141,742, and 5,262,177), prostate carcinoma (U.S. Pat. No. 5,538,866), and lymphoma (U.S. Pat. Nos. 4,816,249, 5,068,177, and 5,227,159). Vaccination with T-cell receptor oligopeptide may induce an immune response that halts progression of auto-immune disease (U.S. Pat. Nos. 5,612,035 and 5,614,192; Antel et al., 1996; Vandenbark et al., 1996). U.S. Pat. Nos. 5,552,300 and 5,773,570 also describe antigens suitable for treating autoimmune disease.

A preferred embodiment of the formulation for genetic immunization is coating or covalently attaching polynucleotide (e.g., plasmid) to a solid substrate or microparticle (e.g., gold or tungsten particle, or other colloidal metals). The formulation may be delivered by a projectile gun (e.g., accelerated by expanding gas, voltage difference, magnetic repulsion) substantially under the stratum, but not into or through the dermis; preferably above or in the epidermis. If such a formulation is targeted to an antigen presenting cell for uptake (e.g., receptor-mediated phagocytosis), presentation of the encoded antigen may be facilitated or even enhanced.

The following is meant to be illustrative of the present invention; however, the practice of the invention is not limited or restricted in any way by the examples. Some of these results have been published by Glenn et al. (1998ab, 1999) and as WO98/20734.

EXAMPLES

Immunization Procedures

BALB/c or C57BL/6 mice of 6 to 8 weeks may be shaved on the dorsum, abdomen, or other anatomical sites with a #40 clipper. This shaving can usually be done without any signs of trauma to the skin. The shaving may be done from the mid-thorax to just above the base of the tail or to the nape of the neck, or the abdomen alone. The mice were then allowed to rest for about 24-48 hours. Prior to this, the mice may be ear tagged for identification, and a pre-bleed was obtained as a sample of pre-immune serum.

Immunization solution may be applied to a selected anatomical site of the subject at a dose between about 1 µl and about 200 µl, preferably between about 50 µl and about 100 µl. The solution may be applied to either an shaved dorsal/abdominal area or an ear of a mouse, or an arm, posterior auricular region, abdomen, or back of a human volunteer. As a control, mice may be given 25 µg cholera toxin in 200 µl of PBS by oral gavage.

Mice may be immunized as follows. Mice may be anesthetized with between about 0.03 ml and about 0.06 ml of a 20 mg/ml solution of xylazine (Phoenix Pharmaceuticals) and about 0.5 ml of 100 mg/ml ketamine (Parke-Davis) to prevent movement during immunization. Other anesthetic procedures may also be used such as, for example, inhalation of gas or vapor. Mice were immobilized by this dose of anesthesia for approximately one hour, or for only a few minutes or as long as several hours. Appropriate larger doses or repetition was used when immobilization for longer periods was needed (e.g., leaving immunizing solution on for about two or three hours). The mice were placed ventral side down on a warming pad.

The application site may or may not be swabbed with 70% isopropyl alcohol prior to wetting or immunization. For wetting, the immunizing solution may be placed on the shaved skin of a mouse by wiping with a saline-wetted sterile gauze to partially wet the skin (this allows even application of an immunizing solution and hydration of the application site). The solution may be placed on the skin after a period of a few minutes or immediately applied. A measured amount of the immunizing solution (between about 5 µl to about 200 µl) may be applied to an area of about 0.25 $cm^2$ to about 3 $cm^2$ of shaved skin with a pipet in accordance with the volume of solution to be applied. Alternatively, immunizing solution may be evenly applied to an ear. Care was used not to scrape or rub the skin with the pipet tip. The immunizing solution may be spread around the area to be covered with the smooth side of the pipet tip or simply allowed to spread on its own.

The immunizing solution may be left on the back of the mouse for between about 15 minutes and about two hours. The mouse may then be held gently by the nape of the neck and the tail under a copious stream of lukewarm tap water (about one liter), and washed. The mouse may then be gently patted dry with a piece of sterile gauze and a second washing may be performed. The mouse may be patted dry a second time and left in the cage. Immunization on the ear may be performed as described above except that it was not necessary to remove fur prior to immunization.

Infrequent adverse effects from the shaving, anesthesia, immunization, or washing procedures were observed. Neither erythema nor induration was generally seen at the immunization site for up to 72 hours after exposure to antigen. Some animals may develop a mild level of hyperkeratosis, including animals which were shaved and immunized as a negative control or with antigen alone. Some animals receiving adjuvant, antigen, or adjuvant plus antigen may develop a dermatitis which is generally very mild. Out of 55 human volunteers, there was only one subject who had an adverse effect (i.e., mild dermatitis beginning at the site of the patch adhesive). This was observed at the upper end of the dosage range, 500 µg LT.

Chemical Enhancement of Superficial Skin Penetration

Swabbing the skin with a treated or untreated swab is thought to physically and/or chemically remove superficial layers of and/or extract the stratum corneum, and thus enhance skin penetration. Alternatively, or in addition, such chemicals may activate and/or increase the local concentration of antigen presenting cells underlying the skin at the site of application. Swabs can be made of materials such as, for example, cotton, nylon, rayon and polyethylene. The mouse was allowed to rest for 24 hour after being shaved and prior to skin penetration enhancement. Enhancement was determined by reference to an aqueous solution (i.e., water only) which hydrates the skin.

Alcohol swabbing may act to physically and/or chemically enhance penetration of the skin. For procedures requiring alcohol swabbing, the back was wiped ten times (i.e., five times sweeping up the back towards the head, flip over the pad, and sweep back five times more) for about 10 seconds using an isopropyl pad. The alcohol was allowed to evaporate in about 5 minutes. Hydration was accomplished by gently rubbing the back with a sterile water-saturated gauze pad so as to form a pool of water on the back. After hydrating for about 5 minutes, the back was blotted dry with a gauze pad.

Detergent may also act as a skin penetration enhancer. The back was treated with 300 μl of 5% sodium dodecyl sulfate (SDS) for about 12 minutes and then followed by blotting off any excess SDS with a dry gauze pad. SDS can be applied to the skin in a carrier such as, for example, a pad and then any excess SDS can be removed with a dry gauze pad. The shaved and treated dorsum of the mouse was then hydrated as described above. Other surfactants, especially those that extract lipids from the stratum corneum may be used.

Another form of chemical penetration enhancer, a depilatory agent (e.g., calcium hydroxide or the like), may be used to enhance transcutaneous immunization. The back was treated with 100 μl of NAIR depilatory cream for about 12 minutes and then followed by wiping off the formulation with a gauze pad saturated in water. Such treatment can be performed for between about 0.1 minute to about 30 minutes, preferably about 20 minutes, and more preferably about 12 minutes. The shaved and treated dorsum of the mouse was then hydrated as described above.

Yet another chemical penetrant may be a keratinolytic agent (e.g., salicylate). The back was treated with a gauze pad saturated with a 10% salicylate suspension (one 325 mg tablet of aspirin dissolved in 3.25 ml of deionized water). Such treatment can continue for between about 0.1 minute to about 30 minutes, preferably about 20 minutes, and more preferably about 10 minutes. Approximately 10 minutes later, any remaining solution was blotted off, and the shaved and treated dorsum was then hydrated as described above.

Skin penetration enhancement is also described in *Pharmaceutical Skin Penetration Enhancement* (Walters and Hadgraft, Marcel Dekker, 1993).

Physical Enhancement of Superficial Skin Penetration

An abrasive (e.g., a common emery board) may be used to remove a portion of the stratum corneum (i.e., micro penetration). Twenty four hours after having the dorsum shaved, the back was either wiped with a gauze pad saturated in water, or brushed ten times with a medium grain emery board and then wiped with a gauze pad saturated in water. Approximately 5 minutes after the water treatment, any excess water was removed and immunizing solution was applied to the shaved and treated dorsum. Physical disruption of the outer surface of the skin with an emery board may enhance delivery of a solution for transcutaneous immunization.

Another device for physical penetration enhancement may be an abrasive pad which removes a portion of the stratum corneum and allows access to the underlying epidermis. Twenty four hours after having the dorsum shaved, the back was either wiped with a gauze pad saturated in water, or with a gauze pad saturated in water followed by rubbing for 10 seconds with a BUF PUF nylon sponge to remove the outermost layers of the stratum corneum. Excess water was removed and immunizing solution is applied to the shaved and treated dorsum. Physical disruption of the outer surface of the skin with an abrasive pad may enhance delivery of a solution for transcutaneous immunization.

Adhesive tape stripping may also remove superficial layers of the stratum corneum. Cellophane SCOTCH tape was applied to the back, bonding to the skin surface occurs over 3 minutes, and then followed by gentle removing of the tape. These bonding and removal steps were repeated three times. Physical disruption by tape stripping may enhance transcutaneous immunization by improving delivery of a solution for transcutaneous immunization. Tape stripping devices could be used in conjunction with other penetration enhancers, and may be dispersed in a roll or in individual units.

These simple devices could be replaced by other physical penetration enhancers to deliver an immunizing solution to the epidermis such as microneedles that are long enough to disrupt only the stratum corneum or superficial epidermis, devices used for tuberculin tine testing, abrading pads which have dissolvable crystals such as sucrose or sodium chloride or biodegradable polymers impregnated therein and rubbed on the skin, pneumatic guns which do not penetrate into the dermis, or other barrier disruption devices known to disrupt only the stratum corneum or superficial epidermis.

Liposome Preparation

Liposomes were prepared for use for transcutaneous immunization as multilamellar liposomes composed of dimyristoyl phosphatidyl choline, dimyristoyl phosphatidyl glycerol, and cholesterol according to Alving et al. (1993). Dimyristoyl phosphatidylcholine, dimyristoyl phosphatidylglycerol, and cholesterol were purchased from Avanti Polar Lipids (Alabaster, Ala.). Stock solutions of the lipids in chloroform were removed from storage in a freezer at −20° C.

Lipids were mixed in a molar ratio of 0.9:0.1:0.75 (dimyristoyl phosphatidyl choline, dimyristoyl phosphatidyl glycerol, and cholesterol respectively) in a pear-shaped flask. Using a rotary evaporator, solvent was removed at 37° C. under negative pressure for 10 minutes. The flask was further dried under low vacuum for two hours in a dessicator to remove residual solvent. Liposomes were swollen to a concentration of about 37 mM phospholipid using sterile water, lyophilized, and stored at −20° C. These liposomes were mixed in their lyophilized state with normal saline (pH 7.0) to achieve a designated phospholipid concentration in the saline. Alternatively, the dried lipids were swollen to make liposomes with normal saline (pH 7.0) and were not lyophilized.

Antigens and Adjuvants

The following may be used for immunization or immunoassay (e.g., immobilized for capture, competitor of antigen-specific binding): cholera toxin or CT (List Biologicals, Campbell, Calif., Cat #101B), CT B subunit (List Biologicals, Cat #BT01), CT A subunit (List Biologicals, Cat #102A), CT A subunit (Calbiochem, La Jolla, Calif., Cat #608562), pertussis toxin or PT (List Biologicals), tetanus fragment C or tetC (List Biologicals), tetanus toxoid (List Biologicals), tetanus toxin (List Biologicals), *Pseudomonas* exotoxin A or ETA (List Biologicals), diphtheria toxoid or DT (List Biologicals), *E. coli* heat-labile enterotoxin or LT (Sigma, St. Louis, Mo.), bovine serum albumin or BSA (Sigma, Cat #3A-4503), and *Hemophilus influenza* B polysaccharide conjugate or Hib-PS (Connaught, Swiftwater, Pa.). They were mixed with sterile buffered saline (e.g., PBS) or normal saline to dissolve.

ELISA—IgG (H+L)

Antibodies specific for the described antigens were determined using ELISA as described by Glenn et al. (1995). Antigen was dissolved in sterile saline at a concentration of about 2 µg/ml. Fifty microliters of this solution (0.1 µg) per well were put on an IMMULON-2 polystyrene plate (Dynatech, Chantilly, Va.) and incubated at room temperature overnight. The plate was then blocked with a 0.5% casein/0.05% TWEEN 20 detergent blocking buffer solution for about one hour. Serum was diluted with this casein diluent, and serial dilutions were done in columns on the plate. Incubation was for about two hours at room temperature.

The plate was then washed in a PBS-0.05% TWEEN 20 detergent wash solution four times, and goat anti-mouse IgG (H+L) horseradish peroxidase (HRP)-linked (Bio-Rad, Richmond, Calif., Cat #170-6516) enzyme-conjugated secondary antibody was diluted in casein diluent at a dilution of 1/500 and left on the plate for about one hour at room temperature. The plate was then washed four times in the PBS detergent wash solution. One hundred microliters of 2,2'-azino-di-(3-ethyl-benzthiazolone) sulphonic acid substrate (ABTS, Kirkegaard and Perry, Gaithersburg, Md.) were added to each well and the plate read at 405 nm after about 30 minutes of development. Results were reported as the geometric mean of individual sera and standard error of the mean of ELISA units (the inverse serum dilution at which the absorbance is equal to 1.0) or as individual antibody responses in ELISA units. In all cases, the ELISA assays were conducted to discount the role of cross-reactivity between co-administered antigens.

ELISA—IgG($\gamma$), IgM($\mu$), and IgA($\alpha$)

IgG($\gamma$), IgM($\mu$) and IgA($\alpha$) isotype antibody levels were determined using ELISA as described above, with certain exceptions. Goat anti-mouse IgG($\gamma$) HRP-linked (Bio-Rad, Richmond, Calif., Cat #172-1038), goat anti-mouse IgM($\mu$) HRP-linked (Bio-Rad, Cat #172-1030), or goat anti-mouse IgA (Zymed, South San Francisco, Calif.) enzyme-conjugated secondary antibody was diluted in casein diluent at a dilution of 1/1000.

ELISA—IgG Subclasses

Antigen-specific IgG (IgG1, IgG2a, IgG2b, and IgG3) subclass antibody against antigen was determined as described above, with certain exceptions. Serum was incubated at room temperature for about four hours to IMMULON-2 polystyrene plates that had been coated with antigen and then blocked.

Enzyme-conjugated secondary antibody was horseradish peroxidase (HRP)-conjugated goat anti-mouse isotype-specific antibody (IgG1, IgG2a, IgG2b, IgG3, The Binding Site, San Diego, Calif.). A standard curve for each subclass was determined using mouse myeloma IgG1, IgG2a, IgG2b, and IgG3 (The Binding Site). Standard wells were coated with goat anti-mouse IgG (H+L) (Bio-Rad, Richmond, Calif., Cat #172-1054) to capture the myeloma IgG subclass standards which were added in serial dilutions. The myeloma IgG subclass was also detected using the HRP-conjugated goat anti-mouse subclass-specific antibody. Both the serum and myeloma standards were detected using 2,2'-azino-di-(3-ethyl-benzthiazolone) sulphonic acid (ABTS, Kirkegaard and Perry, Gaithersburg, Md.) as substrate. Absorbances were read at 405 nm after about 30 minutes of development. Individual antigen specific subclasses were quantitated using the values from the linear titration curve computed against the myeloma standard curve and then reported as µg/ml.

ELISA—IgE

Antigen-specific IgE antibody quantitation was performed using a protocol from Pharmingen Technical Protocols, page 541 of the Research Products Catalog, 1996-1997 (Pharmingen, San Diego, Calif.). Fifty microliters of 2 µg/ml purified anti-mouse IgE capture mAb (Pharmingen, Cat #02111D) in 0.1 M NaHCO$_3$ (pH 8.2) were added to an IMMUNO plate (Nalge Nunc, Rochester, N.Y., Cat #12-565-136). The plate was incubated overnight at room temperature, washed three times with PBS-TWEEN 20 detergent wash solution, blocked with 3% BSA in PBS for about two hours, and washed three times with wash solution. Serum was diluted 1/100 in 1% BSA in PBS, and serially diluted down the columns of the plate (e.g., 1/100, 1/200, et cetera). Purified mouse IgE standards (Pharmingen, Cat #0312D) were added with a starting dilution of 0.25 µg/ml and serially diluted down the columns of the plate. The plate was incubated for about two hours and washed five times with wash solution.

Biotinylated anti-mouse IgE monoclonal antibody (Pharmingen, Cat #02122D) at 2 µg/ml in 1% BSA in PBS was incubated for about 45 minutes and washed five times with wash solution. Avidin-peroxidase (Sigma, St. Louis, Mo., Cat #A3151) at a 1:400 dilution of a 1 mg/ml solution was incubated for about 30 minutes, and then washed six times with wash solution. Serum and IgE standards were detected using 2,2'-azino-di-(3-ethyl-benzthiazolone) sulphonic acid (ABTS, Kirkegaard and Perry, Gaithersburg, Md.) as substrate. Absorbances were read at 405 nm after about 30 minutes of development. Individual antigen specific subclasses were quantitated using the values from the linear titration curve computed against the IgE standard curve and reported as µg/ml.

Toxin Challenge

Mice were anesthetized with xylazine:ketamine and then challenged intranasally with 20 µl CT (Calbiochem, La Jolla, Calif.) at 1 mg/ml in 10 mM TRIS buffer (pH 7.5). Mice were challenged under anesthesia by intranasally administering 20 µg in 20 µl buffer divided equally between each nare. Following challenge, mice were observed daily with both morbidity and mortality recorded.

Lung Washes and Stool Collection

Lung washes were obtained after sacrificing the mouse on the day of challenge. The trachea was transected, a 22 gauge polypropylene tube was inserted, and PBS infused to gently inflate the lungs. The wash solution was withdrawn, reinfused for a total of three cycles, and then stored frozen at −20° C. until assayed.

Stool pellets were collected the day before challenge after spontaneous defecation. Pellets were weighed, homogenized in 1 ml of PBS per 100 µg fecal material, and centrifuged. The supernatant was collected and then stored frozen at −20° C. until assayed.

Human Anti-LT Antibody

Anti-LT IgG titer was determined as described by Svennerholm et al. (1983). A 96-well plate (Type-Russell) was coated overnight with monosialoganglioside-G$_{M1}$ (Sigma, St. Louis, Mo.) of LT, and blocked with 5% dry milk in PBS-0.05% TWEEN 20 solution. Antibody responses were detected using goat anti-human IgG($\gamma$)-HRP (Kirkegaard and Perry, Gaithersburg, Md.) enzyme-conjugated secondary antibody and 2,2'-azino-di-(3-ethyl-benzthiazolone) sulphonic acid (ABTS, Kirkegaard and Perry) as substrate. The plate was read at 405 nm after 30 minutes of development. Results were reported in ELISA units (EU) which were defined as the inverse dilution of sample which yields an OD of 1.0. Anti-LT IgA was determined in the same manner as anti-LT IgG except that goat anti-human IgA(α)-HRP (Kirkegaard and Perry) was used as enzyme-conjugated secondary antibody and ODs were plotted against a standard IgA curve yielding results expressed in ng/ml. The standard IgA curve and total serum IgA were determined by using unlabeled goat anti-human IgA (Kirkegaard and Perry) followed by blocking as above and then application of serial dilutions of IgA standard.

Cellular Immunity

Specific cellular immunity may be detected by assaying for antibody secretion (e.g., ELISA, plaque formation), T-cell proliferation (e.g., thymidine incorporation), or CTL killing (e.g., precursor frequency, chromium release from sensitized targets) specific for antigen in lymphocytes obtained from lymphoid tissues (e.g., appendix, gut, Peyers patches, tonsils, bronchi, NALT, lymph nodes, spleen, thymus, blood, bone marrow). Lymphocytes may also be analyzed by detecting the presence of markers, high or low, that are related to cellular function or differentiation (e.g., cluster of differentiation antigens like CD2, CD3, CD4, CD8, CD28, CD34, CD45, CD79a/b, CDw90; adhesion molecules; homing receptors; antigen receptors Ig or Tcr, and their constant region isotypes). The involvement of regional immunity, especially mucosal immunity, may be determined by examining peripheral immune organs associated with mucosal immunity (e.g., Peyers patches, BALT, GALT, NALT), detecting antigen-specific lymphocytes with appropriate markers (e.g., CD antigens, homing receptors for spleen and regional lymph nodes), or challenge with an infective pathogen.

Statistical Analysis

Unless otherwise indicated, data were represented as geometric means and SEM. Antibody titers in groups were compared using either paired or unpaired, one-tailed Student t tests with p values <0.05 regarded as significant. For challenge studies, the groups were compared by the Fisher Exact test (SigmaStat, SPSS, Chicago, Ill.).

Standard techniques in the art are described in *Current Protocols in Immunology* (Coligan et al., Wiley, updated to 1999); *Antibodies and Using Antibodies* (Harlow and Lane, CSHL Press, 1988 and 1999); *Current Protocols in Protein Science* (Coligan et al., Wiley, 1998); *Strategies for Protein Purification and Characterization* (Marshak et al., CSHL Press, 1996); and *Protein Purification, Principles, High Resolution Methods, and Applications* (Janson and Ryder, Wiley, 1997); *Current Protocols in Molecular Biology* (Ausubel et al., Wiley, updated to 1999); Sambrook et al., *Molecular Cloning*, CSHL Press, 1989); *Cells* (Spector et al., CSHL, 1998); and *The Biomedical Engineering Handbook* (Bronzino, CRC Press, 1995).

Example 1

BALB/c mice at 6 to 8 weeks of age were immunized transcutaneously as described above in groups of five mice. Mice were immunized using 100 µl of immunization solution, which was comprised of liposomes prepared as described above by mixing with saline. The pre-formed liposomes were then diluted in either saline ("Liposomes" only group) or with CT in saline to yield an immunizing solution containing liposomes at 10 mM to 150 mM phospholipid with 100 µg CT per 100 µl of immunizing solution. CT was mixed in saline to make an immunizing solution containing 100 µg CT per 100 µg of solution for the group receiving CT alone. Solutions were vortexed for 10 seconds prior to immunization.

The mice were immunized transcutaneously at 0 and 3 weeks. Antibody levels were determined as described above for "ELISA IgG(H+L)" on serum collected three weeks after the boosting immunization, and compared against pre-immune sera. As shown in Table 1, the level of anti-CT antibodies induced by CT without liposomes was not different from the level of anti-CT antibodies generated using liposomes except in the mice where 150 mM Liposomes were used. CT in saline alone was able to immunize mice against CT to produce high antibody titers.

TABLE 1

| Anti-CT Antibodies | | |
| --- | --- | --- |
| Group | ELISA Units | SEM |
| CT alone | 27,482 | (16,635 – 48,051) |
| CT + 150 mM Liposomes | 4,064 | (2,845 – 5,072)* |
| CT + 100 mM Liposomes | 35,055 | (25,932 – 44,269) |
| CT + 50 mM Liposomes | 9,168 | (4,283 – 12,395) |
| CT + 25 mM Liposomes | 18,855 | (12,294 – 40,374) |
| CT + 10 mM Liposomes | 28,660 | (18,208 – 31,498) |
| 50 mM Liposomes | 0 | |

*Significantly different from the group "CT alone" ($p < 0.05$)

Example 2

BALB/c mice at 6 to 8 weeks of age were immunized transcutaneously as described above in groups of five mice. Mice were immunized at 0 and 3 weeks using 100 µl of immunization solution prepared as follows: BSA was mixed in saline to make an immunizing solution containing 200 µg BSA per 100 µl of saline for the group receiving BSA alone; BSA and CT were mixed in saline to make an immunizing solution containing 200 µg BSA and 100 µg CT per 100 µl of saline for the group receiving BSA and CT. Where liposomes were used, the liposomes were prepared as described above, and were first mixed with saline to form liposomes. They were then diluted in BSA or BSA and CT in saline to yield an immunizing solution containing liposomes at 50 mM phospholipid with 200 µg BSA per 100 µl of immunizing solution, or 200 µg BSA+100 µg CT per 100 µl of immunizing solution. Solutions were vortexed for 10 seconds prior to immunization.

The antibodies were determined using "ELISA IgG(H+L)" as described above on serum collected three weeks after the second immunization. The results are shown in Table 2. BSA alone, with or without liposomes, was not able to elicit an antibody response. The addition of CT, however, stimulated an immune response to BSA. CT acted as a adjuvant for the immune response to BSA, and anti-BSA antibodies of high titer were produced.

TABLE 2

| Anti-BSA Antibodies | | |
| --- | --- | --- |
| Group | ELISA Units | SEM |
| BSA in saline | 0 | |
| BSA + 50 mM Liposomes | 0 | |
| CT + BSA in saline | 8,198 | (5,533 – 11,932) |
| CT + BSA + 50 mM | 3,244 | (128 – 3,242) |

Example 3

BALB/c mice at 6 to 8 weeks of age were immunized transcutaneously as described above in groups of five mice. Mice were immunized at 0 and 3 weeks using 100 μl of immunization solution prepared as follows: LT was mixed in saline to make an immunizing solution containing 100 μg of LT per 100 μl of saline for the group receiving LT alone. Where liposomes were used, they were prepared as described above and first mixed with saline to form the liposomes. The pre-formed liposomes were then diluted in LT in saline to yield an immunizing solution containing liposomes at 50 mM phospholipid with 100 μg of LT per 100 μl of immunizing solution. Solutions were vortexed for 10 seconds prior to immunization.

The anti-LT antibodies were determined using ELISA as described above three weeks after the second immunization. The results are shown in Table 3. LT was clearly immunogenic both with and without liposomes, and no significant difference between the groups could be detected. LT and CT are members of the family of bacterial ADP-ribosylating exotoxins (bAREs). They are organized as A:B proenzymes with the ADP-ribosyltransferase activity contained in the A subunit and the target cell binding a function of the B subunit. LT is 80% homologous with CT at the amino acid level and has a similar non-covalently bound subunit organization, stoichiometry (A:B5), the same binding target, ganglioside GM1, and is similar in size (MW ~80,000). The similarities of LT and CT appear to influence their immunogenicity by the transcutaneous route as reflected by the similar magnitude of the antibody response to both CT and LT (cf. Tables 1 and 3).

TABLE 3

| Anti-LT Antibodies | | |
|---|---|---|
| Group | ELISA Units | SEM |
| LT in saline | 23,461 | (20,262 – 27,167) |
| LT + 50 mM Liposomes | 27,247 | (19,430 – 38,211) |

Example 4

C57BL/6 mice at 6 to 8 weeks of age were immunized transcutaneously in groups of five mice. The mice were immunized once using 100 μl of immunization solution prepared as follows: LT was mixed in saline to make an immunizing solution containing 100 μg of LT per 100 μl of saline. The solution was vortexed for 10 seconds prior to immunization.

The anti-LT antibodies were determined using "ELISA IgG (H+L)" as described above three weeks after the single immunization. The results are shown in Table 4. LT was clearly immunogenic with a single immunization and antibodies were produced by 3 weeks. Rapid enhancement of antibody titers and responses to single immunization would be a useful aspect of the transcutaneous immunization method. It is conceivable that a rapid single immunization would be useful in epidemics, for travelers, and where access to medical care is poor.

TABLE 4

| Anti-LT Antibodies | |
|---|---|
| Mouse Number | ELISA Units |
| 5141 | 6,582 |
| 5142 | 198 |
| 5143 | 229 |
| 5144 | 6,115 |
| 5145 | 17,542 |
| Geo Mean | 2,000 |

Example 5

C57BL/6 mice at 8 to 12 weeks of age were immunized transcutaneously as described above in groups of five mice. The mice were immunized once using 100 μl of immunization solution prepared as follows: CT was mixed in saline to make an immunizing solution containing 100 μg CT per 100 μl of saline. The solution was vortexed for 10 seconds prior to immunization.

The anti-CT antibodies were determined using "ELISA IgG (H+L)" as described above three weeks after the single immunization. The results are shown in Table 5. CT was highly immunogenic with a single immunization. Rapid enhancement of antibody titers and responses to single immunization may be a useful aspect of the transcutaneous immunization method. It is conceivable that a rapid single immunization would be useful in epidemics, for travelers, and where access to medical care is poor.

TABLE 5

| Anti-CT Antibodies | |
|---|---|
| Mouse Number | ELISA Units |
| 2932 | 18,310 |
| 2933 | 30,878 |
| 2934 | 48,691 |
| 2935 | 7,824 |
| Geo Mean | 21,543 |

Example 6

BALB/c mice at 6 to 8 weeks of age were immunized transcutaneously as described above in groups of five mice. The mice were immunized at 0 and 3 weeks using 100 μl of immunization solution prepared as follows: ETA was mixed in saline to make an immunizing solution containing 100 μg ETA per 100 μl of saline for the group receiving ETA alone. Where Liposomes were used, the liposomes were prepared as described above, and first mixed with saline to form the liposomes. The pre-formed liposomes were then diluted with ETA in saline to yield an immunizing solution containing liposomes at 50 mM phospholipid with 100 μg of ETA per 100 μl of immunizing solution. Solutions were vortexed for 10 seconds prior to immunization.

The antibodies were determined using "ELISA IgG(H+L)" as described above on serum collected three weeks after the second immunization. The results are shown in Table 6. ETA was clearly immunogenic both with and without liposomes, and no significant difference between the groups could be detected. ETA differs from CT and LT in that ETA is a single 613 amino acid peptide with A and B domains on the same peptide and binds to an entirely different receptor, the α2-macroglobulin receptor/low density lipoprotein receptor-related protein (Kounnas et al., 1992). Despite the dissimilarities between ETA and CT in size, structure, and binding target, ETA also induced a transcutaneous antibody response.

TABLE 6

Anti-ETA Antibodies

| Group | ELISA Units | SEM |
|---|---|---|
| ETA in saline | 3,756 | (1,926 – 7,326) |
| ETA + 50 mM Liposomes | 857 | (588 – 1,251) |

Example 7

BALB/c mice at 6 to 8 weeks of age were immunized transcutaneously as described above in groups of five mice. The mice were immunized using 100 μl of immunization solution which was prepared as follows: CT was mixed in saline to make 100 μg CT per 100 μl of immunizing solution, LT was mixed in saline to make 100 μg LT per 100 μl of immunizing solution, ETA was mixed in saline to make 100 μg ETA per 100 μl of immunizing solution, and CT and BSA were mixed in saline to make 100 μg CT per 100 μl of immunizing solution and 200 μg BSA per 100 μl of immunizing solution. Solutions were vortexed for 10 seconds prior to immunization.

The mice were immunized transcutaneously at 0 and 3 weeks. The antibody levels were determined using "ELISA IgG Subclasses" as described above on serum collected three weeks after the boosting immunization and compared against the pre-immune sera. The IgG subclass response to CT, BSA, and LT had similar levels of IgG1 and IgG2a reflecting activation of T help from both Th1 and Th2 lymphocytes (Seder and Paul, 1994), whereas the IgG subclass response to ETA consisted of almost exclusively IgG1 and IgG3, consistent with a Th2-like response (Table 7). Thus, it appears that all IgG subclasses can be produced using transcutaneous immunization.

TABLE 7

IgG Subclasses of Induced Antibodies

| Imm. Antigen | Antibody Specificity | IgG1 (μg/μl) | IgG2a (μg/μl) | IgG2b (μg/μl) | IgG3 (μg/μl) |
|---|---|---|---|---|---|
| CT | CT | 134 | 25 | 27 | 0 |
| CT + BSA | BSA | 108 | 17 | 12 | 5 |
| LT | LT | 155 | 28 | 10 | 8 |
| ETA | ETA | 50 | 0 | 1 | 10 |

Example 8

BALB/c mice at 6 to 8 weeks of age were immunized transcutaneously as described above in groups of five mice. The mice were immunized using 100 μl of immunization solution which was prepared as follows: LT was mixed in saline to make an immunizing solution containing 100 μg LT per 100 μl of saline for the group receiving LT alone, CT was mixed in saline to make an immunizing solution containing 100 μg CT per 100 μl of saline for the group receiving CT alone, ETA was mixed in saline to make an immunizing solution containing 100 μg ETA per 100 μl of saline for the group receiving ETA alone, and BSA and CT were mixed in saline to make an immunizing solution containing 100 μg BSA and 100 μg CT per 100 μl of saline for the group receiving BSA and CT.

The mice were immunized transcutaneously at 0 and 3 weeks. The antibody levels were determined using "ELISA IgE" as described above on serum collected one week after the boosting immunization and compared against the pre-immune sera. As shown in Table 8, no IgE antibodies were found although the sensitivity of detection for the assay was about 0.003 μg/ml. IgG antibodies were determined in the same mice using "ELISA IgG(H+L)" as described above on serum collected three weeks after the second immunization. The IgG antibody response to LT, ETA, CT and BSA are shown to indicate that the animals were successfully immunized and responded with high titers of antibodies to the respective antigens.

TABLE 8

IgE Antibodies to LT, ETA, CT and BSA

| Group | Antibody Specificity | IgE (μg/ml) | IgG (ELISA Units) |
|---|---|---|---|
| LT | Anti-LT | 0 | 23,461 |
| ETA | Anti-ETA | 0 | 3,756 |
| CT | Anti-CT | 0 | 39,828 |
| CT + BSA | Anti-BSA | 0 | 8,198 |

Example 9

BALB/c mice at 6 to 8 weeks of age immunized transcutaneously as described above in groups of five mice. The mice were immunized at 0 and 3 weeks using 100 ml of immunization solution which was prepared as follows: CT was mixed in saline to make an immunizing solution containing 100 mg CT per 100 ml of immunizing solution. The immunization solution was vortexed for 10 seconds prior to immunization.

The mice were immunized transcutaneously at 0 and 3 weeks. The antibody levels were determined using "ELISA IgG(H+L)" and "ELISA IgG(γ)" as described above. Determinations were done at 1 and 4 weeks after the initial immunization, and compared against the pre-immune sera. As shown in Table 9, high levels of anti-CT IgG(γ) antibodies were induced by CT in saline. Small amounts of IgM could be detected by using IgM(μ) specific secondary antibody. By 4 weeks, the antibody response was primarily IgG. Data are reported in ELISA units.

TABLE 9

IgG(γ) and IgM(μ)

| Imm. Group | Week | IgG(γ) | IgM(μ) |
|---|---|---|---|
| CT | 1 | 72 | 168 |
| CT | 4 | 21,336 | 38 |
| L0 + CT | 1 | 33 | 38 |
| L0 + CT | 4 | 22,239 | 70 |

Example 10

BALB/c mice at 6 to 8 weeks of age were immunized transcutaneously as described above in groups of five mice. The mice were immunized once using 100 μl of immunization solution prepared as follows: CT was mixed in saline to make an immunizing solution containing 100 μg CT per 100 μl of saline. The solution was vortexed for 10 seconds prior to immunization. The mice were immunized transcutaneously at 0 and 3 weeks. Antibody levels were determined using "ELISA IgG (H+L)" as described above on serum collected five weeks after the boosting immunization, and compared against pre-immune sera. As shown in Table 10, serum anti-CT IgA antibodies were detected.

TABLE 10

Anti-CT IgA Antibodies

| Mouse Number | IgA (ng/ml) |
|---|---|
| 1501 | 232 |
| 1502 | 22 |
| 1503 | 41 |
| 1504 | 16 |
| 1505 | 17 |

Example 11

BALB/c mice at 6 to 8 weeks of age were immunized transcutaneously as described above in groups of five mice. The mice were immunized using 100 µl of immunization solution which was prepared as follows: CT was mixed in saline to make an immunizing solution containing 100 µg CT per 100 µl of immunizing solution. The immunization solution was vortexed for 10 seconds prior to immunization.

The mice were immunized with 100 µl of immunizing solution transcutaneously at 0 and 3 weeks. The antibody levels were determined using "ELISA IgG(H+L)" and "ELISA IgG(γ)" as described above. Antibody determinations were done at 8 weeks after the initial immunization and compared against the pre-immune sera. As shown in Table 11, high levels of serum anti-CT antibodies were induced by CT in saline. Lung wash IgG could be detected by ELISA using IgG(H+L) or IgG(γ) specific antibody. The antibody found on the lung mucosal surface is diluted by the lavage method used to collect mucosal antibody and, thus, the exact amounts of antibody detected are not as significant as the mere presence of detectable antibody.

Lung washes were obtained after sacrificing the mouse. The trachea and lungs were exposed by gentle dissection and trachea was transected above the bifurcation. A 22 gauge polypropylene tube was inserted and tied off on the trachea to form a tight seal at the edges. Half a milliliter of PBS was infused using a 1 ml syringe attached to the tubing and the lungs were gently inflated with the fluid. The fluid was withdrawn and reinfused for a total of three rounds of lavage. The lung wash was then frozen at −20° C.

Table 11 shows the IgG(H+L) and IgG(γ) antibody response to cholera toxin in the sera and lung washes at 8 weeks. Data are expressed in ELISA units. Antibodies were clearly detectable for all mice in the lung washes. The presence of antibodies in the mucosa may be important for protection against mucosally active diseases.

TABLE 11

Mucosal Antibody to CT

| Animal# | Imm. Group | IgG(H + L) | IgG(γ) | Source |
|---|---|---|---|---|
| 1501 | CT | 133 | 34 | Lungs |
| 1502 | CT | 75 | 12 | Lungs |
| 1503 | CT | 162 | 28 | Lungs |
| 1504 | CT | 144 | 18 | Lungs |
| 1505 | CT | 392 | 56 | Lungs |
|  | Geo Mean | 156 | 26 |  |
| 1501 | CT | 34,131 | 13,760 | Sera |
| 1502 | CT | 11,131 | 2,928 | Sera |
| 1503 | CT | 21,898 | 10,301 | Sera |

TABLE 11-continued

Mucosal Antibody to CT

| Animal# | Imm. Group | IgG(H + L) | IgG(γ) | Source |
|---|---|---|---|---|
| 1504 | CT | 22,025 | 8,876 | Sera |
| 1505 | CT | 34,284 | 10,966 | Sera |
|  | Geo Mean | 23,128 | 8,270 |  |

Example 12

BALB/c mice were immunized transcutaneously at 0 and 3 weeks as described above in groups of four mice. Liposomes were prepared as described above, and were first mixed with saline to form the liposomes. The pre-formed liposomes were then diluted with either CT, CTA or CTB in saline to yield an immunizing solution containing liposomes at 50 mM phospholipid with 50 µg of antigen (CT, CTA or CTB) per 100 µl of immunizing solution. Solutions were vortexed for 10 seconds prior to immunization.

The antibodies were determined using "ELISA IgG(H+L)" as described above on serum collected one week after the boosting immunization and compared against the pre-immune sera. The results are shown in Table 12. CT and CTB were clearly immunogenic whereas CTA was not. Thus, the B subunit of CT is necessary and sufficient to induce a strong antibody response.

TABLE 12

Antibodies to CT, CTA and CTB

| Group | Anti-CT | Anti-CTA | Anti-CTB |
|---|---|---|---|
| CT + 50 mM Liposomes | 12,636 | 136 | 7,480 |
| CTB + 50 mM Liposomes | 757 | 20 | 1,986 |
| CTA + 50 mM Liposomes | 0 | 0 | 0 |

Example 13

BALB/c mice were immunized transcutaneously as described above in groups of five mice. Mice were immunized at 0 and 3 weeks with 100 µg of diphtheria toxoid (DT) and 10 µg pertussis toxin (PT) per 100 µl of saline solution. Solutions were vortexed for 10 seconds prior to immunization.

The antibodies were quantitated using "ELISA IgG(H+L)" as described above. Anti-diphtheria toxoid antibodies were detected only in animals immunized with both pertussis toxin and diphtheria toxoid. The highest responder had anti-diphtheria toxoid antibody ELISA units of 1,038. Thus, a small amount of pertussis toxin acts as an adjuvant for diphtheria toxoid antigen. The toxoid alone did not induce an immune response suggesting that the toxoiding process has affected the portion of the molecule responsible for the adjuvant effects found in the ADP-ribosylating exotoxin.

TABLE 13

Antibody to Diphtheria Toxoid

| Mouse Number | Immunizing Antigen | IgG ELISA Units |
|---|---|---|
| 4731 | DT + PT | 1,039 |
| 4732 | DT + PT | 1 |
| 4733 | DT + PT | 28 |
| 4734 | DT + PT | 15 |

TABLE 13-continued

Antibody to Diphtheria Toxoid

| Mouse Number | Immunizing Antigen | IgG ELISA Units |
|---|---|---|
| 4735 | DT + PT | 20 |
| 4621 | DT | 0 |
| 4622 | DT | 0 |
| 4623 | DT | 0 |
| 4624 | DT | 0 |
| 4625 | DT | 0 |

Example 14

BALB/c mice were immunized transcutaneously as described above in groups of five mice. Mice were immunized once at 0, 8 and 20 weeks with 50 µg of pertussis toxin (List Biologicals, catalog #181, lot #181-20a) per 100 µl of saline solution.

The antibodies were quantitated using "ELISA IgG(H+L)" as described above. Anti-pertussis toxin antibodies were detected one week after the last boost in animals immunized with pertussis. All five animals had elevated levels of anti-pertussis toxin antibody after the last immunization. Thus, pertussis toxin acts as an adjuvant for itself and induces PT-specific PT-specific IgG antibodies. The adjuvant effect of PT may be useful in combination vaccines such as Diphtheria/Pertussis/Tetanus/Hib-PS in enhancing the antibody response to co-administered antigens as well as to PT itself.

TABLE 14

Antibody Response to Pertussis Toxin

| Mouse Number | Antigen | 2 Weeks | 21 Weeks |
|---|---|---|---|
| 5156 | PT | 14 | 256 |
| 5157 | PT | 22 | 330 |
| 5158 | PT | 17 | 303 |
| 5159 | PT | 33 | 237 |
| 5160 | PT | 75 | 418 |

Example 15

BALB/c mice were immunized transcutaneously as described above in groups of five mice. Mice were immunized once at 0 weeks with 50 µg tetanus toxoid and 100 µg cholera toxin per 100 µl of saline solution. The antibodies were quantitated using "ELISA IgG(H+L)" as described above. Anti-tetanus toxoid antibodies were detected at 8 weeks in animal 5173 at 443 ELISA units.

Example 16

The possibility that oral immunization occurred through grooming after epicutaneous application and subsequent washing of the site of application was evaluated using $^{125}$I-labeled CT to track the fate of the antigen/adjuvant. Mice were anesthetized, transcutaneously immunized as described above with 100 ng of $^{125}$I-labeled CT (150,000 cpm/µg CT). Control mice remained anesthetized for six hours to exclude grooming, and experimental mice were anesthetized for one hour and then allowed to groom after washing. Mice were sacrificed at six hours and organs weighed and counted for $^{125}$I on a Packard gamma counter. A total of about 2-3 µg of CT was detected on the shaved skin at the site of immunization (14,600 cpm/µg tissue) while a maximum of 0.5 µg of CT was detected in the stomach (661 cpm/µg tissue) and intestine (9 cpm/µg tissue).

Oral immunization (n=5) with 10 µg of CT in saline at 0 and 3 weeks (without NaHCO$_3$) induced a 6 week mean IgG antibody response of <1,000 ELISA units whereas transcutaneous immunization with 100 µg CT, shown above to result in less than 5 µg CT retained in the skin after washing, resulted in an anti-CT response of 42,178 ELISA units at 6 weeks. Induction of an immune response to orally fed CT requires the addition of NaHCO$_3$ to the immunizing solution (Pierce, 1978; Lycke and Holmgren, 1986). Thus, oral immunization does not significantly contribute to the antibodies detected when CT is applied epicutaneously to the skin.

Example 17

Skin of the mouse ear is frequently used for studies of LC activation and is an excellent site for transcutaneous immunization. Langerhans cell (LC) activation in mice using contact sensitizers, LPS, and proinflammatory cytokines is characterized by both changes in morphology and through elevations in surface marker expression.

In vivo evidence of Langerhans cell activation was obtained using cholera toxin (CT) in saline applied epicutaneously to the skin, specifically the ears of the mouse, where large populations of Langerhans cells can be readily visualized (Enk et al., 1993; Bacci et al., 1997), and staining for major histocompatibility complex (MHC) class II molecules which is upregulated in activated Langerhans cells (Shimada et al., 1987).

BALB/c (H-2$^d$) mouse ears were coated on the dorsal side with either 100 µg CT in saline, 100 µg CTB in saline, saline alone, or an intradermal injection of the positive controls 100 µg LPS or 10 µg TNF-α, for one hour while the mouse was anesthetized. The ears were then thoroughly washed and, the next day, the ears were removed and epidermal sheets were harvested and stained for MHC class II expression as described by Caughman et al (1986). Epidermal sheets were stained with MKD6 (anti-I-A$^d$) or negative control Y3P (anti-I-A$^k$), and goat anti-mouse FITC F(ab)$_2$ was used as a second step reagent. Mice transcutaneously immunized on the ear (as described above, but without shaving) had previously been found to have anti-CT antibodies of 7,000 ELISA units three weeks after a single immunization.

CT induced an enhancement of major histocompatibility complex (MHC) class II expression on Langerhans cells (LC), changes in LC morphology (loss of dendritic processes, enlarged cell bodies, and intense staining of the cells), and loss of LCs in the epidermal sheets (presumably through migration). These are features of LC activation. Enhanced expression of MHC class II molecules as detected by staining intensity, reduced numbers of Langerhans cells (especially with cholera toxin), and changes in Langerhans cell morphology were found in the epidermal sheets of the mice immunized with CT and CTB comparable to controls, suggesting that Langerhans cells were activated by the epicutaneously applied cholera toxin (Aiba and Katz, 1990; Enk et al., 1993). LC from CT-treated skin may also express increased levels CD86 (B7-2) and decreased levels of E-cadherin, which are consistent with LC activation. The LC-activating potential of CT may be confirmed using flow cytometry.

Example 18

Langerhans cells represent the epidermal contingent of a family of potent accessory cells termed 'dendritic cells'.

Langerhans cells (and perhaps related cells in the dermis) are thought to be required for immune responses directed against foreign antigens that are encountered in skin. The 'life cycle' of the Langerhans cell is characterized by at least two distinct stages. Langerhans cells in epidermis (the 'sentinels') can ingest particulates and process antigens efficiently, but are weak stimulators of unprimed T cells. In contrast, Langerhans cells that have been induced to migrate to lymph nodes after contact with antigen in epidermis (the 'messengers') are poorly phagocytic and have limited antigen-processing capabilities, but are potent stimulators of naive T cells. If Langerhans cells are to fulfill both their 'sentinel' and 'messenger' roles, they must be able to persist in epidermis, and also be able to exit epidermis in a controlled fashion after exposure to antigen. Thus, regulation of Langerhans cell-keratinocyte adhesion represents a key control point in Langerhans cell trafficking and function.

Langerhans cells express E-cadherin (Blauvelt et al., 1995), a homophilic adhesion molecule that is prominently represented in epithelia. Keratinocytes also express this adhesion molecule, and E-cadherin clearly mediates adhesion of murine Langerhans cells to keratinocytes in vitro. It is known that E-cadherin is involved in the localization of Langerhans cells in epidermis. See Stingl et al. (1989) for a review of the characterization and properties of Langerhans cells and keratinocytes.

The migration of epidermal Langerhans cells (LC) and their transport of antigen from the skin to draining lymph nodes are known to be important in the induction of cutaneous immune responses, such as contact sensitization. While in transit to the lymph nodes, Langerhans cells are subject to a number of phenotypic changes required for their movement from the skin and acquisition of the capacity for antigen presentation. In addition to the upregulation of MHC class II molecules, are alterations in the expression of adhesion molecules that regulate interactions with the surrounding tissue matrix and with T lymphocytes. The migration of the Langerhan cell is known to be associated with a marked reduction in the expression of E-cadherin (Schwarzenberger and Udey, 1996), and a parallel upregulation of ICAM-1 (Udey, 1997).

Transcutaneous immunization with bacterial ADP ribosylating exotoxins (bARE's) target the Langerhans cells in the epidermis. The bAREs activate the Langerhans cell, transforming it from its sentinel role to its messenger role. Ingested antigen is then taken to the lymph node where it is presented to B and T cells (Streilein and Grammer, 1989; Kripke et al., 1990; Tew et al., 1997). In the process, the epidermal Langerhans cell matures into an antigen-presenting dendritic cell in the lymph node (Schuler and Steinman, 1985); lymphocytes entering a lymph node segregate into B-cell follicles and T-cell regions. The activation of the Langerhans cell to become a migratory Langerhans cell is known to be associated with not only a marked increase in MHC class II molecules, but also marked reduction in the expression of E-cadherin, and upregulation of ICAM-1.

We envision that cholera toxin (CT) and its B subunit (CTB) might upregulate the expression of ICAM-1 and downregulate the expression of E-cadherin on Langerhans cells as well as upregulate the expression of MHC class II molecules on the Langerhans cell. CT or CTB acts as an adjuvant by freeing the sentinel Langerhans cell to present antigens such as BSA or diphtheria toxoid phagocytosed by the Langerhans cell at the same location and time as the encounter with the CT or CTB when they are acting as adjuvant. The activation of a Langerhans cells to upregulate the expression of ICAM-1 and downregulate the expression of E-cadherin may be mediated by cytokine release including TNF-α and IL-1β from the epidermal cells or the Langerhans cells themselves.

This method of adjuvancy for transcutaneous immunization is envisioned to work for any compound that activates the Langerhans cell. Activation could occur in such manner as to downregulate the E-cadherin and upregulate ICAM-1. Langerhans cells would then carry antigens made of mixtures of such Langerhans cell-activating compounds and antigens (such as diphtheria toxoid or BSA) to the lymph nodes where the antigens are presented to T cells and evoke an immune response. Thus, the activating substance such as a bARE can be used as an adjuvant for an other wise transcutaneously non-immunogenic antigen such as diphtheria toxoid by activating the Langerhans cell to phagocytose the antigen such as diphtheria toxoid, migrate to the lymph node, mature into a dendritic cell, and present the antigen to T cells.

The T-cell helper response to antigens used in transcutaneous immunization may be influenced by the application of cytokines and/or chemokines. For example, interleukin-10 (IL-10) may skew the antibody response towards a Th2 IgG1/IgE response whereas anti-IL-10 may enhance the production of IgG2a (Bellinghausen et al., 1996).

Example 19

Sequestrin is a molecule expressed on the surface of malaria-infected erythrocytes which functions to anchor the malaria parasitized red blood cell to vascular endothelium. This is essential for parasite survival and contributes directly to the pathogenesis of *P. falciparum* malaria in children dying of cerebral malaria. In cerebral malaria, the brain capillaries become plugged with vast numbers of parasitized red blood cells due to the specific interaction of the sequestrin molecule with the host endothelial receptor CD36. Ockenhouse et al. (1991) identified both the host receptor CD36 and parasite molecule sequestrin which mediates this receptor-ligand interaction. Ockenhouse et al. (1991) have cloned and expressed as *E. coli*-produced recombinant protein, the domain of the sequestrin molecule which interacts with the CD36 receptor. A truncated 79 amino acid sequestrin product was used below.

Active immunization with recombinant sequestrin or DNA encoding the gene for sequestrin should elicit antibodies which block the adhesion of malaria parasitized erythrocytes to host endothelial CD36, and thereby prevent completion of parasite life cycle leading to parasite death due to its inability to bind to endothelium. The strategy is to provide a prophylactic or therapeutic treatment of immunization which elicits high-titer blocking antibodies. One such method is the deliver the vaccine transcutaneously. Measurements of both total antibody titers as well as blocking activity and opsonization form the basis for this approach with transcutaneous immunization. The recombinant sequestrin protein used in the present experiments is 79 amino acids long (~18 kDa) and comprises the CD36-binding domain of the molecule. We have also constructed a naked DNA construct comprised of this domain and have elicited antibodies using epidermal gene gun delivery.

BALB/c mice (n=3) were immunized transcutaneously as described above. The mice were immunized at 0 and 8 weeks using 120 µl of immunization solution prepared as follows: a plasmid encoded for *P. falciparum* sequestrin was mixed in saline to make an immunizing solution containing 80 µg of plasmid, 80 µg CT (List Biologicals) per 100 µl of saline. One hundred-twenty µl was applied to the untagged ear after gently cleansing the ear with an alcohol swab (TRIAD alcohol pad, 70% isopropyl alcohol). The immunizing solution was not removed by washing.

The antibodies to sequestrin were determined using "ELISA IgG(H+L)" as described above on sera collected from the tail vein at weeks 3, 4, 7 and 9 after the primary immunization. The results are shown in Table 15.

The pooled prebleed was 4 ELISA units. Sequestrin DNA with CT induced a detectable antibody response to the expressed protein after the second boosting immunization. For immunization to occur, the protein is envisioned to require expression from the plasmid, and processing by and presenting to the immune system. Thus, CT acted as an adjuvant for the immune response to sequestrin protein expressed by the plasmid encoding for sequestrin.

DNA vaccines have been shown to elicit neutralizing antibodies and CTLs in non-human primates to diseases such as malaria (Plasmodium; Gramzinski, 1997) and acquired immunodeficiency syndrome (HIV, Shriver et al., 1997), and have demonstrated protection to varying degrees in several models (McClements et al., 1997). Another useful model system is the humoral and CTL responses evoked by a DNA plasmid vaccine vector containing the human CMV immediate early promoter and encoding influenza virus nucleoprotein (NP; Pertmer et al., 1996). DNA immunization through the skin may elicit responses similar to that of a gene gun which targets the skin immune system (Condon et al., 1996; Prayaga et al., 1997).

TABLE 15

Anti-Sequestrin (Seq) Serum Antibody in Animals Immunized With Seq DNA and Cholera Toxin (CT)

| Animal # | Imm. Group | IgG (H + L) ELISA Units | | | |
|---|---|---|---|---|---|
| | | week 3 | week 4 | week 7 | week 9 |
| 8966 | Seq DNA/CT | 58 | 80 | 33 | — |
| 8967 | Seq DNA/CT | 76 | 81 | 41 | 146 |

TABLE 15-continued

Anti-Sequestrin (Seq) Serum Antibody in Animals Immunized With Seq DNA and Cholera Toxin (CT)

| Animal # | Imm. Group | IgG (H + L) ELISA Units | | | |
|---|---|---|---|---|---|
| | | week 3 | week 4 | week 7 | week 9 |
| 8968 | Seq DNA/CT | 54 | 33 | 26 | — |
| | Geo Mean | 62 | 60 | 33 | |

Example 20

BALB/c mice were immunized transcutaneously as described above using sequestrin in groups of five mice. Mice were immunized at 0, 2 and 8 weeks using 100 μl of immunization solution prepared as follows: mice were immunized with 59 μg CT and 192 μg sequestrin in 410 μl for the group receiving sequestrin and CT, 192 μg in 410 μl for sequestrin alone, and 120 μg CTB and 250 μg sequestrin in 520 μl for the group receiving sequestrin and CTB at 0 weeks. Two weeks later, the mice were boosted with 345 μl of saline containing either 163 μg sequestrin for the sequestrin alone group, 345 μl of saline containing 163 μg sequestrin with 60 μg CT for the CT plus sequestrin group, 345 μl of saline containing 163 μg sequestrin and 120 μg CTB for the sequestrin plus CTB group. In the second boost the mice were given 120 μg sequestrin for the sequestrin alone group, 120 μg sequestrin and 120 μg CT for the CT plus sequestrin group and 120 μg sequestrin and 120 μg CTB for the sequestrin plus CTB group.

Antibody levels were determined using "ELISA IgG(H+L)" as described above on serum collected 3, 5, 7, 9, 10, 11 and 15 weeks after the first immunization. The results are shown in Table 16. Sequestrin alone induced a small but detectable antibody response. But the addition of CT stimulated a far stronger immune response to sequestrin, and CTB induced an immune response that was superior to sequestrin alone. CT and CTB acted as adjuvants for the immune response to sequestrin, a recombinant protein. The pooled prebleed had a value of 5 ELISA units.

TABLE 16

Seq, Seq + Cholera Toxin (CT), or Seq + Cholera Toxin B (CTB)

| Animal# | Immunization Group | Detecting Antigen | IgG (H + L) ELISA Units | | | | | | |
|---|---|---|---|---|---|---|---|---|---|
| | | | prebleed | week 3 | week 5 | week 7 | week 8 | week 9 | week 11 | week 15 |
| 2861 | Seq | Seq | | 7 | 7 | 20 | 32 | 709 | 431 | 408 |
| 2862 | Seq | Seq | | 8 | 5 | 14 | 136 | 33 | 4 | 6 |
| 2863 | Seq | Seq | | 28 | 63 | 38 | 393 | 467 | 348 | 459 |
| 2864 | Seq | Seq | | 5 | 9 | 26 | 102 | 32 | 13 | 11 |
| 2865 | Seq | Seq | | 9 | 19 | 76 | 111 | 100 | 53 | 98 |
| | | Geo Mean | | 9 | 13 | 29 | 114 | 129 | 54 | 65 |
| 2866 | Seq/CT | Seq | | 923 | 1145 | 125 | 639 | 43679 | 28963 | 42981 |
| 2867 | Seq/CT | Seq | | 73 | 84 | 154 | ND | 9428 | 20653 | 27403 |
| 2868 | Seq/CT | Seq | | 805 | 370 | 1447 | 1105 | ND | 13169 | 7677 |
| 2869 | Seq/CT | Seq | | 175 | 760 | 1317 | 768 | 113792 | 118989 | 270040 |
| 2870 | Seq/CT | Seq | | 153 | 158 | 535 | 241 | 3245 | ND | 4277 |
| | | Geo Mean | | 271 | 336 | 456 | 601 | 19747 | 31115 | 25279 |
| 2871 | Seq/CTB | Seq | | 8 | 3 | 87 | 40 | 22 | 29 | 192 |
| 2872 | Seq/CTB | Seq | | 4 | 6 | 24 | 22 | 35 | 24 | 34 |
| 2873 | Seq/CTB | Seq | | 107 | 138 | 128 | 51 | 2074 | 2283 | 2296 |
| 2874 | Seq/CTB | Seq | | 6 | 7 | 22 | 18 | 41 | 40 | 457 |
| 2875 | Seq/CTB | Seq | | 515 | 504 | 1910 | 1744 | ND | 7148 | 5563 |
| | | Geo Mean | | 25 | 25 | 102 | 68 | 91 | 214 | 520 |

Example 21

BALB/c mice were immunized transcutaneously as described above in groups of five mice. The mice were immunized at 0 weeks using 100 µl of immunization solution prepared as follows: FLUSHIELD (Wyeth-Ayerst, purified subvirion, 1997-98 formula, lot #U0980-35-1) was lyophilized and was mixed in saline to make an immunizing solution containing 90 µg FLUSHIELD subvirion per 100 µl of saline for the group receiving influenza alone; influenza and CT were mixed in saline to make an immunizing solution containing 90 µg of FLUSHIELD antigens and 100 µg CT per 100 µl of saline for the group receiving influenza and CT.

The antibodies were determined using "ELISA IgG(H+L)" as described above on serum collected three weeks after the first immunization. The results are shown in Table 17. Influenza alone did not induce an antibody response. The addition of CT, however, stimulated a far stronger immune response which was superior to that observed influenza alone. Thus, CT acted as an adjuvant for the immune response to FLUSHIELD subvirion influenza vaccine, a mixture of virally derived antigens.

TABLE 17

Serum Antibody Against Influenza (Inf)
Types A and B in Animals Immunized
with Inf Alone or Inf + Cholera Toxin (CT)

| Animal # | Imm. Group | IgG (H + L) ELISA Units week 3 |
|---|---|---|
| 8601 | CT/Inf | 144 |
| 8602 | CT/Inf | 14 |
| 8603 | CT/Inf | 1325 |
| 8604 | CT/Inf | 36 |
| 8605 | CT/Inf | 29 |
|  | Geo Mean | 77 |
| 8606 | Inf | 17 |
| 8607 | Inf | 16 |
| 8608 | Inf | 20 |
| 8609 | Inf | 23 |
| 8610 | Inf | 23 |
|  | Geo Mean | 20 |

Example 22

LT is in the family of ADP-ribosylating exotoxins and is similar to CT in molecular weight, binds to ganglioside GM1, is 80% homologous with CT and has a similar A:B5 stoichiometry. Thus, LT was also used as an adjuvant for DT in transcutaneous immunization. BALB/c mice (n=5) were immunized as described above at 0, 8 and 18 weeks with a saline solution containing 100 µg LT (Sigma, catalog #E-8015, lot 17hH12000) and 100 µg CT (List Biologicals, catalog #101b) in 100 µl of saline. LT induced a modest response to DT as shown in Table 18.

ETA (List Biologicals, lot #ETA 25A) is in the family of ADP-ribosylating exotoxins, but is a single polypeptide that binds to a different receptor. One hundred µg of ETA was delivered in 100 µl of a saline solution containing 100 µg CT to BALB/c mice on the back as previously described at 0, 8 and 18 weeks. ETA boosted the response to DT at 20 weeks. Thus, other ADP-ribosylating exotoxins were able to act as adjuvants for coadministered proteins (Table 18).

TABLE 18

Kinetics of Diphtheria Toxoid (DT) Antibody Titers in Animals
Immunized With *Pseudomonas aeruginosa* Exotoxin A (ETA)
and DT or *E. coli* Heat Labile Enterotoxin (LT) and DT

| Animal # | Immunization Group | Detecting Antigen | IgG (H + L) ELISA Units prebleed | IgG (H + L) ELISA Units week 20 |
|---|---|---|---|---|
| 5146 | ETA/DT | DT |  | 31718 |
| 5147 | ETA/DT | DT |  | 48815 |
| 5148 | ETA/DT | DT |  | 135 |
| 5149 | ETA/DT | DT |  | 34 |
| 5150 | ETA/DT | DT |  | 258 |
|  |  | Geo Mean |  | 1129 |
| 5136 | LT/DT | DT |  | 519 |
| 5137 | LT/DT | DT |  | 539 |
| 5138 | LT/DT | DT |  | 38 |
| 5139 | LT/DT | DT |  | 531 |
| 5140 | LT/DT | DT |  | 901 |
|  |  | Geo Mean |  | 348 |
| pool |  |  | 3 |  |

Example 23

BALB/c mice were immunized transcutaneously as described above in groups of five mice. Mice were immunized at 0 weeks, 8 weeks and 18 weeks with 100 µl saline containing 100 µg cholera toxin (List Biologicals, catalog #101B, lot #10149CB), 50 µg tetanus toxoid (List Biologicals, catalog #191B, lots #1913a and 1915b) and 83 µg diphtheria toxoid (List Biologicals, catalog #151, lot #15151).

The antibodies against CT, DT, and TT were quantitated using "ELISA IgG (H+L)" as described above. Anti-CT, DT, or TT antibodies were detected at 23 weeks following the primary immunization. Anti-diphtheria toxoid and cholera toxin antibodies were elevated in all immunized mice. The highest responder had anti-tetanus toxoid antibody ELISA units of 342, approximately 80 times the level of antibody detected in sera of non-immunized animals. Thus, a combination of unrelated antigens (CT/TT/DT) can be used to immunize against the individual antigens. This demonstrates that cholera toxin can be used as an adjuvant for multivalent vaccines.

TABLE 19

Serum Antibody in Animals Immunized Simultaneously With
Cholera Toxin (CT), Tetanus Toxoid (TT), and Diphtheria Toxoid (DT)

| Animal # | Imm. Group | Detecting Antigen | IgG (H + L) ELISA Units prebleed | IgG (H + L) ELISA Units 23 weeks |
|---|---|---|---|---|
| 5176 | CT/TT/DT | CT |  | 7636 |
| 5177 | CT/TT/DT | CT |  | 73105 |
| 5179 | CT/TT/DT | CT |  | 126259 |
| 5216 | CT/TT/DT | CT |  | 562251 |
| 5219 | CT/TT/DT | CT |  | 66266 |
| pool |  |  | ≤3 |  |
|  |  | Geo Mean |  | 76535 |
| 5176 | CT/TT/DT | DT |  | 64707 |
| 5177 | CT/TT/DT | DT |  | 17941 |
| 5179 | CT/TT/DT | DT |  | 114503 |
| 5216 | CT/TT/DT | DT |  | 290964 |
| 5219 | CT/TT/DT | DT |  | 125412 |
| pool |  |  | ≤4 |  |
|  |  | Geo Mean |  | 86528 |
| 5176 | CC/TT/DT | TT |  | 21 |
| 5177 | CC/TT/DT | TT |  | 30 |

TABLE 19-continued

Serum Antibody in Animals Immunized Simultaneously With
Cholera Toxin (CT), Tetanus Toxoid (TT), and Diphtheria Toxoid (DT)

| Animal # | Imm. Group | Detecting Antigen | IgG (H + L) ELISA Units | |
|---|---|---|---|---|
| | | | prebleed | 23 weeks |
| 5179 | CT/TT/DT | TT | | 342 |
| 5216 | CT/TT/DT | TT | | 36 |
| 5219 | CT/TT/DT | TT | | 30 |
| pool | | | ≤2 | |
| | Geo Mean | | | 47 |

Example 24

Transcutaneous immunization using CT induces potent immune responses. The immune response to an intramuscular (IM) injection and oral immunization was compared to transcutaneous immunization using CT as adjuvant and antigen. Twenty-five μg of CT (List Biologicals, catalog #101b) dissolved in saline was administered orally in 25 μl to BALB/c mice (n=5) using a 200 μl pipette tip. The mice readily swallowed the immunization solution. Twenty-five μl of 1 mg/ml CT in saline was administered on the ear as described to the group labeled transcutaneous. Twenty-five μg of CT in saline was injected IM into the anterior thigh in the group labeled intramuscular.

The mice injected IM with CT developed marked swelling and tenderness at the injection site and developed high levels of anti-CT antibodies. Mice immunized transcutaneously had no redness or swelling at the site of immunization and developed high levels of ant-CT antibodies. Mice immunized orally developed far lower levels of antibodies compared to the mice immunized transcutaneously. This indicates that oral immunization through grooming in the transcutaneously immunized mice does not account for the high levels of antibodies induced by transcutaneous immunization. Overall, the transcutaneous route of immunization is superior to either oral or IM immunization as high levels of antibodies are achieved without adverse reactions to the immunization.

TABLE 20

Kinetics of Cholera Toxin Antibody Titers in Animals Immunized
by the Transcutaneous, Oral, or Intramuscular route

| Animal # | Immunization Route | IgG (H + L) ELISA Units | |
|---|---|---|---|
| | | prebleed | week 6 |
| 8962 | transcutaneous | | 23489 |
| 8963 | transcutaneous | | 30132 |
| 8964 | transcutaneous | | 6918 |
| 8965 | transcutaneous | | 20070 |
| 8825 | transcutaneous | | 492045 |
| pool | | 16 | |
| | Geo Mean | | 34426 |
| 8951 | oral | | 743 |
| 8952 | oral | | 4549 |
| 8953 | oral | | 11329 |
| 8954 | oral | | 1672 |
| pool | | 14 | |
| | Geo Mean | | 2829 |
| 8955 | intramuscular | | 35261 |
| 8958 | intramuscular | | 607061 |
| 8959 | intramuscular | | 452966 |
| 8850 | intramuscular | | 468838 |
| 8777 | intramuscular | | 171648 |
| pool | | 12 | |
| | Geo Mean | | 239029 |

Example 25

BALB/c mice were immunized transcutaneously as described above in groups of five mice. The mice were immunized at 0, 8 and 20 weeks using 100 μl of immunization solution prepared as follows: Hib-PS (Connaught, lot #6J81401, 86 μg/ml) was lyophilized in order to concentrate the antigen. The lyophilized product was mixed in saline to make an immunizing solution containing 50 μg Hib-PS per 100 μl of saline for the group receiving Hib-PS alone; Hib-PS and CT were mixed in saline to make an immunizing solution containing 50 μg Hib-PS and 100 μg CT per 100 μl of saline for the group receiving Hib-PS and CT.

The antibodies were determined using "ELISA IgG(H+L)" as described above on serum collected three weeks after the second immunization. The results are shown in Table 21 (pooled prebleed was 1 ELISA unit). Hib-PS alone induced a small but detectable antibody response. The addition of CT, however, stimulated a far stronger immune response to Hib-PS. CT acted as an adjuvant for the immune response to Hib-PS. This indicates that a polysaccharide conjugate antigen can be used as a transcutaneous antigen according to the present invention.

TABLE 21

Antibody to H. influenzae b polysaccharide conjugate (Hib-PS)

| Animal # | Imm. Group | IgG (H + L) ELISA Units |
|---|---|---|
| 5211 | Hib-PS | 57 |
| 5212 | Hib-PS | 29 |
| 5213 | Hib-PS | 28 |
| 5214 | Hib-PS | 63 |
| 5215 | Hib-PS | 31 |
| | Geo Mean | 39 |
| 5201 | CT/Hib-PS | 1962 |
| 5202 | CT/Hib-PS | 3065 |
| 5203 | CT/Hib-PS | 250 |
| 5204 | CT/Hib-PS | 12 |
| 5205 | CT/Hib-PS | 610 |
| | Geo Mean | 406 |

Example 26

Emulsions, creams and gels may provide practical advantages for convenient spreading of the immunizing compound over the skin surface, over hair or body creases. Additionally, such preparations may provide advantages such as occlusion or hydration which may enhance the efficiency of the immunization.

Heat labile entertoxin (LT) from E. coli (Sigma, catalog #E-8015, lot 17hH1200) was used to compare the efficiency of transcutaneous immunization using a simple saline solution and a commonly available petroleum base ointment, AQUAPHOR, which can be used alone or in compounding virtually any ointment using aqueous solutions or in combination with other oil based substances and all common topical medications. Mice were treated with a range of doses to evaluate the relative antibody response for the decreasing doses in the comparative vehicles.

BALB/c mice were immunized as described above except that the immunizing solution was applied for 3 hours on the back. Saline solutions of LT were prepared to deliver a 50 μl dose of solution and either 100 ng, 50 μg, 25 μg or 10 μg of antigen in the solution, using a 2 mg/ml, 1 mg/ml, 0.5 mg/ml or 0.2 mg/ml solution, respectively. After three hours, the back was gently wiped using wetted gauze to remove the immunizing solution.

The water in oil preparation was performed as follows: equal volumes of AQUAPHOR and antigen in saline solution were mixed in 1 ml glass tuberculin syringes with luer locks using a 15 gauge emulsifying needle connecting the two syringes and mixing until the mixture was homogenous. Four mg/ml, 2 mg/ml, 1 mg/ml, or 0.5 mg/ml solution of LT in saline was used, respectively, to mix with an equal volume of AQUAPHOR. Fifty μl of this mixture was applied to the shaved back for three hours and then gently removed by wiping with gauze. Doses of antigen for the water in oil LT containing emulsions were weighed in order to deliver 50 μl. The weight per volume ratio was calculated by adding the specific gravity of saline (1.00 g/ml) and AQUAPHOR, 0.867 gm/ml, and dividing the sum by two for a final specific gravity of 0.9335 gm/ml. Approximately 47 mg of water in oil emulsion containing LT was delivered to the mouse for immunization.

A dose-response relationship was evident for both saline and water in oil emulsion delivered LT (Table 22). One hundred µg induced the highest level of antibodies and 10 µg induced a lower but potent immune response. Water in oil emulsified LT induced a similar response to LT in saline and appears to offer a convenient delivery mechanism for transcutaneous immunization. Similarly, gels, creams or more complex formulations such as oil-in water-in-oil could be used to deliver antigen for transcutaneous immunization. Such compositions could be used in conjunction with occlusive dressings, patches, or reservoirs of other types of medical devices and may allow long-term application or short term application of the immunizing antigen and adjuvant.

Example 27

Mice were immunized transcutaneously as described above in groups of five mice. Mice were immunized at 0, 8 and 18 weeks with 100 µl saline containing 50 µg tetanus toxoid (TT; List Biologicals, catalog #191B, lots #1913a and #1915b) and 83 µg diphtheria toxoid (DT; List Biologicals, catalog #151, lot #15151) alone or in combination with 100 µg cholera toxin (CT; List Biologicals, catalog #1018, lot #10149CB).

Anti-diphtheria toxoid antibodies were quantitated using "ELISA IgG (H+L)" as described above. Elevated levels of anti-toxoid antibodies were detected in animals given immunized with either TT/DT or CT/TT/DT. The antibody titers were far superior, however, in animals in which CT was included as an adjuvant. This anti-toxoid titer was obviously increased in both groups after each subsequent immunization (8 and 18 weeks). Thus, while DT can induce a small but significant response against itself, the magnitude of the response can be increased by inclusion of cholera toxin as an adjuvant and boosting with the adjuvant cholera toxin and antigen (diphtheria toxoid). Classic boosting responses are dependent on T-cell memory and the boosting of the anti-DT antibodies in this experiment indicate that T-cells are engaged by transcutaneous immunization.

TABLE 22

Serum Antibody Against *E. coli* Heat-Labile Enterotoxin (LT) in Animals Immunized with Varying Doses of LT in a Saline or AQUAPHOR Emulsion

| Imm Group | emulsion | mouse# | IgG (H + L) ELISA Units prebleed | IgG (H + L) ELISA Units week 3 | emulsion | mouse# | IgG (H + L) ELISA Units prebleed | IgG (H + L) ELISA Units week 3 |
|---|---|---|---|---|---|---|---|---|
| LT 100 µg | saline | 8741 | | 18434 | aquaphor | 8717 | | 6487 |
| LT 100 µg | saline | 8742 | | 16320 | aquaphor | 8719 | | 4698 |
| LT 100 µg | saline | 8743 | | 19580 | aquaphor | 8774 | | 18843 |
| LT 100 µg | saline | 8744 | | 19313 | aquaphor | 8775 | | 18217 |
| LT 100 µg | saline | 8745 | | 22875 | aquaphor | 8861 | | 16230 |
| | | pool | 32 | | | pool | 54 | |
| Geo Mean | | | | 19190 | | | | 11117 |
| LT 50 µg | saline | 8736 | | 19129 | aquaphor | 8721 | | 4160 |
| LT 50 µg | saline | 8737 | | 3975 | aquaphor | 8722 | | 12256 |
| LT 50 µg | saline | 8738 | | 6502 | aquaphor | 8725 | | 12262 |
| LT 50 µg | saline | 8739 | | 6224 | aquaphor | 8771 | | 12982 |
| LT 50 µg | saline | 8740 | | 18449 | aquaphor | 8772 | | 15246 |
| | | pool | 54 | | | pool | 57 | |
| Geo Mean | | | | 8929 | | | | 10435 |
| | saline | 8768 | | 3274 | aquaphor | 8727 | | 3585 |
| LT 25 µg | saline | 8731 | | 3622 | aquaphor | 8728 | | 3 |
| LT 25 µg | saline | 8732 | | 557 | aquaphor | 8729 | | 4206 |
| LT 25 µg | saline | 8733 | | 626 | aquaphor | 8862 | | 7353 |
| LT 25 µg | saline | 8734 | | 1725 | aquaphor | 8769 | | 5148 |
| LT 25 µg | | pool | 56 | | | pool | 53 | |
| Geo Mean | | | | 1481 | | | | 1114 |
| | saline | 8848 | | 621 | aquaphor | 8748 | | 1968 |
| LT 10 µg | saline | 8849 | | 475 | aquaphor | 8749 | | 1935 |
| LT 10 µg | saline | 8757 | | 858 | aquaphor | 8750 | | 646 |
| LT 10 µg | saline | 8759 | | 552 | aquaphor | 8747 | | 1569 |
| LT 10 µg | saline | 8760 | | 489 | aquaphor | 8764 | | 1 |
| LT 10 µg | | pool | 43 | | | pool | 39 | |
| Geo Mean | | | | 585 | | | | 329 |

TABLE 23

Kinetics of Diphtheria Toxoid (DT) Antibody Titers in Animals Immunized
With Tetanus Toxoid (TT) and DT or Cholera Toxin (CT), TT, and DT

| Animal # | Immunization Group | Detecting Antigen | prebleed | wk 2 | week 4 | wk 6 | week 8 | wk 10 | week 14 | week 17 | week 18 | week 20 | week 23 |
|---|---|---|---|---|---|---|---|---|---|---|---|---|---|
| 5196 | TT/DT | DT | | 7 | 12 | 18 | 23 | 49 | 56 | 33 | 18 | 219 | 166 |
| 5197 | TT/DT | DT | | 5 | 11 | 11 | 10 | 15 | 17 | 16 | 17 | 125 | 75 |
| 5198 | TT/DT | DT | | 13 | 20 | 16 | — | 28 | 25 | 27 | 7 | 48 | 172 |
| 5199 | TT/DT | DT | | 13 | 8 | 10 | 10 | 11 | 22 | 12 | 217 | 178 | 263 |
| 5200 | TT/DT | DT | | 4 | 10 | 4 | 7 | 120 | 149 | 127 | — | 17309 | 14537 |
| | | Geo Mean | | 7 | 12 | 10 | 11 | 31 | 38 | 29 | 26 | 332 | 382 |
| 5176 | CT/TT/DT | DT | | 8 | 26 | 21 | 14 | 3416 | 5892 | 1930 | 1826 | 63087 | 64704 |
| 5177 | CT/TT/DT | DT | | 8 | 6 | 7 | 8 | 424 | 189 | 149 | 175 | 16416 | 17941 |
| 5179 | CT/TT/DT | DT | | 8 | 3 | 4 | 8 | 4349 | 1984 | 2236 | 1921 | 124239 | 114503 |
| 5216 | CT/TT/DT | DT | | 12 | 5 | 9 | 11 | 3238 | 2896 | 2596 | 1514 | 278281 | 290964 |
| 5219 | CT/TT/DT | DT | | 8 | 15 | 13 | 12 | 5626 | 4355 | 2036 | 1941 | 343161 | 125412 |
| | | Geo Mean | | 9 | 8 | 9 | 10 | 2582 | 1945 | 1277 | 1125 | 104205 | 86528 |
| pool | | | 4 | | | | | | | | | | |

Example 28

C57BL/6 mice were immunized transcutaneously with cholera toxin (CT; azide-free, Calbiochem, La Jolla, Calif.) as described above on their shaved backs. Mice were challenged using a lethal challenge model 6 weeks after immunization (Mallet et al., Immunoprophylactic efficacy of nontoxic mutants of *Vibrio cholera* toxin (CTK63) and *Escherichia coli* heat-labile toxin (LTK63) in a mouse cholera toxin intranasal challenge model, in preparation). For the challenge, mice were given 20 µg CT (Calbiochem, azide free) dissolved in saline intranasally via a plastic pipette tip while anesthetized with 20 µl of ketamine-rompin. In the first challenge, 12/15 immunized mice survived the challenge after 14 days and 1/9 non-immunized control mice survived. Five control mice were lost prior to challenge due to anesthesia. Mice in the first challenge had anti-CT serum antibodies of 15,000 ELISA units (geometric mean), and five immunized mice sacrificed at the time of challenge had lung wash IgG detected in 5/5 mice. Lung washes were collected as described above.

The immunization and challenge was repeated with naïve C57BL/6 mice and 7/16 immunized mice survived the challenge, while only 2/17 non-immunized mice survived the challenge. Immunized mice in the second challenge had anti-CT IgG antibodies of 41,947 ELISA units (geometric mean). Lung washes from five mice sacrificed at the time of challenge demonstrated both anti-CT IgG and IgA (Table 24). Stool samples from 8/9 mice demonstrated both anti-CT IgG and IgA (Table 25). Stool samples were collected fresh from animals spontaneously defecating at the time of challenge. The stools were frozen at −20° C. At the time of ELISA, the stools were thawed, homogenized in 100 µl of PBS, centrifuged and ELISA run on the supernatant. The combined survival rate among immunized mice was 19/31 or 61%, whereas the combined survival rate among non-immunized mice was 3/26 or 12%.

TABLE 24

Lung Wash Anti-Cholera Toxin (CT) IgG and IgA Titers

| Sample Dilution | Animal Identification Number | | | | |
|---|---|---|---|---|---|
| | 8969 | 8970 | 8971 | 8972 | 8995 |
| IgG (H + L) anti-CT (Optical Density) | | | | | |
| 1:10 | 3.613 | 3.368 | 3.477 | 3.443 | 3.350 |
| 1:20 | 3.302 | 3.132 | 3.190 | 3.164 | 3.166 |
| 1:40 | 3.090 | 2.772 | 2.825 | 2.899 | 2.692 |
| 1:80 | 2.786 | 2.287 | 2.303 | 2.264 | 2.086 |
| 1:160 | 2.041 | 1.570 | 1.613 | 1.624 | 1.441 |
| 1:320 | 1.325 | 0.971 | 1.037 | 1.041 | 0.965 |
| 1:640 | 0.703 | 0.638 | 0.601 | 0.644 | 0.583 |
| 1:1280 | 0.434 | 0.382 | 0.350 | 0.365 | 0.364 |
| IgA anti-CT (Optical Density) | | | | | |
| 1:2 | 1.235 | 2.071 | 2.005 | 2.115 | 1.984 |
| 1:4 | 1.994 | 1.791 | 1.836 | 1.85 | 1.801 |
| 1:8 | 1.919 | 1.681 | 2.349 | 1.796 | 1.742 |
| 1:16 | 1.8 | 1.457 | 1.577 | 1.614 | 1.536 |
| 1:32 | 1.503 | 1.217 | 1.36 | 1.523 | 1.23 |
| 1:64 | 1.189 | 0.863 | 1.044 | 1.101 | 0.88 |
| 1:128 | 0.814 | 0.57 | 0.726 | 0.74 | 0.595 |
| 1:356 | 0.48 | 0.334 | 0.436 | 0.501 | 0.365 |

TABLE 25

Stool Anti-Cholera Toxin IgG and IgA Antibody Titers

| Sample Dilution | Mouse Identification Number (Immunization Group) | | | | | | | | | | | |
|---|---|---|---|---|---|---|---|---|---|---|---|---|
| | 8985 (CT) | 8997 (CT) | 8987 (CT) | 8990 (CT) | 8977 (CT) | 8976 (CT) | 8975 (CT) | 8988 (CT) | 8994 (none) | 8979 (none) | 9000 (none) | 8983 (none) |
| IgG (H + L) anti-CT (optical density) | | | | | | | | | | | | |
| 1:10 | 1.01 | 1.91 | 2.33 | 0.03 | 0.74 | 1.98 | 1.20 | 1.45 | 0.09 | 0.05 | 0.02 | 0.18 |
| 1:20 | 0.42 | 0.94 | 1.26 | — | 0.31 | 1.19 | 0.50 | 0.91 | 0.04 | — | — | 0.08 |

TABLE 25-continued

Stool Anti-Cholera Toxin IgG and IgA Antibody Titers

| | Mouse Identification Number (Immunization Group) | | | | | | | | | | | |
|---|---|---|---|---|---|---|---|---|---|---|---|---|
| Sample Dilution | 8985 (CT) | 8997 (CT) | 8987 (CT) | 8990 (CT) | 8977 (CT) | 8976 (CT) | 8975 (CT) | 8988 (CT) | 8994 (none) | 8979 (none) | 9000 (none) | 8983 (none) |
| 1:40 | 0.20 | 0.46 | 0.68 | — | 0.12 | 0.58 | 0.24 | 0.49 | — | — | — | 0.02 |
| 1:80 | 0.10 | 0.21 | 0.34 | — | 0.05 | 0.31 | 0.09 | 0.25 | — | — | — | — |
| 1:160 | 0.03 | 0.09 | 0.18 | — | 0.02 | 0.14 | 0.05 | 0.12 | — | — | — | — |
| IgA Anti-CT (optical density) | | | | | | | | | | | | |
| 1:4 | 0.32 | 1.14 | 0.43 | 0.00 | 0.19 | 1.00 | 0.58 | 1.21 | 0.02 | — | 0.07 | — |
| 1:8 | 0.16 | 0.67 | 0.24 | — | 0.08 | 0.56 | 0.36 | 0.77 | — | — | — | — |
| 1:16 | 0.08 | 0.33 | 0.11 | — | 0.03 | 0.27 | 0.17 | 0.40 | — | — | — | — |
| 1:32 | 0.06 | 0.16 | 0.05 | — | 0.03 | 0.12 | 0.08 | 0.20 | — | — | — | — |
| 1:64 | 0.01 | 0.07 | 0.03 | — | — | 0.05 | 0.03 | 0.10 | — | — | — | — |

Example 29

C57BL/6 female mice were obtained from Charles River Laboratories. The mice were immunized with 200 µg ovalbumin (OVA) (Sigma, lot #14H7035, stock concen-tration of 2 mg/ml in PBS) and 50 µg cholera toxin (List Biologicals, lot #101481B, stock concentration of 5 mg/ml). A Packard Cobra gamma counter was used (serial #102389) to measure the amount of $^{51}$Cr released.

C57BL/6 mice were anesthetized with 0.03 ml of ketamine-rompin and shaved on the dorsum with a clipper, without traumatizing the skin, and were rested for 24 hours. The mice were anesthetized then immunized at 0 and 28 days with 150 µl of immunizing solution placed on the shaved skin over a 2 cm$^2$ area for two hours. The mice were then wiped twice with wet gauze. The mice exhibited no adverse effects from anesthesia, immunization, or the washing procedure. This procedure was repeated weekly for three weeks.

Splenic lymphocytes were collected one week after boosting immunization. Cells were cultured in vitro in RPMI-1640 and 10% PBS (with penicillin, streptomycin, glutamine, nonessential amino acids, sodium pyruvate, and β-mercaptoethanol) for six days with the addition of 5% rat concanavalin A supernatant as a source of IL-2, with or without antigen. Target cells consist of syngeneic (H-2$^b$) EL4 cells alone and EL4 cells pulsed with the CTL peptide SINFEKKL (SEQ ID NO:1), allogeneic (H-2$^k$) L929 cells and EG7 cells. The target cells (1×10$^6$ cells per well) were labeled for one hour with 0.1 mCi per well $^{51}$Cr (Na$_2$CrO$_4$ source, Amersham) and were added to effector cells at ratios ranging from 3:1 to 100:1. The cell mixtures were incubated in 96-well round bottom tissue culture plates (Costar, catalog #3524) in 0.2 ml complete RPMI-1640, 10% FBS medium for five hours at 37° C. in a 5% CO$_2$ humidified chamber. At the end of the five-hour culture, supernatants were absorbed by cotton wicks and processed for the determination of $^{51}$Cr release. Specific lysis was deter-mined as: % Specific Lysis=100×[(experimental release−spontaneous release)/(maximal release−spontaneous release)].

As shown in Table 26 (part 1), CTLs were detected against the EL4 peptide pulsed cells at an E:T ratio of 100:1 for the group immunized with CT+OVA. CTL assays are not considered positive if the percent specific lysis is not above 10%, or clearly above the media-stimulated effectors background percentage lysis. Similarly, as shown in Table 26 (part 2), CTLs were detected against the EG7 (OVA transfected cells) at an E:T ratio of 100:1 for the group immunized with CT+OVA. Thus, CT adjuvanted for the production of CTLs via the transcutaneous route.

TABLE 26

OVA-Specific CTL Induced Transcutaneously

| | Imm. Group | | Stimulated with | | | |
|---|---|---|---|---|---|---|
| E:T Ratio | CT + OVA Media | CT + OVA OVA | CT Media | CT OVA | OVA Media | OVA OVA |
| Part 1-Target Cells: EL4 + Peptide | | | | | | |
| 100:1 | 9.5 | 13.1 | 11.1 | 12.5 | 23.1 | 21.5 |
| 30:1 | 6.9 | 6.8 | 5.9 | 8.9 | 14.2 | 10.7 |
| 10:1 | 4.9 | 3.5 | 3.5 | 8.5 | 7.7 | 5.2 |
| Part 2-Target Cells: EG7 (OVA Transfected) | | | | | | |
| 100:1 | 10.6 | 17.6 | 14.5 | 16.8 | 23.8 | 26 |
| 30:1 | 4.9 | 9.5 | 8.2 | 10.1 | 13.6 | 10.7 |
| 10:1 | 6.4 | 4.4 | 4 | 5 | 7.3 | 4.2 |

Example 30

C57BL/6 mice (n=6) were immunized transcutaneously as described above. Mice were immunized at 0 and 4 weeks with 100 µl saline containing 100 µg cholera toxin (List Biologicals, catalog #101B, lot #10149CB) and 250 µg of ovalbumin protein (Sigma, albumin chicken egg, Grade V catalog #A5503, lot #14H7035).

Single-cell suspensions were prepared from spleens harvested from animals at eight weeks after the first immunization. Splenocytes were set up in culture at 8×10$^5$ cells per well in a 200 µl volume containing ovalbumin antigen or the irrelevant protein conalbumin at the concentrations indicated. Cultures were incubated for 72 hours at 37° C. in a CO$_2$ incubator and then 0.5 µCi/well of $^3$H thymidine was added to each well. Twelve hours later, proliferation was assessed by harvesting the plates and quantitating incorporated radiolabelled thymidine by liquid scintillation counting. Raw values of $^3$H incorporation are indicated in cpm and the fold increase (cpm experimental/cpm media) is indicated to the left of each sample. Fold increases greater than three were considered significant.

Significant proliferation was only detected when the splenocytes were stimulated with the protein, ovalbumin, to which the animals had been immunized with in vivo and not with the irrelevant protein conalbumin. Thus transcutaneous immunization with cholera toxin and ovalbumin protein induces antigen specific proliferation of splenocytes in vitro indicating that a cellular immune response is evoked.

TABLE 27

Antigen-Specific Proliferation of Spleen Cells from Animals Immunized With Cholera Toxin (CT) and Ovalbumin (OVA)

| Concentration of In Vitro Stimuli | Media | | OVA Protein | | Conalbumin |
|---|---|---|---|---|---|
| | $^3$H incorporation cpm | fold increase | $^3$H incorporation cpm | fold increase | |
| 10 µg/ml | 1427 | 13450 | 94 | 3353 | 2.3 |
| 1 µg/ml | 4161 | 2.9 | 2638 | 1.8 | |
| 0.1 µg/ml | 2198 | 1.5 | 2394 | 1.7 | |
| 0.01 µg/ml | 3419 | 2.4 | 2572 | 1.8 | |

Example 31

Immunoprotection using the transcutaneous immunization method can clearly be shown using a tetanus toxin challenge model (Chen et al., 1998). BALB/c mice were immunized transcutaneously as described previously using 100 µg tetanus fragment C (TetC, List Biologicals), 100 µg TetC and 100 µg CT (List Biologicals), or with sequestrin, a non-relevant malaria recombinant protein, or CT plus sequestrin, a non-relevant malaria recombinant protein. Five mice were immunized and then boosted three times.

Antibody responses to TetC were determined by ELISA as previously described and are shown below for the TetC and TetC+CT groups. One of the five animals in the TetC group responded strongly, and another had a response two times over background (Table 28). Three out of five animals in the TetC+CT group responded strongly, and two of five animals had responses two times over background (Table 29). The ELISA units for negative control and pre-bleed (1/100 dilution) are shown.

TABLE 28

TetC

| Dilution | Mouse# 5401 | Mouse# 5402 | Mouse# 5403 | Mouse# 5404 | Mouse# 5404 |
|---|---|---|---|---|---|
| 1/100 | 0.21 | 0.33 | 0.15 | 0.42 | 2.22 |
| 1/200 | 0.10 | 0.28 | 0.24 | 0.50 | 2.03 |
| 1/400 | 0.13 | 0.34 | 0.26 | 0.31 | 1.08 |
| 1/800 | 0.15 | 0.30 | 0.26 | 0.16 | 1.05 |
| 1/1600 | 0.15 | 0.26 | 0.26 | 0.19 | 0.73 |
| 1/3200 | 0.16 | 0.24 | 0.26 | 0.29 | 0.57 |
| 1/6400 | 0.14 | 0.20 | 0.25 | 0.26 | 0.43 |
| 1/12800 | 0.12 | 0.10 | 0.07 | 0.07 | 0.22 |
| pre 1/100 | 0.10 | 0.11 | 0.10 | 0.12 | 0.14 |
| Neg. Cont. | 0.09 | 0.07 | 0.09 | | |

TABLE 29

TetC + CT

| Dilution | Mouse# 5406 | Mouse# 5407 | Mouse# 5408 | Mouse# 5409 | Mouse# 5410 |
|---|---|---|---|---|---|
| 1/100 | 0.50 | 0.37 | 2.69 | 2.86 | 3.04 |
| 1/200 | 0.36 | 0.28 | 2.55 | 2.77 | 2.98 |
| 1/400 | 0.22 | 0.23 | 1.93 | 2.36 | 2.64 |
| 1/800 | 0.16 | 0.17 | 122 | 2.41 | 2.33 |
| 1/1600 | 0.12 | 0.13 | 1.97 | 2.21 | 2.28 |
| 1/3200 | 0.09 | 0.25 | 2.15 | 2.36 | 1.70 |
| 1/6400 | 0.09 | 0.21 | 1.80 | 2.24 | 1.16 |
| 1/12800 | 0.09 | 0.11 | 1.49 | 2.08 | 0.90 |
| Pre 1/100 | 0.08 | 0.09 | 0.08 | 0.08 | 0.10 |
| Neg. Cont. | 0.06 | 0.07 | 0.07 | | |

Tetanus challenge was performed using tetanus toxin (List Biologicals, Cat#190). One vial of 25 µg of tetanus toxin was reconstitute with 100 µl of sterile endotoxin-free water (Sigma cat#W-3500) to make 250 µg/ml tetanus. Ten µl of this solution (250 µg/ml tetanus) was mixed with 9,990 µl of diluent (sterile nutrient broth and borate buffer mixed 1:1, pH 7.4) to make 250 ng/ml of tetanus toxin. Mice received 200 µl of 50 ng/ml (i.e., 10 ng) of tetanus toxin subcutaneously on the scruff of the neck.

Immunoprotection was clearly shown in the group immunized with CT+TetC via the transcutaneous route (Table 30). Two mice immunized with Tet C alone survived and no mice from the control groups survived.

TABLE 30

Immunoprotection of Mice Immunized Transcutaneously with Tetanus Fragment C (TetC) Adjuvanted by Cholera Toxin

| Group # | n | Immunization | Survival |
|---|---|---|---|
| 1 | 5 | TetC | 2/5 |
| 2 | 5 | TetC + CT | 5/5 |
| 3 | 5 | CT + Seq | 0/5 |
| 4 | 5 | Seq | 0/5 |

Example 32

Kinetics of Anti-CT Serum IgG (H+L) Response Induced by Transcutaneous Immunization When administered by the oral or parenteral route, CT stimulates an immune response as measured by an increase in toxin specific antibodies. We have shown above that application of a saline solution containing CT to the bare skin of a shaved mouse (i.e., transcutaneous immunization) elicits a similar systemic immune response. We further demonstrate that application of CT to the skin in this manner induced a rise in detectable anti-CT antibodies from ≤10 ELISA units before immunization to 10,000 ELISA units after a single application. Such elevated CT titers were apparent within two weeks of antigen exposure and persisted for at least eight weeks at which time the animals were re-exposed to determine whether still higher antibody responses could be elicited.

FIG. 1, panels A-B, shows the CT-specific antibody responses in BALB/c mice immunized transcutaneously with cholera toxin (CT). Mice were immunized with 100 µg CT at 0, 8 and 18 weeks. Results shown are the geometric mean and SEM of CT-specific IgG (H+L) measured in serum collected from each of five individual animals and reported in ELISA units, the inverse dilution at which the absorbance is equal to 1.0. Essentially identical results were obtained in three independent experiments. Repeated immunizations at eight and 18 weeks following immunization induced approximately 30-fold (FIG. 1A) and 3-fold (FIG. 1B) incremental increases in the CT specific antibody titers, respectively.

Figure 2:
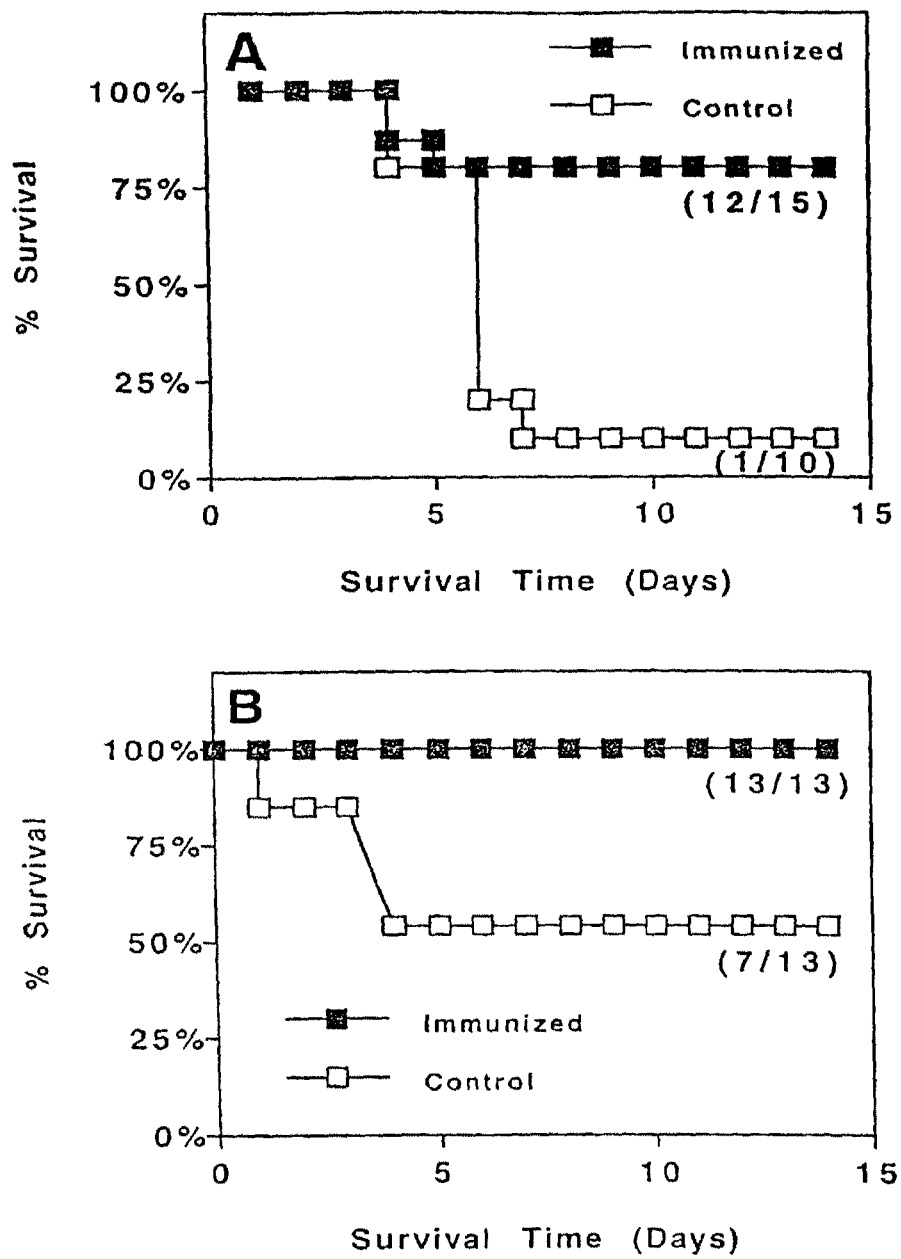
FIG. 2, panels A-B, shows mortality in a population of C57BL/6 mice that have been immunized with CT by the transcutaneous route and then intranasally challenged with native toxin three weeks after (A) one or (B) two rounds of immunization. In both trials, survival was significant at the $p<0.05$ level (Fisher Exact). The number of mice per group is indicated in parentheses (total survivors/number of mice in study).

Induction of Protective Host Immunity by Transcutaneous Vaccination with Native CT Intranasal challenge of C57BL/6J mice with CT induces fatal cytotoxic pulmonary lesions characterized by suppurative interstitial pneumonia with marked perivascular edema, fibrin deposition, and hemorrhage. Mutant toxins of CT and heat-labile enterotoxin from E. coli induced systemic and mucosal anti-toxin antibodies after two intranasal immunizations to show intranasal challenge with CT. We utilized this challenge model as a means to assess the physiologic significance of the anti-toxin response induced by transcutaneous immunization. In the present study, mice were immunized with native CT once or twice and challenged intranasally with lethal doses of CT. FIG. 2A shows the results of the first trial of mice immunized a single time. In this trial, only 11% (1/9) of control mice survived the challenge as compared to 80% (12/15) of the mice immunized with CT transcutaneously ($p=0.002$). FIG. 2B shows a subsequent experiment using older mice (20 weeks) in which were immunized twice, 100% of the immunized mice survived the challenge whereas 57% (7 of 13) of the control mice survived ($p=0.007$). It is unclear why so many of the control mice in the latter experiment failed to succumb to the challenge. One possible explanation relates to the greater weight of the older mice which may have received a lower mg/kg intranasal dose of the toxin.

Characterization of Transcutaneously Induced Mucosal IgG and IgA Responses

To characterize the nature of the immune response induced by transcutaneous immunization that protects against an intranasal toxin challenge, CT in saline was applied to the shaved skin of mice and sera, lung washes, and stool samples were collected and analyzed for IgG (H+L) and IgA four weeks later.

Figure 3:
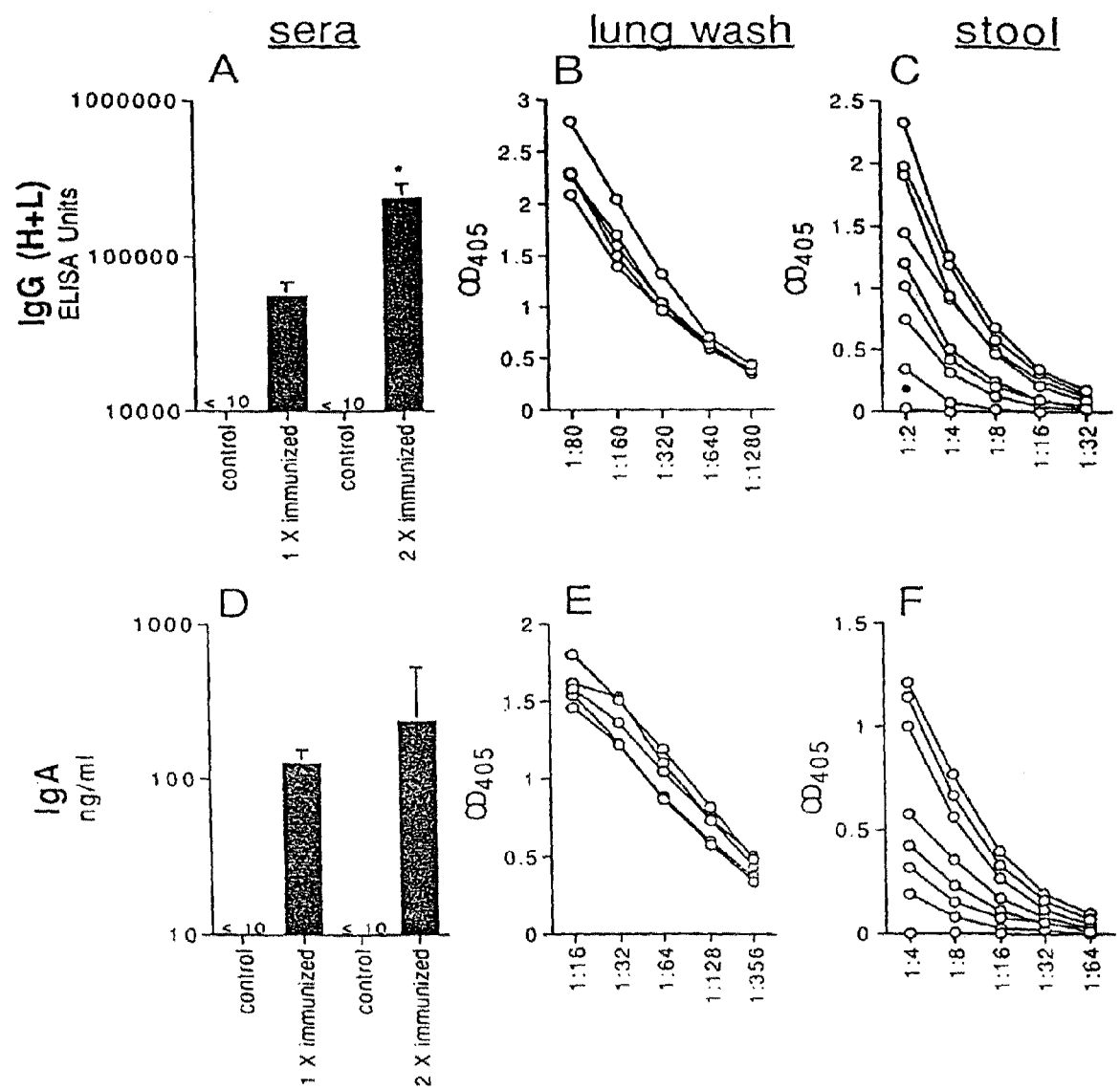
FIG. 3, panels A-F, shows serum (A and D) and mucosal (lung in B and E; stool in C and F) antibody responses to CT after transcutaneous immunization.
Figure 4:
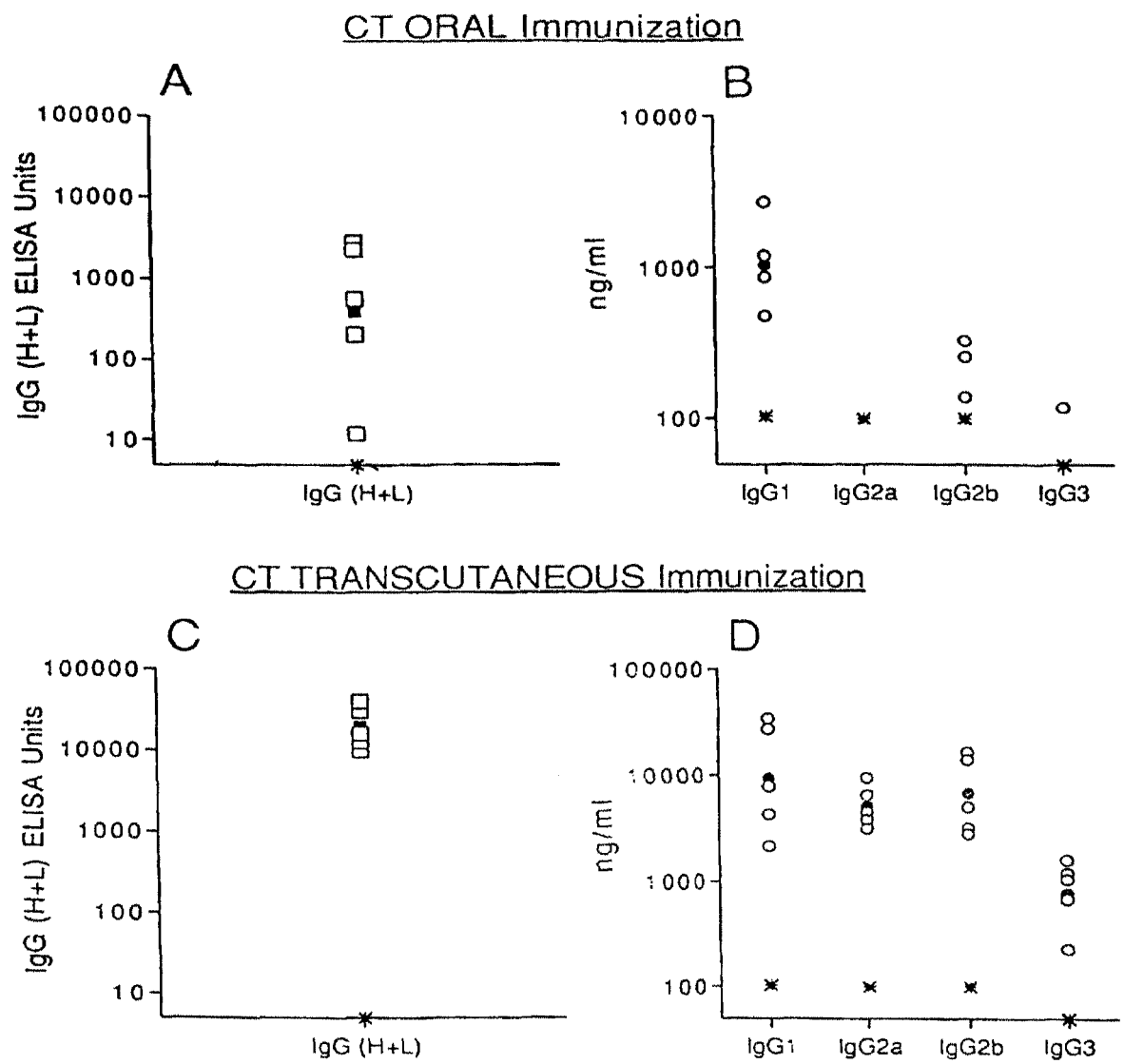
FIG. 4, panels A-D, shows serum antibody responses induced by oral (panels A and B) or transcutaneous (panels C and D) exposure to CT. Results shown are measurements from the five individual animals (hollow squares for panels A and C; hollow circles for panels B and D). Solid symbols indicate the geometric mean value for each cohort of animals. An asterisk (*) denotes the mean value detected in prebleed serum of the mice.

FIG. 3, panels A-F, shows serum (A and D) and mucosal (lung in B and E; stool in C and F) antibody responses to CT after transcutaneous immunization. Panels A and D: C57BL/6 mice (17-22 animals per group) were immunized transcutaneously at 0 and 3 weeks with 100 µg CT. Sera was collected at 3 and 6 weeks and the CT specific Ig (H+L) and IgA levels assessed by ELISA. Data shown are the geometric mean±SEM for measurements from five individual animals. An asterisk denotes a statistically significant ($p<0.05$) difference between the titers measured in the 1× and 2× immunization groups. (panels B and E): C57BL/6 mice were immunized transcutaneously at 0 weeks. Lung washes were performed on representative mice (n=5) after sacrifice on the day of challenge (3 weeks) by tracheal transection as described. Ig (H+L) and IgA levels were assessed by ELISA and the titers (optical density at 405 nm) from individual animals are shown. Neither IgG nor IgA were detected in lung washes from non-immunized animals. (panels C and F): C57BL/6 mice were immunized transcutaneously at 0 weeks. Single stool pellets were collected immediately after defecation on the day before toxin challenge (6 weeks). Antibodies were extracted from fecal homogenates as described. Ig (H+L) and IgA levels were assessed by ELISA and the titers (optical density at 405 nm) from eight (F) or nine (C) individual animals are shown. CT specific IgA was not detected in stool samples from non-immunized mice. A solid circle denotes the maximal level of anti-CT Ig antibody detected in 1:2 dilutions of sera from non-immunized mice (background).

As expected, the titer of detectable anti-CT IgG antibodies increased more than 3 logs following a single immunization (FIG. 3A). Sera from mice exposed twice to CT at 3 week intervals (0 and 3 weeks) exhibited significantly augmented IgG and IgA titers 3 weeks after the second transcutaneous application (FIGS. 3A and 3D). Importantly, CT specific IgG was also detected in 5 of 5 lung wash samples and 8 of 9 stool sample homogenates from the single exposure groups (FIG. 3B-C). Further analysis of the samples revealed a potent IgA response, albeit lower than the IgG titers, in all of the compartments analyzed (FIG. 3D-F) indicating that classical mucosal immunity had been elicited. In contrast, lung wash samples from animals assayed using as irrelevant protein, ricin B-subunit as coating antigen in the ELISA, failed to exhibit detectable anti-CT IgG or IgA levels, and stool samples from non-immunized mice had less than 0.2 IgG OD units at a 1:2 dilution and no detectable IgA. Neither IgM nor IgE anti-CT antibodies were detected in the sera of transcutaneously immunized mice.

Comparison of CT Antibody Responses in the Sera of Orally and Transcutaneously Immunized Mice Although we are extremely careful to remove the antigen from the skin after each application of immunizing solution, it was conceivable that animals vaccinated in this manner might, through normal grooming, ingest small amounts of the antigen and thus orally expose themselves to the toxin. To formally exclude this possibility as a trivial explanation of our results, we have directly compared the immune response induced by exposing animals to CT by the oral and transcutaneous routes.

Five BALB/c mice were immunized with 25 µg CT by oral gavage or 100 µg by transcutaneous application to the back. Serum was collected four weeks later and the levels of CT specific Ig (H+L), IgG1, IgG2a, IgG2b, and IgG3 assessed by ELISA as described above. Results shown are measurements from the five individual animals (hollow squares for panels A and C; hollow circles for panels B and D). Solid symbols indicate the geometric mean value for each cohort of animals. An asterisk (*) denotes the mean value detected in prebleed serum of the mice.

As shown in FIG. 4A-D, the magnitude of the anti-CT IgG response at 4 weeks after immunization was significantly higher in serum from mice in which CT was introduced by the transcutaneous (geometric mean=19,973 ELISA units) as compared to oral (geometric mean=395 ELISA units) route. Moreover, while transcutaneous immunization induced a full complement of IgG subclasses (IgG1, IgG2a, IgG2b, and IgG3) only IgG1 (4 of 5 animals) and to a lesser extent IgG2b (3 of 5 animals) were detected in the sera from the orally exposed mice. In a separate experiment, oral immunization with 10 µg CT in saline at 0 and 3 weeks induced a 6 week mean IgG antibody response of <1,000 ELISA units whereas transcutaneous immunization with 100 µg CT resulted in an anti-CT response of 39,828 ELISA units. Similar results were obtained using 25 µg CT on the unshaved ear which is less accessible that the back for grooming compared to 25 µg orally immunized (34,426 vs. 2829 ELISA units, respectively).

CT is exquisitely sensitive to degradation in the low pH of the stomach and is generally given orally with a buffer to induce a mucosal response. Thus, it is unlikely that ingestion of CT by grooming would cause the dramatic rise in antibody titers which we observe following transcutaneous immunization. In order to exclude this possibility, however, mice were anesthetized during the immunization period and extensively washed at the end of the exposure period. Numerous trials comparing oral and transcutaneous immunization methods argue against a role for oral immunization in inducing the high antibody titers seen with epicutaneous application of CT. In addition, the IgG subclass responses to each route of immunization differed. Oral immunization induced almost exclusively IgG1 and IgG2b antibodies consistent with the findings of Vajdy and Licke (1995), whereas transcutaneous immunization induced a broad IgG subclass response. Thus ingestion of CT following transcutaneous immunization does not appear to account for the potent immune responses associated with this method.

Complete protection against toxin-mediated enteric disease through immunization remains elusive in part due to the toxicity of the targeted toxins, although partial protection can be achieved. We have demonstrated that CT administered topically to the skin induces systemic antibody responses without adverse reactions. Here, transcutaneously immunized mice were challenged by a mucosal route with lethal amounts of toxin, and significant levels of protection were seen. Direct correlation of the extent of mucosal antibody responses and protection was not possible since representative mice were sacrificed to assess local (lung) mucosal immunity on the day of challenge. But lung washes from mice sacrificed on the day of challenge and stool samples from all mice on the day of challenge in both the single and two dose immunization exhibited elevated anti-CT IgG and IgA antibodies. Thus, mucosal antibodies induced by transcutaneous immunization were associated with protection against toxin challenge.

Protection against non-CT mediated diseases such as pertussis are known to be mediated in large part by anti-toxin antibodies. Anti-toxin immunity can be completely protective in animals and clearly contributes to immunity in resistant humans. For example, dogs parenterally immunized with CT or given anti-CT IgG antibodies paren-terally were protected against intragastric challenge with CT producing strains of *Vibrio cholera*. Moreover, anti-CT IgA reduces rabbit illeal loop secretory responses to CT.

The toxicity of CT given by the mucosal route has limited its use as a vaccine antigen and studies on the protective role of anti-CT antibodies have used the less toxic but less immunogenic derivatives of CT such as CTB and cholera toxoid. Introduction of CT to the host by transcutaneous immunization may prove to be a powerful technique that elicits potent immune responses in the absence of overt toxicity. Additional studies are warranted to assess the utility of transcutaneous immunization in human vaccines against infectious and toxin mediated diseases particularly cholera or traveler's diarrhea. Furthermore, transcutaneous immunization offers convenient application of multiple boosting immunizations and multivalent vaccine delivery.

Example 33

C57BL/6 mice 6 to 8 weeks of age were shaved and anaesthetized as described above. On the day of immunization, the backs of mice were wiped with isopropanol. After the alcohol had evaporated (approximately 5 minutes), their backs were hydrated for an additional 5 minutes with water. After gentle blotting of excess water, 50 μl of phosphate buffered saline (PBS) containing 100 μg CS6 alone or 100 μg CS6 and CT (10 μg or 100 μg) was applied to the skin. Two hours later any remaining antigen was removed by rinsing the skin of the animals with copious amounts of water. Immunization was repeated 4 and 8 weeks later. Twelve weeks after the primary immunization, the animals were bled and the anti-CS6 titers determined using "ELISA IgG (H+L)" as described above. The results are shown in Table 31.

Administration of the antigen (CS6) alone failed to induce a rise in antigen specific antibody levels when compared to the levels observed in prebleed samples. In contrast, epicutaneous application of CS6 to the skin with either 10 μg or 100 μg CT induced a potent anti-CS6 response in 10 out of 10 immunized animals which represented a 100 to 1000 fold increase over the prebleed titers. Remarkably, the anti-CS6 titers in the serum of transcutaneously immunized mice were comparable to that observed in animals immunized with the antigen in alum by the conventional intramuscular route. CS6 contained a high level of endotoxin: approximately 120,000 endotoxin units/1.3 mg by LAL. The titers to CS6 are among the highest antibody titers seen to date for immunization by transcutaneous delivery and suggests that LPS, an additional adjuvant, may augment the immune response induced by CT.

Stool pellets were collected the day before challenge after spontaneous defecation. Pellets were weighed and homogenized in 1 ml of PBS per 100 mg fecal material, centrifuged and the supernatant collected and stored at −20° C. We have shown that CT administered via the transcutaneous route induces protective anti-CT antibodies detectable at the mucosal surfaces. To determine whether CT also induces an antibody response against coadministered antigen detectable at the mucosal surfaces, mice were immunized transcutaneously with CT as an adjuvant for CS6 antigen and the mucosal (stool) anti-CT and anti-CS6 IgG titers were evaluated. Anti-CT and anti-CS6 IgG was detected in the stool samples from mice immunized with CT and CS6 (FIG. 5). CS6 is an candidate vaccine *E. coli* antigen for treating ETEC. The presence of CS6 antibodies in the stool would suggest that this is an important vaccine antigen using transcutaneous immunization because CS6 antibodies may protect against ETEC, especially the ST producing strains. See Oyofo et al. (1995).

TABLE 31

Induction of Immunity Against CS6 Colonization Factor from Enterotoxigenic *E. coil* Following Transcutaneous Immunization with Cholera Toxin

| Immunization Group | Mouse # | Anti-CS6 IgG (ELISA Units) | |
|---|---|---|---|
| | | prebleed | Week 12 |
| CT/CS6 (100/100 μg) Skin | 343 | | 134150 |
| | 344 | | 238874 |
| | 345 | | 675021 |
| | 346 | | 727927 |
| | 347 | | 81596 |
| | Mean | 26 | 264099 |
| CT/CS6 (10/100 μg) Skin | 386 | | 52051 |
| | 387 | | 20402 |
| | 388 | | 62906 |
| | 389 | | 54748 |
| | 390 | | 148747 |
| | Mean | 22 | 56409 |
| CS6 (100 μg) Skin | 391 | | 49 |
| | 392 | | 62 |
| | 393 | | 66 |
| | 394 | | 51 |
| | 395 | | 60 |
| | Mean | 22 | 57 |
| CS6 (5 μg in alum) Intramuscular | 416 | | 30460 |
| | 417 | | 145466 |
| | Mean | 15 | 66565 |

Example 34

Because a large CT molecule (86 Kd) can act as an adjuvant on the skin, we suspected that other adjuvants, particularly those based on bacterial products or motifs, could also be immunostimulatory when placed on the skin. As shown below, unmethylated CpG motifs (CPGs) representative of bacterial DNA do enhance the immune response and may be considered adjuvants. Optionally, transcutaneous immunization with such adjuvants may include hydrating the skin, swabbing with alcohol or acetone, using other penetration enhancers, and combinations thereof.

Bacterial DNA's adjuvant activity confirms that this suspicion was correct. BALB/c mice 6 to 8 weeks of age were shaved and anesthetized as described above. On the day of immunization, the backs of the mice were wiped with isopropanol to enhance penetration. After the alcohol had evaporated (approximately 5 minutes), 100 µl of phosphate buffered saline (PBS) containing 100 µg DNA (CpG1 or CpG2), and 100 µg diphtheria toxoid (DT) was applied to the back for 90 to 120 minutes. Oligonucleotides (ODNs) were synthesized by Oligos Etc. with phosphorothioate linkages to improve stability. Excess antigen was removed. The immunization was repeated 4 and 8 weeks later. Ten weeks after the primary immunization, the animals were bled and the anti-DT titers determined using "ELISA IgG (H+L)" as described above. The results are shown in Table 32.

Co-administration of DT and a negative control DNA (CpG2, TCCAATGAGCTTCCTGAGTCT shown as SEQ ID NO:2) failed to induce a detectable rise in the anti-DT titers. In contrast, addition of DNA containing an unmethylated CpG dinucleotide flanked by two 5' purines and two 3' pyrimidines (immunostimulatory CpG1, TCCATGA CGTTCCTGACGTT shown as SEQ ID NO:3) resulted in a detectable increase in the serum anti-DT IgG titer in five of five animals. Thus bacterial DNA containing appropriate motifs such as CPGs (6 Kd) can be used as adjuvant to enhance delivery of antigen through the skin for induction of antigen specific antibody responses.

TABLE 32

Adjuvant Activity of Bacterial DNA Applied to the Skin Using Penetration Enhancement: Humoral Immune Response

| | Anti-DT IgG (H + L) ELISA Units | | |
|---|---|---|---|
| Animal # | Adjuvant/Antigen | prebleed | Week 10 |
| 7261 | CpG1/DT | | 1171 |
| 7262 | CpG1/DT | | 22750 |
| 7263 | CpG1/DT | | 4124 |
| 7264 | CpG1/DT | | 126 |
| 7265 | CpG1/DT | | 115 |
| Geometric mean | | | 1096 |
| Pooled prebleed | | 6 | |
| 7266 | CpG2/DT | | 19 |
| 7267 | CpG2/DT | | 12 |
| 7268 | CpG2/DT | | 5 |
| 7269 | CpG2/DT | | 5 |
| 7270 | CpG2/DT | | 11 |
| Geometric mean | | | 9 |
| Pooled prebleed | | 5 | |

The effects of transcutaneous immunization can also be detected by T-cell proliferation. BALB/c mice 6 to 8 weeks of age were shaved and anesthetized as described above. On the day of immunization, the backs of the mice were wiped with isopropanol. After the alcohol had evaporated (approximately 5 minutes), 100 µl of phosphate buffered saline (PBS) containing 100 µg DNA (CpG1 or CpG2) and 100 µg diphtheria toxoid (DT) was applied to the back for 90 to 120 minutes. Oligonucleotides (ODNs) were synthesized by Oligos Etc. with phosphorothioate linkages to improve stability. Excess antigen was removed. Immunization was repeated 4 and 8 weeks later. Twelve weeks after the primary immunization, draining (inguinal) lymph nodes were removed and pooled from five immunized animals. The capacity to proliferate in response to media or antigen (DT) was assessed in a standard 4 day proliferation assay using $^3$H incorporation as a readout. The results are shown in Table 33. Co-administration of DT and DNA containing an unmethylated CpG dinucleotide flanked by two 5' purines and two 3' pyrimidines (CpG1) resulted in a detectable increase in the antigen specific proliferative response. Thus, it appears that bacterial DNA containing appropriate motifs can be used as adjuvant to enhance delivery of antigen through the skin for induction of proliferative responses.

TABLE 33

Adjuvant Effect of Bacterial DNA Applied to the Skin: Cell Proliferation

| | Proliferation (cpm) $^3$H Incorporation in Vitro | |
|---|---|---|
| Substances applied | Media | DT |
| Normal lymph nodes | 339 | 544 |
| CpG1/DT | 1865 | 5741 |

Example 35

Given that an adjuvant such as CT can act as an adjuvant on the skin, it was suspected that other adjuvants would be stimulatory when placed on the skin in a manner that hydrates the skin. Genetically altered toxins were used to confirm this suspicion. BALB/c mice 6 to 8 weeks of age were anesthetized, shaved, and immunized as described above. The animals were boosted 3 and 5 weeks after the primary immunization, and sera collected two weeks after the final immunization. The adjuvants used were genetically altered toxins: LTK63, an enzymatically inactive LT derivative, and LTR72, an LT derivative which retains 0.6% of the unmodified LT's enzymatic activity. One hundred µg diphtheria toxoid (DT) was used as antigen.

Anti-DT antibody titers were determined using "ELISA IgG (H+L)" as described above. The results are shown in Table 34. Anti-DT titers were clearly elevated in serum from animals immunized with either LTR63 or LTR72 and DT when compared with titers in serum collected prior to immunization (prebleed). Thus, it appears that genetically detoxified mutants of heat labile enterotoxin (LT) can be used as adjuvants for transcutaneous immunization.

TABLE 34

Use of Genetically Altered Toxins, LTK63 and LTR72, as Adjuvants

| | anti-DT IgG (H + L) ELISA Units | | |
|---|---|---|---|
| Animal # | Adjuvant/Antigen | Prebleed | Week 7 |
| 653 | LTK63/DT | | 20228 |
| 654 | LTK63/DT | | not available |
| 655 | LTK63/DT | | 342 |
| 656 | LTK63/DT | | 2445 |
| 657 | LTK63/DT | | <100 |
| Geometric mean | | | 1140 |
| Pooled prebleed | | <100 | |
| 663 | LTR72/DT | | 12185 |
| 664 | LTR72/DT | | 10917 |
| 665 | LTR72/DT | | 151 |
| 666 | LTR72/DT | | 2057 |
| 667 | LTR72/DT | | 50923 |
| Geometric mean | | | 4620 |
| Pooled prebleed | | <100 | |

Example 36

Another class of compounds, cytokines which are known to act as adjuvants illustrate the principle that adjuvants in general could be expected to act in a fashion similar to cholera toxin. TNF-α is also a Langerhan cell activating compound.

BALB/c mice 6 to 8 weeks of age were shaved and anesthetized as described above. On the day of immunization, the backs of the mice were wiped with isopropanol. After the alcohol had evaporated (approximately 5 minutes), 100 µl of phosphate buffered saline (PBS) containing 0.83 µg TNF-α (recombinant mouse TNF-alpha, Endogen), IL-2 (1 µg recombinant mouse IL-2; Sigma), or mock adjuvant (CpG2) was applied to the skin on the back with 100 µg of diphtheria toxoid (DT) for 90 to 120 minutes. Oligonucleotides (ODNs) were synthesized by Oligos Etc. with phosphorothioate linkages to improve stability. Removal of excess antigen was conducted as previously described. The immunization was repeated 4 and 8 weeks later. Ten weeks after the primary immunization, the animals were bled and the anti-DT titers determined using "ELISA IgG (H+L)" as described above. The results are shown in Table 35.

Co-administration of DT and a mock adjuvant (CpG2) failed to induce a detectable rise in the anti-DT titers. In contrast, topical application of TNF-α, (0.8 µg) resulted in a detectable increase in the serum anti-DT IgG titer in 3 of 5 animals when compared with either anti-DT titers in the mock adjuvant treated mice or sera collected prior to immunization (prebleed). Similarly, topical application of 1 μg IL-2 resulted in a detectable increase in the serum anti-DT IgG titer in 4 of 5 animals when compared with either anti-DT titers in the mock adjuvant treated mice or sera collected prior to immunization (prebleed). Thus, it appears that the cytokines such as IL-2 and TNF-alpha can be used as an adjuvant on the skin and that Langerhans cell activating compounds can be used for transcutaneous immunization.

TABLE 35

Adjuvant Activity of the Cytokine TNF-alpha Applied to the Skin

| Animal # | Adjuvant/Antigen | Anti-DT IgG (H + L) ELISA Units<br>Prebleed | Week 10 |
|---|---|---|---|
| 7326 | TNF-alpha/DT | | 1808 |
| 7327 | TNF-alpha/DT | | 830 |
| 7328 | TNF-alpha/DT | | 7 |
| 7329 | TNF-alpha/DT | | 1477 |
| 7330 | TNF-alpha/DT | | 7 |
| geometric mean | | | 159 |
| pooled prebleed | | 1 | |
| 7331 | IL-2/DT | | 13 |
| 7332 | IL-2/DT | | 111 |
| 7333 | IL-2/DT | | 345 |
| 7334 | IL-2/DT | | 49 |
| 7335 | IL-2/DT | | 35 |
| geometric mean | | | 61 |
| pooled prebleed | | 2 | |
| 7266 | CpG2/DT | | 19 |
| 7267 | CpG2/DT | | 12 |
| 7268 | CpG2/DT | | 5 |
| 7269 | CpG2/DT | | 5 |
| 7270 | CpG2/DT | | 11 |
| geometric mean | | | 9 |
| pooled prebleed | | 5 | |

Example 37

The B-subunit of cholera toxin is another class of adjuvants lack the A-subunit and therefore ADP-ribosyltransferase activity of CT. As such, CTB represents an adjuvant that is unique and may be useful as it is not toxic when ingested.

C57BL/6 mice 6 to 8 weeks of age were anesthetized and shaved as described above. On the day of immunization, the backs of the mice were wiped with isopropanol. After the alcohol had evaporated (approximately 5 minutes), 100 μl of phosphate buffered saline (PBS) containing 100 μg purified cholera toxin B subunit (CTB) and/or 100 μg diphtheria toxoid (DT) was applied to the back for 90 to 120 minutes. Excess antigen was removed. Immunization was repeated 4 and 8 weeks later. Ten weeks after the primary immunization, the animals were bled and the anti-DT titers determined using "ELISA IgG (H+L)" as described above. The results are shown in Table 36.

Anti-DT titers were clearly elevated in serum from animals immunized with CTB and DT when compared with titers in serum from animals treated with DT alone or those in prebleed serum samples as shown in Table 10. Thus, it appears that purified CTB can be used as an adjuvant on the skin.

TABLE 36

Use of Purified Cholera Toxin B Subunit From *V. cholera* as an Adjuvant on the Skin

| Animal # | Adjuvant/Antigen | Anti-DT IgG (H + L) ELISA Units<br>Prebleed | Week 10 |
|---|---|---|---|
| 51 | DT | | 11 |
| 52 | DT | | 7 |
| 53 | DT | | 4 |
| 54 | DT | | 8 |
| 55 | DT | | 7 |
| geometric mean | | | 7 |
| pooled prebleed | | 4 | |
| 81 | CTB/DT | | 14880 |
| 82 | CTB/DT | | 371 |
| 83 | CTB/DT | | 14810 |
| 84 | CTB/DT | | 108 |
| 85 | CTB/DT | | 27 |
| geometric mean | | | 751 |
| pooled prebleed | | 5 | |

Example 38

Adjuvants that are structurally different may exert their influence on the immune system in different ways. Adjuvants that induce their effects by different mechanisms may have either additive or synergistic effects on enhancing the immune response. We found that the use of two adjuvants simultaneously augmented the response to transcutaneous immunization compared to the individual adjuvants alone.

BALB/c mice 6 to 8 weeks of age were shaved and anesthetized as described above. On the day of immunization, the backs of the mice were wiped with isopropanol. After the alcohol had evaporated (approximately 5 minutes), 100 μl of phosphate buffered saline (PBS) containing 100 μg immunostimulatory DNA (CpG1) and/or 100 μg cholera toxin (CT) was applied to the back with 100 μg soluble *leishmania* antigen extract (SLA) for 90 to 120 minutes. SLA is an antigen extract prepared at Walter Reed Army Institute of Research by centrifugal isolation of the soluble proteins in a sonicate of *Leishmania major* promastigotes extract for 90 to 120 minutes. Excess antigen was removed. Immunization was repeated 4 and 8 weeks later. Twelve weeks after the primary immunization draining (inguinal) lymph nodes were removed and pooled from two immunized animals. The capacity to proliferate in response to media or antigen (SLA) was assessed in a standard 4-day proliferation assay using $^3H$ incorporation as a readout. The results are shown in Table 37.

Co-administration of SLA and CpG1 (immunostimulatory DNA containing an unmethylated CpG dinucleotide flanked by two 5' purines and two 3' pyrimidines) or CT resulted in a detectable increase in the antigen specific proliferative response. However, the antigen (SLA) specific proliferative response was approximately 20 times higher in lymph node cell cultures from animals exposed simultaneously to both CpG1 and CT as compared to cultures derived from animals exposed to either adjuvant alone. Thus, it appears that bacterial DNA containing appropriate motifs synergizes with ADP ribosylating exotoxins such as CT as adjuvants on the skin to induce higher immune responses than to either adjuvant alone.

TABLE 37

Synergy Between Immunostimulatory DNA
and ADP Ribosylating Exotoxin (CT)
as Adjuvants When Applied to the Skin

| Substances Applied | Proliferation (cpm) $^3$H Incorporation in Vitro to Antigens | |
|---|---|---|
| | Media | SLA |
| normal lymph nodes | 180 | 219 |
| SLA | 200 | 159 |
| SLA/CpG1 | 1030 | 2804 |
| SLA/CT | 232 | 2542 |
| SLA/CpG1/CT | 2232 | 47122 |

Example 39

Transcutaneous immunization induces potent immune responses when used as a method of delivery alone. We also have found that transcutaneous immunization can be used together with other routes of delivery to stimulate an immune response.

BALB/c mice were 6 to 8 weeks of age. On day 0 both groups of animals received a 50 μl intramuscular (IM) injection of 5 μg DT mixed with alum (25 μg REHYDROGEL in NaCl) into the hind thigh. Eight and 16 weeks later mice in the im/tc/tc group were shaved, anesthetized and immunized by the transcutaneous route (TC) as described above. The immunization solution was applied to the back for 90 to 120 minutes, and then excess antigen was removed. Twenty two weeks after the primary immunization. mice were bled and anti-DT titers determined using "ELISA IgG (H+L)" as described above. The results are shown in Table 38.

A single intramuscular injection of 5 μg DT induced a detectable rise in the serum anti-DT titers as compared with titers in sera collected from the same animals prior to immunization (prebleed). Boosting of the intramuscularly primed mice using the transcutaneous immunization method resulted in an 60 fold rise in the geometric mean titer and clearly all transcutaneously boosted animals had higher anti-DT titers than those observed in the intramuscularly primed group. Thus, transcutaneous immunization can be used to boost antigen specific titers in mice in which the primary immunization with the antigen was by the intramuscular route. We have also found that intramuscularly primed animals can be boosted by transcutaneous immunization. Various combinations of priming and/or boosting by transcutaneous immunization with other immunization routes and/or schedules can be visualized including oral, buccal, nasal, rectal, vaginal, intradermal, gun, or other means of delivery. Additionally, antigens may differ in route and composition including protein alternating with glycoprotein, subunit with holotoxin, DNA priming followed by protein, plasmid DNA by intramuscular immunization followed by plasmid DNA by transcutaneous immunization. Transcutaneous immunization may be used to boost children primed in infancy or adults primed in childhood. The ease of delivery may enhance the efficacy vaccines such as the influenza vaccines by allowing multiple boosts using a patch.

TABLE 38

Boosting of Intramuscularly Primed Animals Using Transcutaneous Immunization

| | | | Anti-DT IgG (H + L) ELISA Units | |
|---|---|---|---|---|
| Animal # | Adjuvant/ Antigen | Route of Administration | Pre- bleed | Week 22 |
| 8563 | DT | IM | | 54227 |
| 8564 | DT | IM | | 11833 |
| 8565 | DT | IM | | 106970 |
| 8566 | DT | IM | | 10830 |
| 8567 | DT | IM | | 4003 |
| Geometric mean | | | | 19711 |
| Pooled prebleed | | | 20 | |
| 8568 | DT/ct + dt/ct + dt | IM/TC/TC | | 628838 |
| 8569 | DT/ct + dt/ct + dt | IM/TC/TC | | 2035507 |
| 8570 | DT/ct + dt/ct + dt | IM/TC/TC | | 1164425 |
| 8571 | DT/ct + dt/ct + dt | IM/TC/TC | | not available |
| 8572 | DT/ct + dt/ct + dt | IM/TC/TC | | 1263138 |
| Geometric mean | | | | 1171368 |
| Pooled prebleed | | | 10 | |
| 8558 | DT/DT/DT | IM/IM/IM | | not available |
| 8559 | DT/DT/DT | IM/IM/IM | | 542669 |
| 8560 | DT/DT/DT | IM/IM/IM | | 770150 |
| 8561 | DT/DT/DT | IM/IM/IM | | 545894 |
| 8562 | DT/DT/DT | IM/IM/IM | | 671898 |
| Geometric mean | | | | 625721 |
| Pooled prebleed | | | 15 | |

Example 40

C57BL/6 mice 6 to 8 weeks of age were immunized as described above. On the day of immunization, the backs of the mice were wiped with isopropanol. After the alcohol had evaporated (approximately 5 minutes), the backs of the mice were hydrated for an additional 5 minutes with water. After gentle blotting of excess water, 100 μl of phosphate buffered saline (PBS) containing DT and/or CT holotoxin and/or recombinant CTB subunit were applied to the skin in the indicated ratios. Two hours later, any remaining antigen was removed by rinsing the skin of the animals with copious amounts of water. Immunization was repeated 4 and 8 weeks later. Twelve weeks after the primary immunization, the animals were bled and the anti-CT titers determined using "ELISA IgG (H+L)" as described above. The results are shown in Table 39.

Administration of the antigen (DT) alone failed to induce a rise in antigen specific antibody levels when compared to the levels observed in prebleed samples. In contrast, epicutaneous application of DT to the skin with either CT holotoxin, CTB subunit, or a combination of CT (2%) and CTB (98%) induced anti-DT titers in the serum. Importantly, while only three out of five mice receiving CTB alone as an adjuvant had potent responses to DT induced, the anti-DT titers in animals receiving 98% CTB and 2% CT were indistinguishable from that observed in animals receiving 100% CT holotoxin alone as adjuvant. Thus, small amounts of holotoxin are able to augment the adjuvant activity of the relatively non-toxic CTB subunit.

TABLE 39

Enhancement of Adjuvanticity of rCTB by Adding a Small
Amount (2%) of CT Holotoxin in the Immunization Mixture

| Immunization | Eartag # | Anti-DT IgG (ELISA Units) | |
|---|---|---|---|
| | | Prebleed | Week 12 |
| DT (100 µg) | 601 | | 49 |
| | 602 | | 37 |
| | 603 | | 18 |
| | 604 | | 30 |
| | 605 | | 31 |
| | geomean | 10 | 31 |
| CT (100 µg) | 606 | | 50 |
| | 607 | | 25 |
| | 608 | | 87 |
| | 609 | | 50 |
| | 610 | | 120 |
| | geomean | 13 | 58 |
| CT/DT (50/100 µg) | 616 | | 67898 |
| | 617 | | 62374 |
| | 618 | | 130778 |
| | 619 | | 1344 |
| | 620 | | 10241 |
| | geomean | 12 | 23791 |
| rCTB/DT (50/100 µg) | 626 | | 30 |
| | 627 | | 341 |
| | 628 | | 2279 |
| | 629 | | 39 |
| | 630 | | 3953 |
| | geomean | 17 | 326 |
| rCTB/CT/DT (49/1/100 µg) | 631 | | 102943 |
| | 632 | | 323154 |
| | 633 | | 2612 |
| | 634 | | 19894 |
| | 635 | | 615 |
| | geomean | 16 | 25433 |

Example 41

Because transcutaneous immunization is so simple and effective, it is possible that an adjuvant placed on the skin at one site may act as an adjuvant for antigen placed at another site. BALB/c mice 6 to 8 weeks of age were immunized as described. Animals were not ear tagged but kept in cages labeled A, C or G. On the day of immunization, the dorsal surface of the mouse ear was treated by gently rubbing the outer skin surface with a cotton-tipped applicator containing 70% isopropanol. After five minutes, the excess water was blotted from water-treated ears and adjuvant (50 µg CT) and/or antigen (100 µg bovine serum albumin or BSA) was applied to the left or right ear surface in 50 µl of phosphate buffered saline (PBS). After about two and a half hours, the ears were rinsed and blotted dry twice. Mice were boosted in a similar fashion four and eight weeks later. Twelve weeks after the primary immunization the animals were bled and the anti-BSA titers determined using "ELISA IgG (H+L)" as described above. The results are shown in Table 40.

Application of BSA alone to the skin was poorly immunogenic with only one of five animals developing an ELISA titer above 100 ELISA units. In contrast, nine of nine animals receiving CT and BSA on the skin developed titers above 100 ELISA units. Of the animals receiving antigen and adjuvant, mice given the materials at the same site (left ear) developed higher (10 fold) anti-BSA titers than animals receiving antigen and adjuvant in separate (left and right) ears. Animals receiving antigen on one ear and adjuvant on another ear, however, developed an anti-BSA immune response that was approximately 30 times higher that animals given BSA alone. Thus, antigen and adjuvant may be delivered by transcutaneous immunization at different sites to elicit a humoral immune response. This immunostimulation may be expected to occur with antigen delivered by other routes and scheduled to include oral, buccal, nasal, rectal, vaginal, intradermal, by gun, and other delivery routes. Additionally, adjuvants may be used with nucleic acid immunization to enhance the response. Such a delivery may not need to be simultaneous to enhance the immune response. For example, an intramuscular injection of plasmid DNA may be followed later by transcutaneous administration of adjuvant. Immunostimulation by CT, LT, TNF-α, CpGs, and similar adjuvants is a surprising result because it had been thought prior to the present invention that molecules greater than 500 daltons in weight could not pass through the skin.

TABLE 40

Delivery of Antigen and Adjuvant at the Same or Distal Sites
on the Skin with Penetration Enhancement.

| Animal # | Adjuvant/Antigen | Anti-BSA IgG (H + L) ELISA Units | |
|---|---|---|---|
| | | Prebleed | Week 12 |
| group G | BSA left ear | | 240 |
| group G | BSA left ear | | 99 |
| group G | BSA left ear | | 40 |
| group G | BSA left ear | | not available |
| group G | BSA left ear | | 15 |
| Geometric mean | | | 61 |
| Pooled prebleed | | 6 | |
| group C | CT/BSA left ear | | 16418 |
| group C | CT/BSA left ear | | 24357 |
| group C | CT/BSA left ear | | 13949 |
| group C | CT/BSA left ear | | 70622 |
| group C | CT/BSA left ear | | not available |
| Geometric mean | | | 25053 |
| Pooled prebleed | | 3 | |
| group A | CT left/BSA right ear | | 106 |
| group A | CT left/BSA right ear | | 23806 |
| group A | CT left/BSA right ear | | 1038 |
| group A | CT left/BSA right ear | | 1163 |
| group A | CT left/BSA right ear | | 8696 |
| Geometric mean | | | 1939 |
| Pooled prebleed | | 15 | |

Example 42

Transcutaneous Immunization (TCI) in Humans

To confirm that transcutaneous immunization was effective in humans, a Phase I trial was conducted using LT to induce serum anti-LT antibodies. Six volunteers received a dose of 500 µg LT, a dose comparable to oral adjuvant doses used for a cholera vaccine (1 mg CTB). LT was produced under GMP conditions at the Swiss Serum and Vaccine Institute (Berne, Switzerland) and was provided by Oravax (Cambridge, Mass.). Volunteers received 500 µg LT mixed in 500 µl of sterile saline which was absorbed onto a two sq. in. cotton gauze pad with polyvinyl backing, and then covered by a 4"×4" TEGADERM dressing. Volunteers were immunized by placing the patch on unmanipulated skin for six hours after which the site was thoroughly rinsed with 500 ml of sterile saline. They were examined on days 1, 2, 3 and 7 after immunization for signs of inflammation at the site where the patch was administered and interviewed for symptoms related to immunization.

Immunization was initiated by placing the patch on unmanipulated skin for six hours, after which the patch was removed and the site was thoroughly rinsed with saline. Individuals were reimmunized after 12 weeks. No adverse reactions were seen, either systemically or at the site of immunization after the first or second immunization. Anti-LT IgG titers were determined as previously described. Results are reported in ELISA units which are defined as the inverse dilution of sample that yields an OD of 1.0. Anti-LT IgA was determined in the same manner as anti-LT IgG using goat anti-human IgA(α)-HRP (Kirkegaard and Perry, Gaithersburg, Md.) enzyme-linked conjugate against a standard IgA curve made using human IgA (ICN). As shown in Table 41, all immunized individuals responded by inducing an increase in serum anti-LT IgG or IgA specific antibodies, defined as a four-fold increase in titer. The mean fold rise in anti-LT IgG was 10.2 and the mean fold rise in serum anti-LT IgA was 7.2. Biopsies of the immunization site and contralateral arm showed no signs of inflammation of the skin. These results confirm that transcutaneous immunization can be practiced in humans without skin irritation or inflammation.

TABLE 41

Mean Fold Rise in Human Anti-LT IgG and IgA.

| Volunteer # | 4 week IgG | 12 week IgG | 16 week IgG |
|---|---|---|---|
| 13 | 15.2 | 9.5 | 12.5 |
| 14 | 1.4 | 1.6 | 1.7 |
| 15 | 11.7 | 15.0 | 12.9 |
| 16 | 1.3 | 0.7 | 16.0 |
| 17 | 12.5 | 51.9 | 58.6 |
| 18 | 1.3 | 2.1 | 4.3 |
| Mean rise IgG | 4.2 | 5.0 | 10.2 |

| Volunteer # | 4 week IgA | 12 week IgA | 16 week IgA |
|---|---|---|---|
| 13 | 7.2 | 4.1 | 10.1 |
| 14 | 4.9 | 4.3 | 4.3 |
| 15 | 4.9 | 5.7 | 4.5 |
| 16 | 1.4 | 1.3 | 7.0 |
| 17 | 15.3 | 29.4 | 28.1 |
| 18 | 1.3 | 1.5 | 3.5 |
| Mean rise IgA | 4.1 | 4.2 | 7.2 |

Example 43

Transcutaneous immunization, because of its ease of application and effectiveness of delivery, allows the application to be given over different draining lymph nodes. This may have the additional advantage of enhancing the immune response. Rabbits were anesthetized, shaved, and immunized as described above. Animals were immunized with 100 μg cholera toxin (CT) and 100 μg influenza hemagglutinin (HA) at one site or two sites on the back. HA and CT were applied at 0, 3 and 5 weeks. Seven weeks after the primary immunization, the animals were bled and the anti-HA titers determined using "ELISA IgG (H+L)" as described above. The results are shown in Table 42.

Anti-HA titers were elevated in serum from 10 of 10 animals immunized with CT and HA when compared with titers in serum from the same animals prior to immunization (prebleed). The geometric mean titer in the two site group was 3 fold higher than that in the one site group suggesting that antigen delivery at multiple sites may be used to enhance immunization. Thus, antigens can be delivered by transcutaneous immunization either at a single or multiple sites on the skin.

TABLE 42

Transcutaneous Delivery of Antigen at a Single or Multiple Sites.

| | | Anti-HA IgG (ELISA Units) | | |
|---|---|---|---|---|
| Animal | Antigen/Adjuvant | prebleed | 7 Weeks | geomean |
| 1 | CT/HA one site | <25 | 1142 | 2596 |
| 2 | CT/HA one site | <25 | 9617 | |
| 3 | CT/HA one site | <25 | 2523 | |
| 4 | CT/HA one site | <25 | 2275 | |
| 5 | CT/HA one site | <25 | 1869 | |
| 6 | CT/HA two sites | <25 | 10348 | 8403 |
| 7 | CT/HA two sites | <25 | 18453 | |
| 8 | CT/HA two sites | <25 | 9778 | |
| 9 | CT/HA two sites | <25 | 15985 | |
| 10 | CT/HA two sites | <25 | 1404 | |

Example 44

Transcutaneous immunization of mice with human-use vaccine CT antigen has been shown to act as an adjuvant for transcutaneous immunization with single toxoids and BSA. Mice were immunized by intramuscular injection (IM) or transcutaneously immunization (TCI) with a variety of human-use vaccine antigens, including a multivalent toxoid vaccine (tetanus and diphtheria toxoids), a yeast expressed recombinant protein (HIV p55 gag), and whole killed rabies viruses using CT as an adjuvant.

BALB/c mice (n=5) were immunized and boosted twice as described by Glenn et al. (1999). Immunizing doses included 100/50/50 μg CT/TT/DT via TCI, versus 3/1/1 μg alum/TT/DT via IM; 100/100 μg LT/DT versus 100 μg DT alone; 100/100 μg CT/p55 via TCI versus 100 μg p55 alone. Mice (n=10) immunized with 17 IE of killed rabies virus were primed intramuscularly twice, and then boosted transcutaneously (17 IE) after light alcohol swabbing of the skin and compared to three IM injections for rabies immunization. Antibody levels against DT, TT, p55, and rabies were determined using ELISA as previously described by Grassi et al. (1989) and Miyamura et al. (1974).

Results are shown in Table 43. Transcutaneous immunization resulted in similar increases in the antibody responses to TT and DT, and the anti-DT neutralization titers were comparable to that elicited by intramuscular immunization. These data show that transcutaneous immunization may be used to induce immune response of comparable magnitude as those induced by existing immunization practices. Transcutaneously boosting of intramuscularly primed animals also resulted in a significant rise in anti-rabies titers in all 10 animals tested (0.53 to 1.03 IU, p<0.02, Student t test). Antibodies to the antigens DT and p55 administered without adjuvants were very low or undetectable, consistent with our previous observations that antigens are only weakly immunogenic when applied without adjuvant. LT also acted as adjuvant in a fashion similar to previous studies using CT. Although the immunizations were not optimized as compared to intramuscular delivery, these antigen-specific responses confirm that transcutaneous immunization may be used for a variety of human-use vaccines from a variety of sources and with a range of sizes and that LT can act as an adjuvant for co-administered vaccine antigens.

TABLE 43

Mouse Antibody Responses to Human-Use Vaccines.

| TCI Antigens | Antibody Specificity | TCI (ELISA Units) | IM/Alum (ELISA Units) |
|---|---|---|---|
| CT + TT + DT | Anti-DT | 135,792 (86,552-146-759) | 85,493 (24,675-238,904) |
| CT + TT + DT | Anti-TT | 30,051 (13,863-53,174) | 94,544 (74,928-113,408) |
| CT + TT + DT | Diphtheria toxin neutralization | 404 (22-2816) | 1,226 (352-11,264) |
| LT + DT | Anti-DT | 4976 (669-46,909) | ND |
| CT + HIV p55 gag | Anti-p55 | 10,630 (1063-52,597) | ND |
| CT + Killed Rabies Virus | Anti-G protein | 1.03 (IU/ml) (0.31-2.77) | 754 (IU/ml) (3.31-17.47) |

ND = not done. ELISA units shown as geometric mean and range in brackets.

Example 45

Human Langerhans Cell Activation

In two volunteers, the site of immunization and the contralateral (i.e., non-immunized) arm were biopsied at 24 hours post-immunization and again at 48 hours after the second immunization. Hematoxylin and eosin (H&E) staining of specimens confirmed the clinical findings suggesting that no inflammation was seen after immunization. Although routine histologic sections were unremarkable, Langerhans cells (LCs) visualized using anti-CD1a staining of specimens from the site of immunization demonstrated greatly enlarged cell bodies but otherwise normal numbers of cells when compared to the control biopsies from the opposite arm, both at 24 and 48 hours. Similar findings were made using anti-HLA-DR and anti-S-100 to visualize LCs. Morphology of LCs in transcutaneously immunized skin was similar in appearance to tonsillar crypt LCs that are thought to be chronically activated by lipopolysaccharides from the flora of the mouth.

Example 46

BALB/c mice 6-8 weeks of age were of age were immunized as described above. On the day of immunization, the backs of the mice were wiped with a gauze pad saturated in saline. After gently blotting excess saline from the skin, 100 μg of diphtheria toxoid was applied to the back in a 100 μl volume. Two hours later any remaining antigen was removed by rinsing the skin of the animals with copious amounts of water. Immunization was repeated 8 and 17 weeks later. Serum was collected four weeks after the final immunization and assayed for anti-DT IgG antibodies by ELISA. Results are shown in Table 44.

As compared to the prebleed serum, all of the animals exposed to diphtheria toxoid developed anti-DT IgG titers following exposure to the antigen alone. Thus, antigen alone, in the absence of a coadministered adjuvant, can be applied to the skin to elicit a systemic immune response to the applied substance.

TABLE 44

Transcutaneous delivery of antigen (diphtheria toxoid) elicits an antigen specific serum IgG response.

| | Anti-DT IgG (ELISA Units) | |
|---|---|---|
| | Week 0 | Week 21 |
| 5162 | pooled | 5498 |
| 5163 | pooled | 30635 |
| 5165 | pooled | 8179 |
| 5196 | pooled | 185 |
| 5198 | pooled | 97 |
| 5200 | pooled | 12667 |
| Geomean | <50 | 2606 |

Example 47

C57BL/6 mice 6-8 weeks of age were of age were immunized as described above. On the day of immunization, the backs of the mice were wiped with a gauze pad saturated in water and a pool of water allowed to remain on the skin surface for approximately 5 minutes. After gently blotting excess water from the skin, graded doses of tetanus toxoid (TTx) from 0 μg to 50 μg were applied to the back in a 50 μl volume. One hour later, any remaining antigen was removed by rinsing the skin of the animals with copious amounts of water. Immunization was repeated 5 and 8 weeks later. Serum was collected two weeks after the final immunization and assayed for anti-TTx IgG antibodies by ELISA. Results are shown in Table 45.

Non-immunized animals (TT "0") and those receiving 1-10 μg of antigen exhibited undetectable serum anti-TT IgG titers. In contrast, 2 of 5 animals exposed to 25 μg TTx and 4 of 5 mice exposed to 50 μg TTx developed serum anti-TTx titers two or more fold greater than the baseline anti-TT IgG titers of ≤20 ELISA units. Thus, antigen alone, in the absence of a coadministered adjuvant, can be applied to the skin to elicit a systemic immune response to the applied substance.

TABLE 45

| Transcutaneous delivery of antigen (tetanus toxoid) elicits an antigen specific serum IgG response. | | | | | | |
|---|---|---|---|---|---|---|
| TTx | Serum anti-tetanus toxoid IgG (ELISA Units) | | | | | |
| (μg) | mouse 1 | mouse 2 | mouse 3 | mouse 4 | mouse 5 | geomean |
| 0 | <20 | <20 | <20 | <20 | <20 | <20 |
| 1 | <20 | <20 | <20 | 21 | 24 | 21 |
| 5 | 37 | 35 | 24 | <20 | <20 | <20 |
| 10 | <20 | 21 | <20 | <20 | <20 | <20 |
| 25 | 549 | 27 | 53 | 36 | 30 | 61 |
| 50 | 1642 | 1307 | 525 | <20 | 114 | 258 |

Example 48

Swabbing the skin with a treated or untreated swab is thought to physically and chemically remove a small portion of the stratum corneum and thus enhance skin penetration. Swabs can be made of materials such as, for example, cotton, nylon, rayon and polyethylene. Alcohol swabbing is thought to remove a small portion of the stratum corneum and acts both as a physical means and chemical means of penetration enhancement. In the example above, the enhancement of the immune response to transcutaneous immunization can be seen with this penetration enhancement method. BALB/c mice 6 to 8 weeks of age were immunized as described above.

Twenty four hours later, the backs of the animals were either wiped with a gauze pad saturated in water ("Water" group) or wiped for approximately 10 seconds with an alcohol pad containing 70% isopropyl alcohol ("Isopropanol" group). The alcohol was allowed to evaporate for approximately 5 minutes. The excess water was removed from the backs of the "Water" group by blotting. All animals were then treated with 20 µg of CT (100 µl of a 0.2 mg/ml solution). Excess antigen was removed as described above.

The anti-CT antibody titers were determined using ELISA as described above for "ELISA IgG (H+L)" three weeks after a single immunization. The results are shown in Table 46. While CT was clearly immunogenic in both groups, the group treated with the alcohol prep pads exhibited a geometric mean titer that was 6 fold higher and the individual titers were more consistent than the "Water" animals. Thus it appears that chemical and physical disruption of the skin surface with alcohol swabs enhances delivery of antigen by the transcutaneous route.

TABLE 46

Enhancement of transcutaneous immunization by chemical penetration enhancement: Anti-CT titers in mice that had the skin treated with an alcohol prep pad before application of the antigen.

| | | Anti-CT IgG (H + L) ELISA Units | |
| --- | --- | --- | --- |
| Animal # | Treatment | Prebleed | Week 3 |
| 7146 | Water | | 1275 |
| 7147 | Water | | 69 |
| 7148 | Water | | 7420 |
| 7149 | Water | | 6025 |
| 7150 | Water | | 388 |
| Geometric mean | | | 1088 |
| Pooled prebleed | | 7 | |
| 7161 | Isopropanol | | 3100 |
| 7162 | Isopropanol | | 14797 |
| 7163 | Isopropanol | | 6670 |
| 7164 | Isopropanol | | 7426 |
| 7165 | Isopropanol | | 7024 |
| Geometric mean | | | 6928 |
| Pooled prebleed | | 7 | |

Example 49

To assess whether chemical penetration enhancement alone might augment transcutaneous immunization a detergent was used on the skin. BALB/c mice 6 to 8 weeks of age were immunized as described above. Twenty-four hours later, the backs of the "Water" group were wiped with a gauze pad saturated in water and a pool of water was placed on the back. Approximately 5 minutes later, excess water was removed and 25 µg CT (50 µl of a 0.5 mg/ml solution) was applied to the back. Alternatively, 24 hours after shaving, the backs of the "5% SDS" group were treated by dripping 300 µl of 5% SDS (sodium dodecyl sulfate detergent—a 1:1 mixture of deionized water and commercial stock of 10% SDS) for approximately 12 minutes followed by blotting off any excess SDS with a dry gauze pad. SDS can be applied to the skin in a carrier such as, for example, a pad and then any excess SDS can be removed with a dry gauze pad. Thereafter the animals were hydrated and immunized as per the "Water" group. Excess antigen was removed as described above.

The anti-CT antibody titers were determined using ELISA as described above for "ELISA IgG (H+L)" two weeks after a single immunization. The results are shown in Tables 47-48. While CT was clearly immunogenic in both groups, the geometric mean titer in the 5% SDS treated group approximately 2 fold higher and the titers were more consistent among the latter animals as compared with the "Water" animals. Thus it appears that chemical disruption of the skin surface with detergent (5% SDS) enhances delivery of antigen by the transcutaneous route.

TABLE 47

Enhancement of transcutaneous immunization by chemical penetration enhancement: Anti-CT titers in mice that had the skin treated with detergent (5% SDS) before application of the antigen.

| | | Anti-CT IgG (H + L) ELISA Units | |
| --- | --- | --- | --- |
| Animal # | Treatment | Prebleed | Week 2 |
| 546 | Water | | 4629 |
| 547 | Water | | 3154 |
| 548 | Water | | 7288 |
| 549 | Water | | 1719 |
| 550 | Water | | 11779 |
| Geometric mean | | | 3678 |
| Pooled prebleed | | 5 | |
| 596 | 5% SDS | | 6945 |
| 597 | 5% SDS | | 2244 |
| 598 | 5% SDS | | 8604 |
| 599 | 5% SDS | | 7093 |
| 600 | 5% SDS | | 12583 |
| Geometric mean | | | 5553 |
| Pooled prebleed | | 1 | |

TABLE 48

Enhancement of transcutaneous immunization by chemical penetration enhancement: Anti-CT titers in mice that had the skin treated with detergent (5% SDS) before application of the antigen.

| | | Anti-CT IgG (H + L) ELISA Units | |
| --- | --- | --- | --- |
| Animal # | Treatment | Prebleed | Week 3 |
| 546 | Water | | 22525 |
| 547 | Water | | 8939 |
| 548 | Water | | 11885 |
| 549 | Water | | 5121 |
| 550 | Water | | 37770 |
| Geometric mean | | | 10521 |
| Pooled, prebleed | | 11 | |
| 596 | 5% SDS | | 102387 |
| 597 | 5% SDS | | 6597 |
| 598 | 5% SDS | | 47245 |
| 599 | 5% SDS | | 45565 |
| 600 | 5% SDS | | 38413 |
| Geometric mean | | | 34725 |
| Pooled prebleed | | 6 | |

Example 50

Another form of chemical penetration enhancement, a depilatory (such as, for example, calcium hydroxide or the like) is widely used in dermatologic experiments and was shown to enhance transcutaneous immunization. BALB/c mice 6 to 8 weeks of age were immunized as described above. Twenty-four hours later, the backs of the "Water" group were wiped with a gauze pad saturated in water and a pool of water was placed on the back. Approximately 5 minutes later, any excess water was removed and 25 µg of CT (50 µl of a 0.5 mg/ml solution) was applied to the back. Alternatively, twenty-four hours after shaving, the backs of the "Ca(OH)$_2$" group were treated with 100 µl of NAIR depilatory cream for approximately 12 minutes followed by wiping off of the formulation with a gauze pad saturated in water. Such treatment can continue for from about 0.1 to 30 minutes preferably about 20 minutes and more preferably about 12 minutes. Thereafter, the animals were hydrated and immunized as per the "Water" group. Excess antigen was removed as described above.

The anti-CT antibody titers were determined using ELISA as described above for "ELISA IgG (H+L)" two weeks after a single immunization. The results are shown in Tables 49-50. While CT was clearly immunogenic in both groups, the geometric mean titer in the Ca(OH)$_2$ treated group was 3 fold higher and the titers were more consistent among the latter animals as compared with the "Water" animals. Thus it appears that chemical disruption of the skin surface with calcium hydroxide, the active ingredient in NAIR depilatory cream, enhances delivery of antigen by the transcutaneous route.

TABLE 49

Enhancement of transcutaneous immunization by chemical penetration enhancement: Anti-CT titers in mice that had the skin treated with calcium hydroxide (NAIR depilatory cream) before application of the antigen.

| | Anti-CT IgG (H + L) ELISA Units | | |
|---|---|---|---|
| Animal # | Treatment | Prebleed | Week 2 |
| 546 | Water | | 4629 |
| 547 | Water | | 3154 |
| 548 | Water | | 7288 |
| 549 | Water | | 1719 |
| 550 | Water | | 11779 |
| Geometric mean | | | 3678 |
| Pooled prebleed | | 5 | |
| 581 | Ca(OH)$_2$ | | 17621 |
| 582 | Ca(OH)$_2$ | | 12261 |
| 583 | Ca(OH)$_2$ | | 7235 |
| 584 | Ca(OH)$_2$ | | 7545 |
| 585 | Ca(OH)$_2$ | | 5997 |
| Geometric mean | | | 10421 |
| Pooled prebleed | | 4 | |

TABLE 50

Enhancement of transcutaneous immunization by chemical penetration enhancement: Anti-CT titers in mice that had the skin treated with calcium hydroxide (NAIR depilatory cream) before application of the antigen.

| | Anti-CT IgG (H + L) ELISA Units | | |
|---|---|---|---|
| Animal # | Treatment | Prebleed | Week 3 |
| 546 | Water | | 22525 |
| 547 | Water | | 8939 |
| 548 | Water | | 11885 |
| 549 | Water | | 5121 |
| 550 | Water | | 37770 |
| geometric mean | | | 10521 |
| pooled prebleed | | 11 | |
| 581 | Ca(OH)$_2$ | | 34222 |
| 582 | Ca(OH)$_2$ | | 45674 |
| 583 | Ca(OH)$_2$ | | 50224 |
| 584 | Ca(OH)$_2$ | | 27270 |
| 585 | Ca(OH)$_2$ | | 21832 |
| Geometric mean | | | 38251 |
| Pooled prebleed | | 15 | |

Example 51

Further studies were conducted to evaluate the effect of chemical penetration enhancement using a keratinolytic formulation (such as a salicylate). BALB/c mice 6 to 8 weeks of age were immunized as described above. Twenty-four hours later, the backs of the "Water" group were wiped with a gauze pad saturated in water and a pool of water was placed on the back. Approximately 5 minutes later, any excess water was removed and 25 µg of CT (50 µl of a 0.5 mg/ml solution) was applied to the back. Alternatively, twenty-four hours after shaving, the backs of the "Salicylate/Water" group were treated with a gauze pad saturated with a 10% salicylate suspension (one tablet of 325 mg ASA) Certified brand aspirin dissolved in 3.25 ml deionized water). Such treatment can continue for from about 0.1 to 30 minutes preferably about 20 minutes and more preferably about 10 minutes. Approximately 10 minutes later any remaining solution was blotted off, the backs of the animals were hydrated with water for 5 minutes, followed by removal of excess water, and then topical application of 25 µg of CT. Excess antigen was removed as described above.

The anti-CT antibody titers were determined using ELISA as described above for "ELISA IgG (H+L)" two weeks after a single immunization. The results are shown in Table 51. While CT was clearly immunogenic in both groups, the geometric mean titer in the salicylate treated group was 4 fold higher and the titers were more consistent among the latter animals as compared with the "Water" animals. Thus it appears that chemical disruption of the skin surface with salicylate enhances delivery of antigen by the transcutaneous route.

TABLE 51

Enhancement of transcutaneous immunization by chemical penetration enhancement: Anti-CT titers in mice that had the skin treated with salicylate (aspirin) before application of the antigen.

| | Anti-CT IgG (H + L) ELISA Units | | |
|---|---|---|---|
| Animal # | Treatment | Prebleed | Week 2 |
| 741 | Water | | 272 |
| 742 | Water | | not available |
| 743 | Water | | 456 |
| 744 | Water | | 443 |
| 745 | Water | | 1395 |
| Geometric mean | | | 526 |
| Pooled prebleed | | 7 | |
| 756 | Salicylate/Water | | 2279 |
| 757 | Salicylate/Water | | 4581 |
| 758 | Salicylate/Water | | 4658 |
| 759 | Salicylate/Water | | 2771 |
| 760 | Salicylate/Water | | 593 |
| Geometric mean | | | 2402 |
| Pooled prebleed | | 36 | |

Example 52

To assess the role of physical/mechanical penetration enhancement, an abrasive, in the form of a common emery board, was used to remove a portion of the stratum corneum. BALB/c mice 6 to 8 weeks of age were immunized as described above. Twenty four hours later, the backs of the animals were either wiped with a gauze pad saturated in water ("Water" group) or brushed 10 times with a medium-grain emery board ("Emery board" group) and then wiped with a gauze pad saturated in water Approxi-mately five minutes after the water treatment, any excess water was removed and 20 µg CT (100 µl of a 0.2 mg/ml) solution applied to the back. Excess antigen was removed as described above.

The anti-CT antibody titers were determined using ELISA as described above for "ELISA IgG (H+L)" three weeks after a single immunization. The results are shown in Table 52.

While CT was clearly immunogenic in both groups, the geometric mean titer in the emery board treated group was 10 fold higher and the titers were more consistent among the latter animals as compared with the "water" animals. Thus it appears that physical disruption of the outer surface of the skin with an emery board enhances delivery of antigen by the transcutaneous route. This can be differentiated from techniques that seek to pierce the skin and deliver antigen through the skin, such as in subcutaneous, intradermal or intramuscular injection.

This simple device could be replaced by other physical disrupting devices to deliver antigens and adjuvants into the epidermis such as microneedles that are of length to disrupt only the stratum corneum or superficial epidermis, devices used for TB tine testing, gas powered guns which do not penetrate the dermis, adhesive tape for tape stripping, or other barrier disruption devices known to disrupt only the stratum corneum or superficial epidermis.

TABLE 52

Enhancement of transcutaneous immunization by physical penetration enhancement: Anti-CT titers in mice that had the skin treated with an emery board before application of the antigen.

| Animal # | Treatment | Prebleed | Anti-CT IgG (H + L) ELISA Units Week 3 |
|---|---|---|---|
| 7146 | Water | | 1275 |
| 7147 | Water | | 69 |
| 7148 | Water | | 7420 |
| 7149 | Water | | 6025 |
| 7150 | Water | | 388 |
| Geometric mean | | | 1088 |
| Pooled prebleed | | 7 | |
| 7151 | Emery board | | 6632 |
| 7152 | Emery board | | 9380 |
| 7153 | Emery board | | 31482 |
| 7154 | Emery board | | 11142 |
| 7155 | Emery board | | 11761 |
| Geometric mean | | | 12074 |
| Pooled prebleed | | 9 | |

Example 53

Another means of physical penetration enhancement was employed using an abrasive pad to mechanically remove a portion of the stratum corneum and allow access to the underlying epidermis. BALB/c mice 6 to 8 weeks of age were immunized as described above. Twenty four hours later, the backs of the animals were either wiped with a gauze pad saturated in water ("Water" group) or wiped with a gauze pad saturated in water followed by rubbing for 10 seconds with a BUF PUF nylon pad to remove the outermost layers of the stratum corneum ("Abrasive" group). Excess water was removed from the backs of the "Water" group and then 20 µg CT (100 µl of a 0.2 mg/ml solution) was applied to the backs of all animals. Excess antigen was removed as described above.

The anti-CT antibody titers were determined using ELISA as described above for "ELISA IgG (H+L)" three weeks after a single immunization. The results are shown in Table 53. While CT was clearly immunogenic in both groups, the geometric mean titer in the abrasive pad-treated group was 2 fold higher and the titers among individual animals were more consistent among the latter animals compared with the "Water" group. Thus it appears that physical disruption of the skin surface with an abrasive pad enhances delivery of antigen by the transcutaneous route.

This simple device could be replaced by other physical penetration devices to deliver antigens and adjuvants into the epidermis such as a needle and tuberculin syringe used for intradermal injection, microneedles that are of length to penetrate only the stratum corneum or superficial dermis, devices used for TB tine testing, abrading patches which have dissolvable crystals such as sucrose or sodium chloride or biodegradable polymers that are impregnated into the patch and rubbed on the skin before securing the patch with antigen either contained in the crystal or in the matrix, gas powered guns, adhesive tape for tape stripping, or other devices known to penetrate only into the epidermis or superficial dermis.

TABLE 53

Enhancement of transcutaneous immunization by physical penetration enhancement: Anti-CT titers in mice that had the skin treated with an abrasive pad before application of the antigen.

| Animal # | Treatment | Prebleed | Anti-CT IgG (H + L) ELISA Units Week 3 |
|---|---|---|---|
| 7146 | Water | | 1275 |
| 7147 | Water | | 69 |
| 7148 | Water | | 7420 |
| 7149 | Water | | 6025 |
| 7150 | Water | | 388 |
| Geometric mean | | | 1088 |
| Pooled prebleed | | 7 | |
| 7166 | Abrasive | | 5376 |
| 7167 | Abrasive | | 2319 |
| 7168 | Abrasive | | 1209 |
| 7169 | Abrasive | | 2871 |
| 7170 | Abrasive | | 2785 |
| Geometric mean | | | 2607 |
| Pooled prebleed | | 8 | |

Example 54

LT effectively immunizes humans by a transcutaneous route. Furthermore, LT acts as an adjuvant for transcutaneous immunization. C57BL/6 mice 6 to 8 weeks of age were immunized as described above. On the day of immunization, the backs of the mice were wiped with isopropanol. After the alcohol had evaporated (approxi-mately 5 minutes), 100 µl of phosphate buffered saline (PBS) containing 100 µg heat labile enterotoxin (LT) and/or 100 µg diphtheria toxoid (DT) was applied to the back for 90 to 120 minutes. Excess antigen was removed as described above. The immu-nization was repeated 4 and 8 weeks later. Ten weeks after the primary immunization the animals were bled and the anti-DT titers determined using an ELISA as described above for "ELISA IgG (H+L)". The results are shown in Table 54.

Anti-DT titers were clearly elevated in serum from animals immunized with LT and DT when compared with titers in serum from animals treated with DT alone or those in prebleed serum samples. Thus it appears that heat labile enterotoxin (LT) can be used as an adjuvant on the skin.

TABLE 54

Use of heat labile enterotoxin (LT) from *E. coli* as an adjuvant on the skin.

| Animal # | Adjuvant/Antigen | Prebleed | Anti-DT IgG (H + L) ELISA Units Week 10 |
|---|---|---|---|
| 51 | DT | | 11 |
| 52 | DT | | 7 |

TABLE 54-continued

Use of heat labile enterotoxin (LT) from *E. coli* as an adjuvant on the skin.

| | Anti-DT IgG (H + L) ELISA Units | | |
|---|---|---|---|
| Animal # | Adjuvant/Antigen | Prebleed | Week 10 |
| 53 | DT | | 4 |
| 54 | DT | | 8 |
| 55 | DT | | 7 |
| Geometric mean | | | 7 |
| Pooled prebleed | | 4 | |
| 71 | LT/DT | | 7126 |
| 72 | LT/DT | | 46909 |
| 73 | LT/DT | | 669 |
| 74 | LT/DT | | 8480 |
| 75 | LT/DT | | 1598 |
| Geometric mean | | | 4970 |
| Pooled prebleed | | 5 | |

Example 55

To assess the role of physical/mechanical penetration enhancement, the superficial layers of the stratum corneum were removed by tape stipping. Tape stripping is an intervention well known in the art to remove the outer layer of the stratum corneum. C57BL/6 mice 6 to 8 weeks of age were immunized as described above. Twenty four hours later, 25 µg CT was applied to the backs of the mice in 50 µl of phosphate buffered saline ("None" group). Alternatively, the skin on the backs of a second group of animals was subjected to mild tape stripping ("Tape stripping" group). The tape stripping procedure was accomplished by applying cellophane SCOTCH tape to the backs, allowing bonding to the skin surface for 3 minutes, followed by gentle removing of the tape. The bonding and removal steps were repeated three times. Twenty-five µg CT was then applied to the backs of the mice in 50 µl of phosphate buffered saline. Antigen remained on the backs for approximately 1.5 hrs at which time excess antigen was removed as described above.

The anti-CT antibody titers were determined using ELISA as described above for "ELISA IgG (H+L)" using sera collected 11 days after the primary immunization. The results are shown in Table 55. CT was immunogenic in both groups as compared to sera collected from the same animals prior to immunization ("Prebleed"). The geometric mean titer in the tape stripped group, however, was 100 fold higher and the titers were more consistent among the latter animals as compared with the "None" animals. Thus it appears that physical disruption of the skin surface using tape stripping enhances delivery of antigen by the transcutaneous route.

This simple device could be replaced by other physical penetration devices to deliver antigens and adjuvants into the epidermis such as a needle and tuberculin syringe used for intradermal injection, microneedles that are of length to penetrate only the stratum corneum or superficial dermis, devices used for TB tine testing, gas powered guns, adhesive tape for tape stripping, or other devices known to penetrate only into the epidermis or superficial dermis. Tape stripping devices could be used in conjunction with other penetration enhancers. Tape stripping devices may be used in conjunction with a marker to delineate the site for patch placement, and may be dispersed in a roll or in individual units.

TABLE 55

Enhancement of transcutaneous immunization by physical penetration enhancement: Anti-CT titers in mice that had the skin stripped using cellophane tape before application of the antigen.

| | | Anti-CT IgG (H + L) ELISA Units | |
|---|---|---|---|
| Animal # | Intervention | Prebleed | Day 11 |
| 976 | None | | 155 |
| 977 | None | | 4 |
| 978 | None | | 4 |
| 979 | None | | 31 |
| 980 | None | | 23 |
| Geometric mean | | | 16 |
| Prebleed | | 2 | |
| 986 | Tape stripping | | 10702 |
| 987 | Tape stripping | | 1285 |
| 988 | Tape stripping | | 5832 |
| 989 | Tape stripping | | 997 |
| 990 | Tape stripping | | 782 |
| Geometric mean | | | 2990 |
| Prebleed | | 3 | |

Example 56

Nucleic acids such as plasmid DNA or RNA can be used to induce an immune response. Such polynucleotides are well known in the art but have not been shown to be effective in inducing immunity by epicutaneous application until the present invention. The use of polynucleotides in transcutaneous immunization with pene-tration enhancement is illustrated in the following example.

C57BL/6 mice 6 to 8 weeks of age were immunized as described above. For the "NP DNA" group the mice were wiped with isopropanol, after the alcohol had evaporated (approximately 10 minutes), the backs were hydrated with water using a saturated gauze pad. Approximately 10 minutes later the any excess water was blotted off and a 100 µg of a DNA plasmid (pCMV-NP) encoding for influenza nucleoprotein was applied to the back in 100 µl of saline.

A second group of NP-DNA mice were subjected to the same immunization protocol except that their backs were tape stripped three times prior to alcohol swabbing ("NP DNA—tape stripping"). The tape stripping procedure was accomplished by applying cellophane SCOTCH tape to the backs, allowing bonding to the skin surface for minutes, followed by gentle removing of the tape.

A third group of mice was engaged in the tape stripping/immunization protocol described and 100 µg of the adjuvant heat labile enterotoxin (LT) was included in the immunization solution. Sixteen days after the primary immunization the animals were bled and the anti-influenza NP titers determined using an ELISA as described above for "ELISA IgG (H+L)". The results are shown in Table 56.

Anti-influenza titers were determined using a split virus antigen (Fluzone) preparation to coat the ELISA plates. ELISA titers were determined in 5 individual animals and the mean optical density reading for each group is shown. All three immunization groups developed anti-influenza titers as compared with titers in serum collected from the same animals prior to immunization (prebleed). As compared with the NP DNA alone group, tape stripping prior to immunization enhanced the anti-Influenza titer in all three serum dilutions tested (1:100, 1:200, 1:400) and addition of an adjuvant (LT) further enhanced this response. Thus, DNA can be used on the skin to induce immune responses to vaccine antigens and its effectiveness can be enhanced by the addition of adjuvants and penetration enhancement such as tape stripping.

TABLE 56

Immuogenicity of DNA applied as antigen on the skin using alcohol penetration enhancement.

| Antigen/ Adjuvant | Intervention | Anti-INF IgG optical density (405 nm) | | | |
|---|---|---|---|---|---|
| | | Prebleed | Day 16 post immunization | | |
| | | 1:100 | 1:100 | 1:200 | 1:400 |
| NP DNA | None | 0.21 | 0.47 | 0.20 | 0.07 |
| NP DNA | Tape stripping | 0.39 | 0.64 | 0.28 | 0.13 |
| NP DNA/LT | Tape stripping | 0.39 | 0.87 | 0.38 | 0.13 |

Example 57

The variety of antigens which can be delivered by transcutaneous immunization is further illustrated by the use of a polysaccharide conjugate vaccine to induce polysaccharide-specific antibodies. BALB/c mice 6 to 8 weeks of age were anesthetized, shaved, and immunized as described in the "immunization procedure". Mice were immunized with cholera toxin (CT) and *Haemophilus influenzae* B polysaccharide (Hib-PS) at 0, 3 and 5 weeks. Seven weeks after the primary immunization, the animals were bled and the anti-Hib-PS titers determined using an ELISA as described above for "ELISA IgG (H+L)". The results are shown in Table 57.

Anti-Hib-PS titers were elevated in serum from 4 of 10 animals immunized with CT and Hib-PS when compared with titers in serum from the same animals prior to immunization (prebleed). Thus transcutaneous immunization can be used to induce an anti-polysaccharide immune response. This is a common human use vaccine antigen and represents an important strategy for immunization.

TABLE 57

Delivery of a conjugated polysaccharide by transcutaneous immunization.

| ear tag # | Antigen/Adjuvant | Anti-Hib PS IgG (µg/ml) | |
|---|---|---|---|
| | | Prebleed | Week 7 |
| 1 | CT/Hib-PS (100 µg/100 µg) | <0.20 | <0.20 |
| 2 | CT/Hib-PS (100 µg/100 µg) | <0.20 | <0.20 |
| 3 | CT/Hib-PS (100 µg/100 µg) | <0.20 | 1.68 |
| 4 | CT/Hib-PS (100 µg/100 µg) | <0.20 | <0.20 |
| 5 | CT/Hib-PS (100 µg/100 µg) | <0.20 | 1.86 |
| 6 | CT/Hib-PS (100 µg/25 µg) | <0.20 | 1.04 |
| 7 | CT/Hib-PS (100 µg/25 µg) | <0.20 | <0.20 |
| 8 | CT/Hib-PS (100 µg/25 µg) | <0.20 | <0.20 |
| 9 | CT/Hib-PS (100 µg/25 µg) | <0.20 | 6.30 |
| 10 | CT/Hib-PS (100 µg/25 µg) | <0.20 | <0.20 |

Example 58

Activation of LT may be performed by incubating the LT with trypsin (or trypsin immobilized on beads) with or without reducing agents (e.g., dithiothreitol) to break the disulphide bonds near the trypsin cleavage site, under standard reaction conditions. Native LT can be activated by incubation of 100 µl of protein with 0.1 µg trypsin in a total reaction volume of 100 µl for 45 min at 37° C. Alternatively, the trypsin can be fixed to beads and the LT may be eluted over the trypsin beads. Trypsin cleavage can be demonstrated by SDS-PAGE (Laemmli, 1970). LT either treated or not treated with trypsin can be mixed with buffer containing dithiothreitol, and heated to 100° C. for 5 min prior to SDS-PAGE analysis. Trypsin-treated LT could have a proteolytic fragment of 21K daltons consistent with trypsin cleavage of the A1 and A2, allowing the A1 subunit to ADP-ribosylate G proteins and therefore exert its toxic effects whereas untreated LT would demonstrate a band at 28K daltons, consistent with an intact A subunit. Activation can further be demonstrated in the mouse Y-1 cell assay in which native LT would be 1,000 fold less active than CT, but trypsin-treated LT would be equally as active as CT. Activation can also be demonstrated using an enzymatic assay, the NAD:agmatine ADP-ribosyltransferase assay. In such an assay, non-trypsin-treated LT would be expected to show low or undetectable activity whereas trypsin-treated LT would be expected to show similar activity as that demonstrated by CT.

Example 59

Transcutaneous immunization may be more useful if the immunization can be performed over a short period of time. It may be useful for example for an immunization to be performed during a routine clinic visit lasting 30 minutes. In this example we show that transcutaneous immunization can be performed in hydrated, alcohol swabbed skin in such a short period.

C57BL/6 mice 6 to 8 weeks of age were immunized as described above. On the day of immunization the backs of the mice were wiped with isopropanol. After the alcohol had evaporated (approximately 10 minutes), 200 µl of water was applied to the back for hydration. Fifteen minutes later, the immunization solution was applied to the back and left for the specified period of time. Excess antigen was removed as described above. Mice were immunized with CT alone (100 µg in 50 µl) at day 0 and with CT plus DT (100 µg each in 100 µl volume) at 4, 6 and 9 weeks. Twelve weeks after the primary immunization the animals were bled and the anti-DT titers determined using an ELISA as described above for "ELISA IgG (H+L)". The results are shown in Table 58.

Anti-DT titers were clearly elevated in serum from all of the animals immunized with CT and DT when compared with titers in serum from the same animals prior to immunization (prebleed). Maximal effects of immunization appeared to occur in animals vaccinated for a period of 60 minutes although the titers were similar at 30 and 120 minutes. Fifteen minutes of immunization seemed less efficient as the titers in this group were approximately 10 fold less than that observed in the 30, 60 and 120 minute groups. Thus, transcutaneous immunization may be accomplished within 15 minutes of antigen application.

TABLE 58

Effect of the duration of antigen application on Immoral immunity induced by transcutaneous immunization.

| ear tag # | Duration of Immunization | Anti-DT IgG (ELISA Units) | | |
|---|---|---|---|---|
| | | Prebleed | Week 12 | geomean |
| 361 | 15 min | 6 | 214 | 300 |
| 362 | 15 min | | 664 | |
| 363 | 15 min | | 314 | |
| 364 | 15 min | | 181 | |
| 365 | 15 min | | 1594 | |
| 366 | 30 min | 8 | 11953 | 13445 |
| 367 | 30 min | | 32478 | |

TABLE 58-continued

Effect of the duration of antigen application on Immoral immunity induced by transcutaneous immunization.

| ear tag # | Duration of Immunization | Prebleed | Anti-DT IgG (ELISA Units) Week 12 | geomean |
|---|---|---|---|---|
| 368 | 30 min | | 24346 | |
| 369 | 30 min | | 3457 | |
| 370 | 30 min | | 99776 | |
| 371 | 60 min | 12 | 75787 | 107963 |
| 372 | 60 min | | 200768 | |
| 373 | 60 min | | 102592 | |
| 374 | 60 min | | 87034 | |
| 375 | 60 min | | 9210 | |
| 376 | 120 min | 4 | 48132 | 48202 |
| 377 | 120 min | | 99362 | |
| 378 | 120 min | | 37308 | |
| 379 | 120 min | | 30255 | |
| 380 | 120 min | | 25149 | |

Example 60

C57BL/6 mice were immunized using cholera toxin (CT) in the following manner: 2 mg of lyophilized CT (List Biological, Campbell, Calif.) was carefully removed from the original vial, weighed on a piece of paper (1.28 mg recovered) and divided into eight approximately equal parts of 160 µg each. Mice that were immunized with powder had 160 µg of CT carefully brushed off the paper onto the skin. The mice were anesthetized and shaved prior to immunization, and the immunizing powder was left on the skin for one hour, after which the mice were thoroughly washed. Pretreatment of the skin with water essentially involved wetting the skin for 5 minutes, blotting the skin dry, and placing the immunizing powder or solution on the skin Mice immunized with liquid were immunized with 100 µl of 1 mg/ml CT in saline. Antibodies were detected by ELISA, as described, two weeks after the initial immunization. Only a single immunization was required. The geometric mean ("geo mean") was calculated from the subtracted titers (14-day titer minus prebleed). Results are shown in Table 59.

The mice immunized with a saline solution of CT demonstrated typical immune responses as previously shown using transcutaneous immunization. When powder was placed on the skin, mice clearly developed high levels of antibodies. When the skin is hydrated prior to immunization, both the antigen delivered in aqueous form and antigen delivered in powder form were able to induce very high levels of antibodies. But mice immunized with the dry powder achieved consistently higher levels of antibodies.

TABLE 59

Immunization of mice following topical application of 160 µg of lyophilized antigen (cholera toxin) to the skin.

| ear tag # | Pretreatment | Antigen Form | Prebleed | Anti-CT IgG (ELISA Units) 14-day titer | geo mean |
|---|---|---|---|---|---|
| 967 | None | liquid | <5 | 2637 | 1465 |
| 969 | None | liquid | | 814 | |
| 996 | None | powder | <5 | 11395 | 4957 |
| 997 | None | powder | | 3223 | |
| 998 | None | powder | | 10067 | |
| 999 | None | powder | | 1633 | |
| 970 | $H_2O$ | liquid | <5 | 12316 | 25356 |
| 971 | $H_2O$ | liquid | | 26777 | |
| 965 | $H_2O$ | liquid | | 49434 | |
| 961 | $H_2O$ | powder | <5 | 26966 | 29490 |
| 962 | $H_2O$ | powder | | 39211 | |
| 963 | $H_2O$ | powder | | 26612 | |
| 964 | $H_2O$ | powder | | 26879 | |

Example 61

C57BL/6 mice were immunized using cholera toxin (CT) in the following manner: 1 mg of lyophilized CT (List Biological, Campbell, Calif.) was carefully removed from the original vial, onto a piece of paper and divided into 20 equal parts of 50 µg each. Mice that were immunized with powder had 50 µg of CT carefully brushed off the paper onto the skin. The mice were anesthetized and shaved prior to immunization, and the immunizing powder was left on the skin for one hour, after which the mice were thoroughly washed. Pretreatment of the skin with water ($H_2O$) essentially involved wetting the skin for 5 minutes, blotting the skin dry with gauze, and placing the immunizing powder or solution on the skin. Mice that were swabbed with alcohol (alc) prior to immunization has an isopropyl alcohol (70%) swab rubbed gently 20 times across the skin. Mice immunized with liquid were immunized with 50 µl of 1 mg/ml CT in saline. Antibodies were detected by ELISA, as described, two weeks after the initial immunization. Only a single immunization was required. The geometric mean ("geo mean") was calculated from the subtracted titers (14-day titer minus prebleed). Results are shown in Table 60.

The mice immunized with a saline solution of CT demonstrated typical immune responses as previously shown using transcutaneous immunization. Again, when powder was placed on the skin, mice clearly developed high levels of antibodies. When the skin was hydrated prior to immunization both the antigen delivered in aqueous form and antigen delivered in powder form were able to induce high levels of antibodies. Mice immunized using the dry powder achieved very high levels of antibodies with consistently high responses. Alcohol swabbing did not appear to interfere with the immune responses induced by powder immunization. This second experiment shows that dry formulations may be used in immunization, with or without pretreatment of the skin.

TABLE 60

Immunization of mice following topical application of 50 µg of lyophilized antigen (cholera toxin) to the skin.

| ear tag # | Pretreatment | Antigen Form | Prebleed | Anti-CT IgG (ELISA Units) 14-day titer | geo mean |
|---|---|---|---|---|---|
| 11707 | None | liquid | <10 | 2271 | 251 |
| 11708 | None | liquid | | 327 | |
| 11709 | None | liquid | | 247 | |
| 11710 | None | liquid | | 286 | |
| 11711 | None | liquid | | 19 | |
| 11712 | None | powder | <10 | 53 | 555 |
| 11713 | None | powder | | 1750 | |
| 11714 | None | powder | | 954 | |
| 11715 | None | powder | | 1731 | |

TABLE 60-continued

Immunization of mice following topical application of 50 μg of lyophilized antigen (cholera toxin) to the skin.

| ear tag # | Pretreatment | Antigen Form | Prebleed | Anti-CT IgG (ELISA Units) 14-day titer | geo mean |
|---|---|---|---|---|---|
| 11716 | None | powder | | 342 | |
| 11717 | H$_2$O | liquid | <10 | 8645 | 11826 |
| 11718 | H$_2$O | liquid | | 14958 | |
| 11719 | H$_2$O | liquid | | 13622 | |
| 11720 | H$_2$O | liquid | | 13448 | |
| 11721 | H$_2$O | liquid | | 9765 | |
| 11722 | H$_2$O | powder | <10 | 4614 | 4487 |
| 11723 | H$_2$O | powder | | 7451 | |
| 11724 | H$_2$O | powder | | 2536 | |
| 11725 | H$_2$O | powder | | 3580 | |
| 11726 | H$_2$O | powder | | 5823 | |
| 11727 | alc/H$_2$O | liquid | <10 | 4656 | 7595 |
| 11728 | alc/H$_2$O | liquid | | 8131 | |
| 11729 | alc/H$_2$O | liquid | | 3728 | |
| 11730 | alc/H$_2$O | liquid | | 11335 | |
| 11731 | alc/H$_2$O | liquid | | 15797 | |
| 11732 | alc/H$_2$O | powder | <10 | 22100 | 7327 |
| 11733 | alc/H$_2$O | powder | | 6607 | |
| 11734 | alc/H$_2$O | powder | | 6204 | |
| 11735 | alc/H$_2$O | powder | | 7188 | |
| 11736 | alc/H$_2$O | powder | | 3244 | |

Example 62

C57BL6 mice were immunized using cholera toxin (CT) in the following manner: BALB/c mice were immunized using cholera toxin (CT) in the following manner. Five mg of lyophilized CT (List Biological, Campbell, Calif.) was dissolved in 1 ml of sterile water to make a 5 mg/ml solution. For the powder immunization, 5 μl of this solution was allowed to air dry at room temperature on a glass slide. The residual powder was then scraped off on the back of the mouse skin to be immunized. Thus, mice that were immunized with powder had 25 μg of CT carefully brushed off the slide onto the skin. Mice that were immunized with the dry patch had a 1 cm×1 cm portion of a chemwipe onto which 5 μl of 5 mg/ml CT was placed on a 4 cm×4 cm square of plastic wrap (Saran) and allowed to air dry at room temperature. The chem wipe and plastic wrap were then placed with the chem wipe in direct contact with the skin of the mouse to be immunized and covered with the plastic wrap. The 'wet' patch used a chem wipe and plastic wrap 'patch' made by a similar technique, with the exception that 30 μl of sterile water was pipetted onto the dry patch after it was placed on the skin and plastic wrap was placed over the wet patch.

The mice were anesthetized and shaved prior to immunization, and the immunizing powder was left on the skin for one hour, after which the mice were thoroughly washed. Pretreatment of the skin with water (H$_2$O) essentially involved wetting the skin for 5 minutes, blotting the skin dry with gauze, and placing the immunizing powder or solution on the skin. Mice immunized with liquid were immunized with 25 μl of 1 mg/ml CT in saline. Antibodies were detected by ELISA, as described, two weeks after the initial immunization. Only a single immunization was required. The geometric mean ("geo mean") was calculated from the subtracted titers (14-day titer minus prebleed).

Results are shown in Table 61. The mice immunized with a saline solution of CT on pretreated skin demon-strated typical immune responses as previously shown using transcutaneous immunization with BALB/c mice (modest responder mice). Again, when powder was placed on the skin, mice clearly developed high levels of antibodies when the skin is hydrated prior to immunization. Both the patch placed on hydrated skin and the patch hydrated at the time of immunization achieved high levels of antibodies with consistently high responses. This shows that dry formulations may be used in patch form for immunization on the skin.

TABLE 61

Immunization of mice following topical application of 25 μg of lyophilized antigen (cholera toxin) to the skin in an intermediate responder mouse strain (BALB/c).

| ear tag # | Pretreatment | Antigen Form | Prebleed | Anti-CT IgG (ELISA Units) 14-Day titer | geo mean |
|---|---|---|---|---|---|
| 806 | H$_2$O | liquid | <10 | 3177 | 1011 |
| 807 | H$_2$O | liquid | | 773 | |
| 809 | H$_2$O | liquid | | 266 | |
| 810 | H$_2$O | liquid | | 1976 | |
| 825 | H$_2$O | liquid | | 820 | |
| 821 | H$_2$O | dry patch | <10 | 37020 | 5315 |
| 822 | H$_2$O | dry patch | | 15090 | |
| 823 | H$_2$O | dry patch | | 12952 | |
| 824 | H$_2$O | dry patch | | 7419 | |
| 808 | H$_2$O | dry patch | | 79 | |
| 826 | None | wet patch | <10 | 11959 | 8042 |
| 827 | None | wet patch | | 24894 | |
| 828 | None | wet patch | | 11614 | |
| 829 | None | wet patch | | 10658 | |
| 830 | None | wet patch | | 913 | |
| 831 | H$_2$O | powder | <10 | 9504 | 4955 |
| 832 | H$_2$O | powder | | 4996 | |
| 833 | H$_2$O | powder | | 9841 | |
| 834 | H$_2$O | powder | | 358 | |
| 835 | H$_2$O | powder | | 17854 | |
| 836 | None | powder | <10 | 63 | 17 |
| 837 | None | powder | | 6 | |
| 838 | None | powder | | 275 | |
| 839 | None | powder | | 3 | |
| 840 | None | powder | | 4 | |

REFERENCES

Alba and Katz (1990) J. Immunol. 145: 2791-2796.
Alving and Wassef (1994) AIDS Res. Hum. Retro. 10 (suppl. 2): S91-S94.
Antel et al. (1996) Nature Medicine 2: 1074-1075.
Ausubel et al. (1996) *Current Protocols in Molecular Biology*, Wiley, New York, N.Y.
Bacci et al. (1997) Eur. J. Immunol. 27: 442-448.
Bagot et al. (1997) Tissue Antigens 50: 439-448.
Bathurst et al. (1993) Vaccine 11: 449-456.
Bellinghausen et al. (1996) J. Invest. Dermatol. 107: 582-588.
Blauvelt et al. (1995) J. Invest. Dermatol. 104: 293-296.
Blum (1995) Digestion 56: 85-95.
Badanszky (1993) *Peptide Chemistry*, Springer-Verlag, New York, N.Y.
Bos (1997a) Clin. Exp. Immunol. 107 (suppl. 1): 3-5.
Bos (1997b) *Skin Immune System*, 2nd Ed., CRC Press, Boca Raton, Fla.
Burnette et al. (1994) In: *Bioprocess Technology* (eds. Burnette et al.), pp. 185-203.
Castano et al. (1995) Science 269: 223-226.
Caughman et al. (1986) Proc. Natl. Acad. Sci. USA 83: 7438-7442.
Celluzzi and Falo (1997) J. Invest. Dermatol. 108: 716-720.
Chang et al. (1989) Proc. Natl. Acad. Sci. USA 86: 6343-6347.
Chang et al. (1992) J. Immunol. 139: 548-555.
Chang et al. (1994) J. Immunol. 152: 3483-3490.

Chen et al. (1998) Infect. Immun. 66: 1648-1653.
Condon et al. (1996) Nature Medicine 2: 1122-1128.
Craig (1965) In: *Proceedings of the Cholera Research Symposium*, Honolulu, U.S. Public Health Service Publication No. 1328, pp. 153-158.
Delenda et al. (1994) J. Gen. Viral. 75: 1569-1578.
Deprez et al. (1996) Vaccine 14: 375-382.
Deutscher (1990) *Guide to Protein Purification*, Academic Press, San Diego, Calif.
Dickinson and Clements (1995) Infect. Immun. 63: 1617-1623.
Dragunsky et al. (1992) Vaccine 10: 735-736.
Elson and Dertzbaugh (1994) In: *Handbook of Mucosal Immunology* (eds. Ogra et al.) Academic Press, San Diego, Calif., pp. 391 et seq.
Emile et al. (1995) Virchows Arch. 427: 125-129.
Enk et al. (1993) J. Immunol. 150: 3698-3704.
Finkelstein and LoSpallutto (1969) J. Exp. Med. 130: 185-202.
Fonseca et al. (1994) Vaccine 12: 279-285.
Frankenburg et al. (1996) Vaccine 14:923-929.
Fries et al. (1992a) Proc. Natl. Acad. Sci. USA 89: 358-362.
Fries et al. (1992b) Infect. Immun. 60: 1834-1839.
Furue et al. (1995) J. Dermatol. Sci. 10: 213-219.
Glenn et al. (1995) Immunol. Lett. 47: 73-78.
Glenn et al. (1998a) Nature 391: 851.
Glenn et al. (1998b) J. Immunol. 161: 3211-3214.
Glenn et al. (1999) Infect. Immun. 67: 1100-1106.
Goeddel (1990) *Gene Expression Technology*, Academic Press, San Diego, Calif.
Gordon and Ramsey (1997) *Vaccine, Vaccination and the Immune Response*, Lippincott-Raven, New York, N.Y.
Gramzinski (1997) Vaccine 15: 913-915.
Grassi et al. (1989) J. Clin. Microbiol. 27: 899-902.
Gregoriadis (1992) *Liposome Technology*, CRC Press, Boca Raton, Fla.
Gregoriadis (1993) *Liposome Preparation and Related Techniques*, 2nd Ed., CRC Press, Boca Raton, Fla.
Grosjean et al. (1997) J. Exp. Med. 186: 801-812.
Hammerberg et al. (1998) J. Exp. Med. 187: 1133-1138.
Herrington et al. (1991) Am. J. Trop. Med. Hyg. 45: 695-701.
Herz et al. (1998) Intl. Arch. Allergy Immunol. 115: 179-190.
Inaba et al. (1995) Cell. Immunol. 163: 148-156.
Jahrling et al. (1996) Arch. Virol. Suppl. 11: 135-140.
Janeway and Travers (1996) *Immunobiology*, Churchill Livingstone, New York, N.Y.
Janson and Ryden (1989) *Protein Purification*, VCH, New York, N.Y.
Jurgens et al. (1995) J. Immunol. 155: 5184-5189.
Karp et al. (1996) Science 273: 228-231.
Katkov (1996) Med. Clin. North Am. 80: 189-200.
Khusmith et al. (1991) Science 252: 715-718.
Kleinau et al. (1994) Clin. Exp. Immunol. 96: 281-284.
Kounnas et al. (1992) J. Biol. Chem. 267: 12420-12423.
Kriegler (1990) *Gene Transfer and Expression*, Stockton Press, New York, N.Y.
Kripke et al. (1990) J. Immunol. 145: 2833-2838.
Krueger and Barbieri (1995) Clin. Microbiol. Rev. 8: 34-47.
Laemmli (1970) Nature 227: 680-685.
Lee and Chen (1994) Infect. Immun. 62: 3594-3597.
Leung (1995) J. Invest. Dermatol. 105 (Suppl. 1): 37S-42S.
Lieberman and Greenberg (1996) Adv. Pediatr. Infect. Dis. 11: 333-363.
Lu et al. (1997) Vaccine Res. 6: 1-13.
Lycke and Holmgren (1986) Immunology 59: 301-308.
McClements et al. (1997) Vaccine 15: 857-860.
Malik et al. (1991) Proc. Natl. Acad. Sci. USA 88: 3300-3304.
Mast and Krawczynski (1996) Arum. Rev. Med. 47: 257-266.
Medzhitov and Janeway (1997) Curr. Opin. Immunol. 9: 4-9.
Migliorini et al. (1993) Eur. J. Immunol. 23: 582-585.
Mitsuda et al. (1995) Biochem. Biophys. Res. Commun. 216: 399-405.
Miyamura et al. (1974) J. Biol. Stand. 2: 203-209.
Morein and Simons (1985) Vaccine 3: 83-93.
Morrelli et al. (1996) Immunol. 89: 126-134.
Morrelli et al. (1997) Adv. Exp. Med. Biol. 417: 133-138.
Moschella (1996) *Cutaneous Medicine and Surgery*, W.B. Saunders, Philadelphia, Pa.
Moschella and Hurley (1992) *Dermatology*, 3rd Ed., Harcourt Brace Janovitch, Philadelphia, Pa.
Moss and Vaughan (1995) J. Biol. Chem. 270: 12327-12330.
Munoz et al. (1990) J. Exp. Med. 172: 95-103.
Murphy et al. (1998) J. Cutan. Pathol. 25: 30-34.
Murray (1991) *Gene Transfer and Expression Protocols*, Humana Press, Clifton, N. J.
Nashar et al. (1997) Immunology 91: 572-578.
Newman et al. (1997) Vaccine 15: 1001-1007.
Nohria and Rubin (1994) Biotherapy 7: 261-269.
Ockenhouse et al. (1991) Proc. Natl. Acad. Sci. USA 88: 3175-3179.
Oyofo et al. (1995) Microbiol. Res. 150: 429-436.
Ozaea et al. (1995) Arch. Dermatol. Res. 287: 524-528.
Paul and Cevc (1995) Vaccine Res. 3: 145-164.
Paul et al. (1995) Eur. J. Immunol. 25: 3521-3524.
Paul and Seder (1994) Cell 76: 241-251.
Pertmer et al. (1996) J. Viral. 70: 6119-6125.
Pessi et al. (1991) Eur. J. Immunol. 24: 2273-2276.
Pierce (1978) J. Exp. Med. 148: 195-206.
Pierce and Reynolds (1974) J. Immunol. 113: 1017-1023.
Plotkin and Mortimer (1994) *Vaccines*, 2nd Ed., W.B. Saunders, Philadelphia, Pa.
Prayaga et al. (1997) Vaccine 15: 1349-1352.
Prigozy et al. (1997) Immunity 6: 187-197.
Ramiya et al., (1997) J. Autoimmun., 10: 287-292.
Rappuoli et al. (1995) Intl. Archiv. Allergy Immunol. 108: 327-333.
Rappuoli et al. (1996) Adv. Exp. Med. Biol. 397: 55-60.
Ribi et al. (1988) Science 239: 1272-1276.
Richards et al. (1995) In: *Vaccine Design* (eds., Powell and Newman), Plenum, New York, N.Y.
Rietschel et al. (1994) FASEB J. 8: 217-225.
Roberts and Walker (1993) In: *Pharmaceutical Skin Penetration Enhancement* (eds., Walters and Hadgraft), Marcel Dekker, New York, N.Y.
Saloga et al. (1996a) J. Invest. Dermatol. 106: 982-988.
Saloga et al. (1996b) Exp. Dermatol. 5: 65-71.
Sasaki et al. (1998) Clin. Exp. Immunol. 111: 30-35.
Schneerson et al. (1996) Lancet 348: 1289-1292.
Schuler and Steinman (1985) J. Exp. Med. 161: 526-546.
Schwarzenberger and Udey (1996) J. Invest. Dermatol. 106: 553-558.
Scopes (1993) *Protein Purification*, Springer-Verlag, New York, N.Y.
Seder and Paul (1994) Annu. Rev. Immunol. 12: 635-673.
Serres et al. (1996) Arch. Dermatol. Res. 288: 140-146.
Shafara et al. (1995) Ann. Intern. Med. 125: 658-668.
Shimada et al. (1987) J. Immunol. 139: 2551-2555.
Shriver et al. (1997) Vaccine 15: 884-887.
Sieling et al. (1999) J. Immunol. 162, 851-858.
Skeiky et al. (1995) J. Exp. Med. 181: 1527-1537.
Smedile et al. (1994) Prog. Liver Dis. 12: 157-175.
Smucny et al. (1995) Am. J. Trop. Med. Hyg. 53: 432-437.
Spangler (1992) Microbial. Rev. 56: 622-647.
Stacey et al. (1996) J. Immunol. 157: 2116-2122.

Staniek et al. (1996) Acta Dermatol. Venerol. 76: 282-286.
Stingl et al. (1977) Nature 268: 245-248.
Stingl et al. (1989) Immunol. Ser. 46: 3-42.
Stoute et al. (1997) New Engl. J. Med. 336: 86-91.
Streilein and Grammer (1989) J. Immunol. 143: 3925-3933.
Strobl et al. (1997) Blood 90: 1425-1434.
Summers and Smith (1987) *A Manual of Methods for Baculovirus Vectors and Insect Cell Culture Procedure*, Texas Agricultural Experiment Station Bulletin, No. 1555.
Svennerholm et al. (1983) J. Infect. Dis. 147: 514-522.
Tam (1988) Proc. Natl. Acad. Sci. USA 85: 5409-5413.
Tew et al. (1997) Immunol. Rev. 156: 39-52.
Trach et al. (1997) Lancet 349: 231-235.
Udey (1997) Clin. Exp. Immunol. 107 (Suppl. 1): 6-8.
Vajdy and Licke (1995) Immunology 86: 336-342.
Vandenbark et al. (1996) Nature Medicine 2: 1109-1115.
Vosika et al. (1984) Cancer Immunol. Immunother. 18: 107-112.
Vreden et al. (1991) Am. J. Trop. Med. Hyg. 45: 533-538.
Wang et al. (1995) J. Immunol. 154: 2784-2793.
Wang et al. (1996a) J. Immunol. 156: 4077-4082.
Wang et al. (1996b) Immunol. 88: 284-288.
White et al. (1993) Vaccine 11: 1341-1346.
Wiedermann et al. (1998) Clin. Exp. Immunol. 111: 144-151.
Wiesmueller et al. (1991) Immunology 72: 109-113.
Wisdom (1994) Peptide Antigens, IRL Press, Oxford, UK.
Zeng et al. (1997) Science 277: 339-345.
Zhang et al. (1995) Infect. Immun. 63: 1349-1355.

All published articles, books, patents, and patent applications are incorporated by reference in full or relevant portion where they are cited. Such publications are indicative of the skill of the art and provide further illustration of art-known practices.

From the foregoing, it would be apparent to persons skilled in the art that other antigens, antigen presenting cells, vaccine formulations, and processes for administering a formulation than those described or exemplified can be used to achieve the objectives and advantages of the present invention. In particular, the present invention may be practiced without perforating intact skin, or with superficial penetration or micropenetration of the skin, in contrast to the prior art which taught penetration to at least the dermis to access the vasculature (e.g., vaccination by injection with hypodermic injection). Thus, it is to be understood that modifications of and variations in the described invention will be obvious to those skilled in the art without departing from the novel aspects of the present invention and such variations are intended to come within the scope of the claims below.

Accordingly, the present invention may be embodied in other specific forms without departing from its spirit or essential characteristics. The described embodiments should be considered only as illustrative, not restrictive, because the scope of the present invention will be indicated by the original breadth of the appended claims rather than by the foregoing description. All modifications which come within the meaning and range of the lawful equivalency of the claims are to be embraced within their scope. In that sense, no particular arrangement of product components or order of process steps is intended to limit the scope of the claimed invention unless explicitly recited therein.

We claim:

1. A method for inducing an antigen-specific immune response in a subject comprising:
pretreating an area of the subject's skin,
applying a formulation epicutaneously to said pretreated area, wherein said formulation comprises an antigen which comprises a pathogen or is derived from a pathogen and does not include a liposome, wherein said formulation is applied in dry form, and wherein said pretreating enhances skin penetration without perforating the skin's dermis layer thereby inducing an antigen-specific immune response in the subject.

2. The method of claim 1, wherein the pathogen is selected from the group consisting of virus, bacterium, fungus and parasite.

3. The method of claim 2, wherein the bacterium is *Bacillus anthracis*.

4. The method of claim 2, wherein the virus is influenza virus.

5. The method of claim 1, wherein the antigen comprises the recombinant protective antigen (rPA) of *Bacillus anthracis*.

6. The method of claim 1, wherein the antigen comprises influenza virus hemagglutinin.

7. The method of claim 1, wherein the antigen is selected from the group consisting of carbohydrate, a glycolipid, glycoprotein, lipid, lipoprotein, phospholipid, polypeptide, protein, fusion protein, and chemical conjugates thereof.

8. The method of claim 1, wherein the antigen is a nucleic acid.

9. The method of claim 1, wherein the antigen is a multivalent antigen.

10. The method of claim 1, wherein the antigen also acts as an adjuvant.

11. The method of claim 1, wherein the formulation further comprises a pharmaceutically acceptable carrier or vehicle.

12. The method of claim 1, wherein the formulation further comprises at least one additive or a combination of additives.

13. The method of claim 12, wherein the additive is selected from the group consisting of excipients, preservatives and stabilizers.

14. The method of claim 1, wherein the antigen is applied via a patch.

15. The method of claim 1, wherein pretreating comprises applying to the skin a chemical means, a physical means, a mechanical means, a hydration means, or a combination thereof.

16. The method of claim 15, wherein the chemical is an alcohol, an acetone, a detergent, a depilatory agent, a keratinolitic formulation, or a combination thereof.

17. The method of claim 1, wherein pretreating comprises applying a device.

18. The method of claim 17, wherein the device is selected from a group consisting of a tape stripping device, a swab, an emery board, an abrasive pad, a microneedle comprising device, a device comprising a tine disk, a propellant device, an electroporation device, an ultrasound device, and an ionophoresis device.

* * * * *